(12) United States Patent
Xu et al.

(10) Patent No.: US 12,409,233 B2
(45) Date of Patent: Sep. 9, 2025

(54) ANTI-PD-L1 SINGLE-DOMAIN ANTIBODY AND DERIVATIVES AND USE THEREOF

(71) Applicant: BIOTHEUS INC., Guangdong (CN)

(72) Inventors: Yifeng Xu, Guangdong (CN); Tianhang Zhai, Guangdong (CN); Zhijun Yuan, Guangdong (CN); Andy Tsun, Guangdong (CN); Tsoyue Joanne Sun, Guangdong (CN); Weifeng Huang, Guangdong (CN)

(73) Assignee: BIOTHEUS INC., Guangdong (CN)

( * ) Notice: Subject to any disclaimer, the term of this patent is extended or adjusted under 35 U.S.C. 154(b) by 854 days.

(21) Appl. No.: 17/642,171

(22) PCT Filed: Sep. 7, 2020

(86) PCT No.: PCT/IB2020/058303
§ 371 (c)(1),
(2) Date: Mar. 10, 2022

(87) PCT Pub. No.: WO2021/048725
PCT Pub. Date: Mar. 18, 2021

(65) Prior Publication Data
US 2022/0315658 A1 Oct. 6, 2022

(30) Foreign Application Priority Data

Sep. 12, 2019 (CN) .......................... 201910863109.0

(51) Int. Cl.
| | |
|---|---|
| *C07K 14/71* | (2006.01) |
| *A61K 47/68* | (2017.01) |
| *A61P 35/00* | (2006.01) |
| *C07K 16/28* | (2006.01) |
| *A61K 39/00* | (2006.01) |

(52) U.S. Cl.
CPC .......... *A61K 47/6849* (2017.08); *A61P 35/00* (2018.01); *C07K 14/71* (2013.01); *C07K 16/2827* (2013.01); *A61K 2039/505* (2013.01); *C07K 2317/565* (2013.01); *C07K 2317/569* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | |
|---|---|---|
| 2013/0034559 A1 | 2/2013 | Queva et al. |
| 2018/0030137 A1 | 2/2018 | Van Eenennaam et al. |
| 2018/0291103 A1 | 10/2018 | Xu et al. |
| 2019/0177416 A1 | 6/2019 | Ting et al. |
| 2022/0002418 A1 | 1/2022 | Zhu et al. |
| 2022/0041702 A1 | 2/2022 | Liu et al. |
| 2022/0315658 A1 | 10/2022 | Xu et al. |
| 2023/0031229 A1 | 2/2023 | Beirnaert |
| 2023/0399391 A1 | 12/2023 | Bachner et al. |

FOREIGN PATENT DOCUMENTS

| | | |
|---|---|---|
| CN | 102753577 A | 10/2012 |
| CN | 103254309 | 8/2013 |
| CN | 103965363 A | 8/2014 |
| CN | 107849130 A | 3/2018 |
| CN | 109053895 A | 12/2018 |
| CN | 109096396 A | 12/2018 |
| CN | 109942712 A | 6/2019 |
| CN | 110003333 A | 7/2019 |
| CN | 110305210 A | 10/2019 |
| CN | 110627906 A | 12/2019 |
| CN | 110835375 A | 2/2020 |
| CN | 112480253 A | 3/2021 |
| WO | 03/016466 A2 | 2/2003 |
| WO | 2015/118175 A2 | 8/2015 |
| WO | 2019/096121 A1 | 5/2019 |
| WO | 2019/166622 A1 | 9/2019 |
| WO | 2019/169212 A1 | 9/2019 |
| WO | 2019184909 A1 | 7/2020 |
| WO | 2020151761 A1 | 7/2020 |

OTHER PUBLICATIONS

First Office Action and Search Report from Chinese Patent Application No. 202010897917.1 dated Apr. 20, 2024.
International Search Report and Written Opinion from PCT/CN2021/118908 dated Dec. 17, 2021.
Office Action from Japanese Patent Application No. 2022-516220 dated Aug. 21, 2024.
Genbank, AOZ48530.1 "Bevacizumab heavy chain", Nov. 1, 2016.
The First Office Action dated Jan. 3, 2024, directed to CN Application No. 202080064136.2.
Extended European Search Report dated Aug. 21, 2023, directed to EP Application No. 20863990.6; 7 pages.
Fang, T. et al., (Apr. 2019). "Remodeling of the Tumor Microenvironment by a Chemokine/Anti-PD-L1 Nanobody Fusion Protein," Molecular Pharmaceutics, vol. 16, No. 6; pp. 2838-2844.
Dougan, M. et al., (Apr. 2018). "Targeting Cytokine Theraphy to the Pancreatic Tumor Microenvironment Using PD-L1-Specific VHHs," Cancer Immunology Research, vol. 6, No. 4; pp. 389-401.

(Continued)

*Primary Examiner* — Daniel E Kolker
*Assistant Examiner* — James Ryland Melchior
(74) *Attorney, Agent, or Firm* — Neal, Gerber & Eisenberg LLP

(57) ABSTRACT

Provided is a complementary determining region (CDR) of a VHH chain of an anti-PD-L1 single-domain antibody, wherein the CDR of the VHH chain includes the following: CDR1 with an amino acid sequence as shown in SEQ ID NO:5n+1; CDR2 with an amino acid sequence as shown in SEQ ID NO:5n+2, or CDR2 with an amino acid sequence having an sequence identity of greater than 85% with a sequence as shown in SEQ ID NO:2; and CDR3 with an amino acid sequence as shown in SEQ ID NO: 5n+3; wherein, each n is independently 0, 1, 2, 3, 4, 5, 6, 7, 8, 9, 10, 11, 12, 13, 14 or 15.

10 Claims, 16 Drawing Sheets
Specification includes a Sequence Listing.

(56) References Cited

OTHER PUBLICATIONS

Ravi, R. et al., (Feb. 2018). "Bifunctional immune checkpoint-targeted antibody-ligand traps that simultaneously disable TGFβ enhance the efficacy of cancer immunotheraphy," Nature Communications, vol. 9, No. 741; pp. 1-14.
Knudson K.M. et al., (Feb. 2018). "M7824, a novel bifunctional anti-PD-L1/TGFβ Trap fusion protein, promotes anti-tumor efficacy as monotherapy and in combination with vaccine," Oncoimmunology, vo. 7, No. 5; pp. 1-14.
Guo, Y. et al., (Jun. 2022). "Phase I/IIa study of PM8001, a bifunctional fusion protein targeting PD-L1 and TGF-β, in patients with advanced tumors," retrieved from <https://ascopubs.org/doi/pdf/10.1200/J CO.2022.40.16_suppl.2512>.
International Search Report and Written Opinion mailed Jan. 15, 2021, directed to International Application No. PCT/IB2020/058303; 13 pages.
Zhang, F. et al., (Mar. 7, 2017). "Structural basis of a novel PD-L1 nanobody for immune checkpoint blockade," Cell Discovery located at <www.nature.com/celldisc>; 12 pages.
Feng P. et al., (2017). "Preparation and application of anti-human PD-L1 monoclonal antibodies," pp. 879-883.
Iezzi M. et al. (Feb. 19, 2018). "Single-Domain Antibodies and the Promise of Modular Targeting in Cancer Imaging and Treatment," Frontiers in Immunology, No. 9; 11 pages.
Lv, G. et al., (Jun. 28, 2019). "PET Imaging of Tumor PD-L1 Expression with a Highly Specific Nonblocking Single-Domain Antibody," Journal of Nuclear Medicine, vol. 61, No. 1; pp. 117-122.

FIG. 21

ANTI-PD-L1 SINGLE-DOMAIN ANTIBODY AND DERIVATIVES AND USE THEREOF

SEQUENCE LISTING

The instant application contains a Sequence Listing which has been filed electronically in ASCII format and is hereby incorporated by reference in its entirety. Said ASCII copy, created on Aug. 24, 2023, is named 141279_560303_SL.txt and is 69,632 bytes in size.

TECHNICAL FIELD

The present application relates to the technical fields of biomedicine or biopharmacy, and in particular to an anti-PD-L1 single-domain antibody and derivatives and use thereof.

BACKGROUND

Programmed death 1 ligand 1 (PD-L1), also known as CD274, is a member of the B7 family and a ligand for PD-1. PD-L1 is a type I transmembrane protein consisting a total of 290 amino acids, including one IgV-like region, one IgC-like region, one transmembrane hydrophobic region and one intracellular region composed of 30 amino acids.

PD-L1 has an effect of negatively regulating immune responses. It is found through studies that PD-L1 is mainly expressed in activated T cells, B cells, macrophages, dendritic cells, and the like. In addition to lymphocytes, PD-L1 is also expressed in endothelial cells of many other tissues such as the thymus, heart, placenta and the like, and various non-lymphoid systems such as melanoma, liver cancer, gastric cancer, renal cell carcinoma, ovarian cancer, colon cancer, breast cancer, esophageal cancer, head and neck cancer and the like. PD-L1 has certain versatility in regulating autoreactive T and B cells and immune tolerance, and plays a role in T and B cell response in peripheral tissues. The high expression of PD-L1 on tumor cells is related to the poor prognosis of cancer patients.

Programmed death-1 (PD-1) combined with PD-L1, also known as CD279, is a member of the B7-CD28 superfamily. The cytoplasmic region of CD279 contains two tyrosine residues, one near the N-terminal is located in an immunoreceptor tyrosine-based inhibitory motif (ITIM), and the other near the C-terminal is located in an immunoreceptor tyrosine-based switch motif (ITSM). PD-1 is mainly expressed on surfaces of activated T lymphocytes, B lymphocytes and macrophages. Under normal circumstances, PD-1 can inhibit the function of T lymphocytes and promote the function of Treg cells, thereby inhibiting autoimmune responses and preventing the occurrence of autoimmune diseases. However, in the development of tumors, the binding of PD-L1 expressed by tumor cells to PD-1 can promote the immune escape of tumors by inhibiting lymphocytes. The binding of PD-L1 to PD-1 may cause a variety of biological changes and immune regulation, such as inhibiting the proliferation and activation of lymphocytes, inhibiting the differentiation of CD4+ T cells into Th1 and Th17 cells and inhibiting the release of inflammatory cytokines.

The successful application of monoclonal antibodies in cancer diagnostics and targeted therapy has launched a revolution in tumor therapy. Traditional monoclonal antibodies (150kD) have a high molecular mass that may hinder their propensity to penetrate through tissues, resulting in low effective concentrations in tumors and insufficient therapeutic effects. In addition, long development periods, high production costs, insufficient stability and many other factors of traditional antibodies limit their clinical application and popularization.

Single-domain antibodies are currently the smallest antibody molecules, and the molecular weight (without Fc) is $1/10$ of that of ordinary antibodies. In addition to the antigen reactivity of monoclonal antibodies, single-domain antibodies also have unique functional characteristics, such as a low molecular weight, high stability, good solubility, easy expression, high tissue penetrability, simple humanization and low preparation costs, which may overcome the shortcomings of traditional antibodies.

However, there is still a lack of satisfactory single-domain antibodies against PD-L1 in the field. Therefore, there is an urgent need in this field to develop specific single-domain antibodies which are effective against PD-L1.

SUMMARY

The objective of the present application is to provide a class of specific single-domain antibodies which are effective against PD-L1.

In a first aspect of the present application, a complementarity determining region (CDR) of a VHH chain of an anti-PD-L1 single-domain antibody is provided. The CDR of the VHH chain consists of the following:
  CDR1 with an amino acid sequence as shown in SEQ ID NO: 5n+1;
  CDR2 with an amino acid sequence as shown in SEQ ID NO: 5n+2, or CDR2 with an amino acid sequence having an sequence identity of greater than 85% with a sequence as shown in SEQ ID NO: 2; and
  CDR3 with an amino acid sequence as shown in SEQ ID NO: 5n+3.

Each n is independently 0, 1, 2, 3, 4, 5, 6, 7, 8, 9, 10, 11, 12, 13, 14 or 15.

In another preferred embodiment, n is 0 or 1.

In another preferred embodiment, the amino acid sequence of CDR2 is shown in SEQ ID NO: 2, 7, 81, 84, 87, 90, 93, or 96.

In another preferred embodiment, CDR1, CDR2 and CDR3 are separated by framework regions FR1, FR2, FR3 and FR4 of the VHH chain.

In a second aspect of the present application, a VHH chain of an anti-PD-L1 single-domain antibody is provided. The VHH chain of the anti-PD-L1 single-domain antibody includes the CDR1, CDR2 and CDR3 according to the first aspect of the present application.

In another preferred embodiment, an amino acid sequence of the VHH chain of the anti-PD-L1 single-domain antibody is shown in SEQ ID NO: 5n+4, 82, 85, 88, 91, 94 or 97.

n is 0, 1, 2,3, 4, 5, 6, 7, 8, 9, 10, 11, 12, 13, 14 or 15.

Any one of the amino acid sequences above also includes a derivative sequence which is obtained through addition, deletion, modification and/or substitution of 1-8 (preferably 1-5, more preferably 1-3) amino acid residues and can retain a PD-L1 binding affinity of the anti-PD-L1 single-domain antibody.

In another preferred embodiment, n is 0 or 1.

In another preferred embodiment, the amino acid sequence of the VHH chain of the anti-PD-L1 single-domain antibody is shown in SEQ ID NO: 4, 9, 82, 85, 88, 91, 94 or 97.

In a third aspect of the present application, an anti-PD-L1 single-domain antibody is provided. The anti-PD-L1 single-domain antibody is a single-domain antibody against a PD-L1 epitope and has the VHH chain of the anti-PD-L1 single-domain antibody according to the second aspect of the present application.

In a fourth aspect of the present application, a polynucleotide is provided. The polynucleotide encodes a protein selected from the group of proteins including: the CDR region of the VHH chain of the anti-PD-L1 single-domain antibody according to the first aspect of the present application, the VHH chain of the anti-PD-L1 single-domain antibody according to the second aspect of the present application, or the anti-PD-L1 single-domain antibody according to the third aspect of the present application.

In another preferred embodiment, the polynucleotide has a nucleotide sequence as shown in SEQ ID NO: 5n, 83, 86, 89, 92, 95 or 98.

n is 1, 2,3, 4, 5, 6, 7, 8, 9, 10, 11, 12, 13, 14, 15 or 16.

In another preferred embodiment, the polynucleotide includes DNA or RNA.

In a fifth aspect of the present application, an expression vector is provided. The expression vector contains the polynucleotide according to the fourth aspect of the present application.

In another preferred embodiment, the expression vector also contains a nucleotide sequence encoding an Fc fragment of immunoglobulin.

In another preferred embodiment, the immunoglobulin is IgG1, IgG2, IgG3 or IgG4.

In a sixth aspect of the present application, a host cell is provided. The host cell contains the expression vector according to the fifth aspect of the present application, or a genome of the host cell is integrated with the polynucleotide according to the fourth aspect of the present application.

In another preferred embodiment, the host cell includes prokaryotic cells or eukaryotic cells.

In another preferred embodiment, the host cell is selected from the group of *Escherichia coli*, yeast cells and mammalian cells.

In a seventh aspect of the present application, a method of producing an anti-PD-L1 single-domain antibody is provided, which includes the steps of:
  (a) culturing the host cell according to the sixth aspect of the present application under conditions suitable for the production of single-domain antibodies, and thereby obtaining a culture containing the anti-PD-L1 single-domain antibody; and
  (b) isolating or recovering the anti-PD-L1 single-domain antibody from the culture.

In another preferred embodiment, the anti-PD-L1 single-domain antibody has an amino acid sequence as shown in SEQ ID NO: 5n+4, 82, 85, 88, 91, 94 or 97.

n is 0, 1, 2, 3, 4, 5, 6, 7, 8, 9, 10, 11, 12, 13, 14 or 15.

In an eighth aspect of the present application, a single-domain antibody fusion protein is provided. The single-domain antibody fusion protein has a structure as shown in formula I from N-terminal to C-terminal:

Z1-Z2-L-Z3      (Formula I)

In the formula,
  Z1 is the VHH chain of the anti-PD-L1 single-domain antibody according to the second aspect of the present application;
  Z2 is an Fc fragment of immunoglobulin;
  L is a linker sequence; and
  Z3 is an immunoregulatory molecule moiety.

In another preferred embodiment, the immunoglobulin is IgG1, IgG2, IgG3 or IgG4.

In another preferred embodiment, an amino acid sequence of Z2 is shown in SEQ ID NO: 99.

In another preferred embodiment, the amino acid sequence of Z2 is the same or substantially same as the amino acid sequence as shown in SEQ ID NO: 99.

In another preferred embodiment, L has an amino acid sequence selected from the group including GGGGS, $(GGGGS)_2$, $(GGGGS)_3$, $(GGGGS)_4$, $(GGGGS)_5$, or a combination thereof.

In another preferred embodiment, the amino acid sequence of L is shown in SEQ ID NO: 100.

In another preferred embodiment, the amino acid sequence of L is the same or substantially same as the amino acid sequence as shown in SEQ ID NO: 100.

In another preferred embodiment, the immunoregulatory molecule is a TGFβRII extracellular domain.

In another preferred embodiment, an amino acid sequence of Z3 is shown in SEQ ID NO: 101.

In another preferred embodiment, the amino acid sequence of Z3 is the same or substantially same as the amino acid sequence as shown in SEQ ID NO: 101.

In another preferred embodiment, the substantially same indicates that at most 50 (preferably 1-20, more preferably 1-10, more preferably 1-5, most preferably 1-3) amino acids are different, and the difference includes substitution, deletion or addition of amino acids.

In another preferred embodiment, the substantially same indicates that a sequence identity of an amino acid sequence and a corresponding amino acid sequence is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99%.

In another preferred embodiment, an amino acid sequence of the single-domain antibody fusion protein is shown in SEQ ID NO: 102.

In a ninth aspect of the present application, an immunoconjugate is provided. The immunoconjugate includes:
  (a) the VHH chain of the anti-PD-L1 single-domain antibody according to the second aspect of the present application, the anti-PD-L1 single-domain antibody according to the third aspect of the present application, or the single-domain antibody fusion protein according to the eighth aspect of the present application; and
  (b) a coupling moiety selected from the group including a detectable marker, a drug, a toxin, a cytokine, a radionuclide or an enzyme.

In another preferred embodiment, the coupling moiety is a drug or a toxin.

In another preferred embodiment, the coupling moiety is a detectable marker.

In another preferred embodiment, the conjugate is selected from a fluorescent or luminescent marker, a radioactive marker, a MRI (magnetic resonance imaging) or CT (electronic computer X-ray tomography) contrast agent, or an enzymes capable of producing a detectable product, a radionuclide, a biotoxin, a cytokine (such as IL-2 and similar), an antibody, an antibody Fc fragment, an antibody scFv fragment, a gold nanoparticle/nanorod, a viral particle, a liposome, a magnetic nanoparticle, a prodrug activating enzyme (such as DT-diaphorase (DTD) or biphenyl hydrolase-like protein (BPHL)), a chemotherapeutic agent (such as cisplatin) or any form of nanoparticle or similar.

In another preferred embodiment, the immunoconjugate contains a multivalent (such as bivalent) VHH chain of the anti-PD-L1 single-domain antibody according to the second aspect of the present application, the anti-PD-L1 single-domain antibody according to the third aspect of the present application, or the single-domain antibody fusion protein according to the eighth aspect of the present application.

In another preferred embodiment, the multivalent indicates that the amino acid sequence of the immunoconjugate contains multiple repeated VHH chains of the anti-PD-L1 single-domain antibody according to the second aspect of the present application, the anti-PD-L1 single-domain antibody according to the third aspect of the present application, or the single-domain antibody fusion protein according to the eighth aspect of the present application.

In a tenth aspect of the present application, use of the anti-PD-L1 single-domain antibody according to the third aspect of the present application or the single-domain antibody fusion protein according to the eighth aspect of the present application is provided, which is used in preparation of (a) reagents used for detecting PD-L1 molecules and (b) drugs used for treating tumors.

In another preferred embodiment, detection includes flow cytometry and cellular immunofluorescence detection.

In an eleventh aspect of the present application, a pharmaceutical composition is provided, which includes:
  (i) the CDR of the VHH chain of the anti-PD-L1 single-domain antibody according to the first aspect of the present application, the VHH chain of the anti-PD-L1 single-domain antibody according to the second aspect of the present application, the anti-PD-L1 single-domain antibody according to the third aspect of the present application, the single-domain antibody fusion protein according to the eighth aspect of the present application, or the immunoconjugate according to the ninth aspect of the present application; and
  (ii) a pharmaceutically acceptable carrier.

In another preferred embodiment, the pharmaceutical composition is in a form of injection.

In another preferred embodiment, the pharmaceutical composition is used for manufacturing a drug for treating tumor, and the tumor is selected from the group including gastric cancer, liver cancer, leukemia, kidney tumor, lung cancer, small intestinal carcinoma, bone cancer, prostate cancer, colorectal cancer, breast cancer, colon cancer, cervical cancer, lymphoma, adrenal gland tumor, bladder tumor, or a combination thereof.

In a twelfth aspect of the present application, one or more uses of the anti-PD-L1 single-domain antibody according to the third aspect of the present application or the single-domain antibody fusion protein according to the eighth aspect of the present application is provided:
  (i) for detection of a human PD-L1 molecule;
  (ii) for flow cytometry;
  (iii) for cellular immunofluorescence detection;
  (iv) for tumor treatment; and
  (v) for tumor diagnosis.

In another preferred embodiment, the use is non-diagnostic and non-therapeutic.

In a thirteenth aspect of the present application, a recombinant protein is provided. The recombinant protein includes:
  (i) a sequence of a heavy chain variable region VHH according to the second aspect of the present application, a sequence of the single-domain antibody according to the third aspect of the present application, or the single-domain antibody fusion protein according to the eighth aspect of the present application; and
  (ii) an optional tag sequence assisting expression and/or purification.

In another preferred embodiment, the tag sequence includes a 6His tag, an HA tag, a Flag tag, an Fc tag, an HSA or anti-HSA antibody or single-domain antibody, or a combination thereof.

In another preferred embodiment, the recombinant protein specifically binds to a PD-L1 protein.

In a fourteenth aspect of the present application, use of the VHH chain according to the second aspect of the present application, the single-domain antibody according to the third aspect of the present application, the single-domain antibody fusion protein according to the eighth aspect of the present application, or the immunoconjugate according to the ninth aspect of the present application is provided, which is used in manufacture of a medicament, a regent, a detection plate or a kit.

The reagent, the detection plate or the kit is used for detecting a PD-L1 protein in a sample.

The medicament is used for treating or preventing a tumor expressing the PD-L1 protein (namely PD-L1 positive).

In another preferred embodiment, the tumor includes gastric cancer, lymphoma, liver cancer, leukemia, kidney tumor, lung cancer, small intestinal carcinoma, bone cancer, prostate cancer, colorectal cancer, breast cancer, colon cancer, drenal gland tumor, or a combination thereof.

In a fifteenth aspect of the present application, a method for detecting a PD-L1 protein in a sample is provided, which includes the steps:
  (1) contacting the sample with the single-domain antibody according to the third aspect of the present application or the single-domain antibody fusion protein according to the eighth aspect of the present application; and
  (2) detecting whether an antigen-antibody complex is formed or not, wherein the formation of the complex indicates the presence of the PD-L1 protein in the sample.

In another preferred embodiment, detection includes qualitative detection and quantitative detection.

In a sixteenth aspect of the present application, a method for treating a disease is provided. The method includes administering the single-domain antibody according to the third aspect of the present application, the single-domain antibody fusion protein according to the eighth aspect of the present application, or the immunoconjugate according to the ninth aspect of the present application in an effective amount to a subject in need.

In another preferred embodiment, the subject includes a mammal.

In another preferred embodiment, the mammal is a human.

It should be understood that within the scope of the present application, the technical features of the present application above and the technical features specifically described below (such as embodiments) can be combined with each other to form a new or preferred technical solution. Due to space limitations, more contents are not repeated here.

BRIEF DESCRIPTION OF THE DRAWINGS

FIG. 21 shows pictures of tumors in different drug groups 28 days after inoculation.

DETAILED DESCRIPTION

Figure 1:
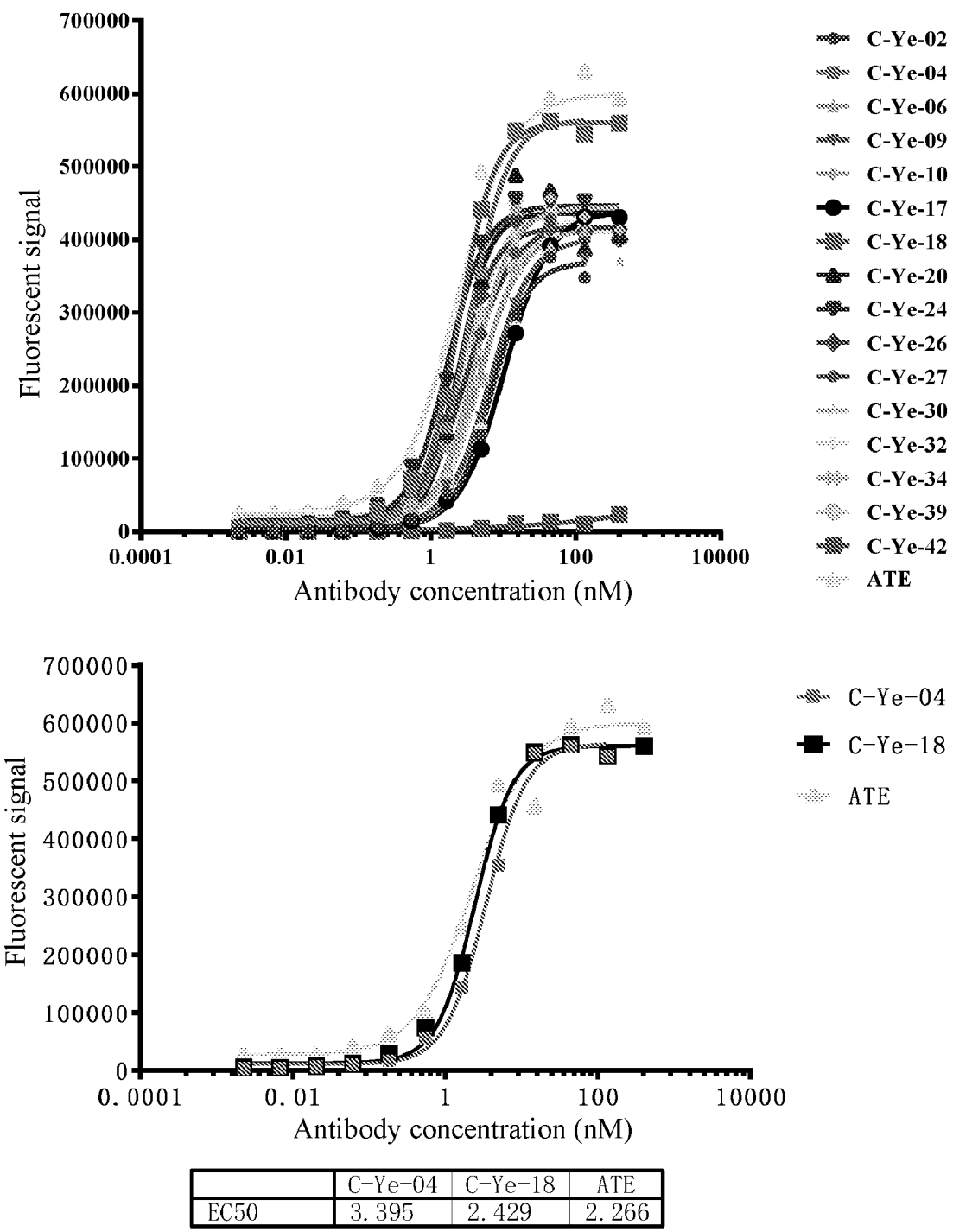
FIG. 1 shows that single-domain antibodies of the present application can bind to a human PD-L1 protein on a cell surface, and the binding effect of a portion of the antibodies is similar to that of a positive control.

After extensive and in-depth research and extensive screening, the inventors developed a class of anti-PD-L1 single-domain antibodies. Experimental results show that the PD-L1 single-domain antibody and mutant derivatives thereof obtained in the present application can effectively block the interaction between PD-L1 and PD-1, and have relatively good thermal stability.

Specifically, the present application used a human-derived PD-L1 antigen protein for immunizing llamas to obtain high-quality immune libraries containing single-domain antibody genetic sequences. The inventors screened for single-domain antibodies with genetic sequences showing relatively high humanization levels (sequence identity >85%) from the immune single-domain antibody gene library. PD-L1 protein molecules were subjected to biotinylation, and the immune library containing sequence of single-domain antibodies was screened using yeast display technology, and thus genes of the candidate single-domain antibodies specific to PD-L1 were obtained. Then the obtained genes and engineered mutants thereof were transferred into Expi-CHO cells and further screened in the aspects of antibody affinity, ability to block the binding of PD-L1 to PD-1, thermal stability and activation of T cell activity to obtain a class and panel of single-domain antibodies, which can be expressed efficiently in vitro with high binding specificity to human PD-L1 antigen.

In addition, experimental results show that a fusion protein produced by fusing a single-domain antibody sequence (as a targeting moiety) of the present application with an IgG1 Fc fragment (as a linking moiety) and a TGFβRII extracellular domain (as an immunoregulatory molecule moiety) is highly active with PD-L1, and can effectively block the interaction between PD-L1 and PD-1, effectively block the TGF-β/SMAD signal pathway, effectively activate human T lymphocytes and effectively inhibit tumor growth in mice.

In addition, experimental results show that the single-domain antibody of the present application can significantly inhibit the growth of subcutaneously transplanted tumors and reduce tumor weight in mice. The inhibitory effect on tumor growth at the same molar dosage is higher than that of similar molecules, anti-PD-L1 single domain antibodies and TGF-βRII-Fc fusion proteins and has no apparent toxicity to animal models of diseases.

On this basis, the present application has been completed.

Single-Domain Antibody of the Present Application

As used herein, the terms "single-domain antibody of the present application", "anti-PD-L1 single-domain antibody of the present application" and "PD-L1 single-domain antibody of the present application" are used interchangeably and all refer to single-domain antibodies with specificity in recognizing and binding to PD-L1 (including human PD-L1). Single-domain antibodies with an amino acid sequence of a VHH chain as shown in SEQ ID NO: 4, 9, 82, 85, 88, 91, 94 or 97 are particularly preferred.

As used herein, the term "antibody" or "immunoglobulin" is a heterotetrameric glycoprotein of about 150,000 daltons with the same structural characteristics, which consists of two identical light chains (L) and two identical heavy chains (H). Each light chain is linked to a heavy chain through a covalent disulfide bond, and the numbers of disulfide bonds between the heavy chains of different immunoglobulin isotypes are different. Each heavy chain and light chain also have regularly spaced intrachain disulfide bonds. Each heavy chain has a variable region (VH) at one end, followed by multiple constant regions. Each light chain has a variable region (VL) at one end and a constant region at the other end; the constant region of each light chain is relative to the first constant region of the corresponding heavy chain, and the variable region of each light chain is relative to the variable region of the corresponding heavy chain. Special amino acid residues form an interface between the variable regions of the light chain and the heavy chain.

As used herein, the terms "single domain antibody (VHH)" and "nanobody" have the same meaning, referring to cloning the variable region of the heavy chain of an antibody and constructing a single domain antibody (VHH) consisting of only one heavy chain variable region, and the single domain antibody is the smallest antigen-binding fragment with complete functions. Usually, after obtaining an antibody with naturally missing light chain and heavy chain constant region 1 (CH1), a variable region of a heavy chain of the antibody is cloned to construct a single domain antibody (VHH) consisting of only one heavy chain variable region.

As used herein, the term "variable" means that certain parts of the variable region of an antibody are different in sequence, so that the binding and specificity of various specific antibodies to specific antigens are formed. However, variability is not evenly distributed in the entire variable region of the antibody. Variability is concentrated in three fragments in the light chain and heavy chain variable regions known as CDRs or hypervariable regions. The more conserved part of the variable region is called a framework region (FR). The variable regions of the natural heavy chain and light chain each contain four FRs, which are roughly in a β-folded configuration and connected by three CDRs forming a connecting loop, and in some cases, a partial β folded structure can be formed. The CDRs in each chain are closely joined together by the FR and form an antigen binding site of an antibody together with the CDRs of another chain (see Kabat et al., NIH Publ. No. 91-3242, Volume I, pp. 647-669 (1991)). Constant regions are not directly involved in the binding of antibodies to antigens, but they exhibit different effector functions, such as participating in antibody-dependent cytotoxicity of the antibody.

As known by those skilled in the art, immunoconjugates and fusion expression products include conjugates formed by binding drugs, toxins, cytokines, radionuclides, enzymes and other diagnostic or therapeutic molecules to the antibody of the present application or fragments thereof. The present application also includes a cell surface marker or antigen bound to the anti-PD-L1 protein antibody or fragments thereof.

As used herein, the terms "heavy chain variable region" and "VH" are used interchangeably.

As used herein, the terms "variable region" and "complementarity determining region (CDR)" are used interchangeably.

In a preferred embodiment of the present application, the heavy chain variable region of an antibody includes CDRs being CDR1, CDR2 and CDR3.

In a preferred embodiment of the present application, the heavy chain of an antibody includes the above heavy chain variable region and heavy chain constant region.

In the present application, the terms "antibody of the present application", "protein of the present application", or "polypeptide of the present application" are used interchangeably and all refer to a polypeptide which specifically binds to the PD-L1 protein, such as a protein or polypeptide having a heavy chain variable region, which may or may not contain initiation methionine.

The present application also provides other proteins or fusion expression products having the antibody of the present application. Specifically, the present application includes any protein or protein conjugate and fusion expression product (namely immunoconjugate and fusion expression product) having a heavy chain containing a variable region, as long as the variable region is identical or at least 90% homologous, preferably at least 95% homologous to the heavy chain variable region of the antibody of the present application.

Generally, antigen-binding properties of an antibody can be described by three specific regions, called variable regions (CDR), located in the heavy chain variable region, separated by four framework regions (FR), and the amino acid sequences of the four FRs are relatively conservative and do not directly participate in a binding reaction. These CDRs form a circular structure and are close to each other in spatial structure due to the R folds formed by the FRs therebetween, and the CDRs on a heavy chain and the CDRs on a corresponding light chain constitute antigen binding sites of an antibody. The amino acid sequences of antibodies of the same type can be compared to determine which amino acids constitute the FR or CDR regions.

The variable regions of the heavy chains of the antibody of the present application are of particular interest, because at least some of the variable regions are involve binding to antigens. Therefore, the present application includes molecules which have the heavy chain variable regions of the antibody with CDRs, as long as the CDRs thereof have 90% homology or above (preferably 95% or above, most preferably 98% or above) with the CDRs identified here.

The present application includes not only intact antibodies, but also fusion proteins formed by fragments of immunologically active antibodies or antibodies and other sequences. Therefore, the present application also includes fragments, derivatives and analogs of the antibodies.

As used herein, the terms "fragment", "derivative" and "analog" refer to polypeptides which substantially retain the same biological function or activity as the antibodies of the present application. The polypeptide fragments, derivatives or analogs of the present application may be (i) a polypeptide in which one or more conservative or non-conservative amino acid residues (preferably conservative amino acid residues) are substituted, and such substituted amino acid residues may or may not be encoded by genetic codes, (ii) a polypeptide with substitution groups in one or more amino acid residues, (iii) a polypeptide formed by fusing a mature polypeptide to another compound (such as a compound which extends the half-life of polypeptides, such as polyethylene glycol), or (iv) a polypeptide formed by fusing an additional amino acid sequence to the polypeptide sequence (such as a leader sequence, a secretory sequence, a sequence used for purifying the polypeptide or proprotein sequence, or a fusion protein formed with the 6His tag). According to the teaching herein, these fragments, derivatives and analogs are within the scope well known to those skilled in the art.

The antibody of the present application refers to a polypeptide having PD-L1 protein binding activity and the CDRs above. The term also includes variant forms of polypeptides containing the CDRs above and having the same functions as the antibody of the present application. These variant forms include (but are not limited to) deletion, insertion and/or substitution of one or more (usually 1-50, preferably 1-30, more preferably 1-20, most preferably 1-10) amino acids and the addition of one or more (usually within 20, preferably within 10, and more preferably within 5) amino acids at the C-terminal and/or N-terminal. For example, in this field, when amino acids with same or similar properties are used for substitution, functions of a protein are usually not changed. For another example, the addition of one or more amino acids to the C-terminal and/or N-terminal usually does not change functions of a protein. The term also includes active fragments and active derivatives of the antibody of the present application.

The variant forms of the polypeptide include homologous sequences, conservative variants, allelic variants, natural mutants, induced mutants, DNA encoded proteins which can be hybridized with coding DNA of the antibody of the present application under high or low stringency conditions, and polypeptides or proteins obtained by using antiserum against the antibody of the present application.

The present application also provides other polypeptides, such as a fusion protein containing the single-domain antibody or fragments thereof. In addition to almost full-length polypeptides, the present application also includes fragments of the single-domain antibody of the present application. Generally, the fragments have at least about 50 consecutive amino acids of the antibody of the present application, preferably at least about 60 consecutive amino acids, more preferably at least about 80 consecutive amino acids, and most preferably at least about 100 consecutive amino acids.

In the present application, "conservative variants of the antibody of the present application" refer to polypeptides formed by substitution of at most 10, preferably at most 8, more preferably at most 5, and most preferably at most 3 amino acids with amino acids having same or similar properties in comparison with the amino acid sequence of the antibody of the present application. These conservative variant polypeptides are best produced through substitution of amino acids according to Table 1.

TABLE 1

| Initial residues | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present application also provides polynucleotide molecules encoding the antibody or fragments thereof or fusion protein thereof. The polynucleotides of the present application can be in the form of DNA or RNA. DNA forms include cDNA, genomic DNA or artificially synthetic DNA. DNA can be single-stranded or double-stranded. DNA can be coding strands or non-coding strands.

Polynucleotides encoding the mature polypeptides of the present application include coding sequences only encoding the mature polypeptides, coding sequences of the mature polypeptides and various additional coding sequences, and the coding sequences of the mature polypeptides (and optional additional coding sequences) as well as non-coding sequences.

The term "polynucleotides encoding polypeptides" may include a polynucleotide encoding the polypeptide, or a polynucleotide which also includes the additional coding and/or non-coding sequence.

The present application also relates to polynucleotides which are hybridized with the sequences above, and the identity between the two sequences is at least 50%, preferably at least 70%, and more preferably at least 80%. The present application particularly relates to polynucleotides which can be hybridized with the polynucleotides of the present application under stringent conditions. In the present application, "stringent conditions" refer to: (1) hybridization and elution at relatively low ionic strength and relatively high temperature, such as 0.2×SSC, 0.1% SDS and 60° C.; or (2) addition of a denaturing agent during hybridization, such as 50% (v/v) formamide, 0.1% calf serum/0.1% Ficoll, 42° C. or similar; or (3) hybridization occurring only when the identity between two sequences is at least 90% or above, and more preferably 95% or above. In addition, a polypeptide encoded by a hybridizable polynucleotide has the same biological function and activity as a mature polypeptide.

A full-length nucleotide sequence of the antibody of the present application or fragments thereof can usually be obtained by a PCR amplification method, a recombination method or an artificial synthesis method. A feasible method is using artificial synthesis method to synthesize relevant sequences, especially when the fragment length is short. Usually, a fragment with a very long sequence can be obtained by first synthesizing multiple small fragments and then linking the fragments. In addition, a coding sequence of a heavy chain and an expression tag (such as 6His) can be fused together to form a fusion protein.

Once relevant sequences are obtained, a recombination method can be used to obtain the relevant sequences in large quantities. The relevant sequences are usually cloned into a vector, then transferred into cells, and then isolated from proliferated host cells by a conventional method, so as to obtain the relevant sequences. Biomolecules (nucleic acids, proteins, or similar) involved in the present application include biomolecules which exist in an isolated form.

At present, DNA sequences encoding the protein (or fragments thereof, or derivatives thereof) of the present application can be obtained completely through chemical synthesis. The DNA sequences can then be introduced into various existing DNA molecules (such as vectors) and cells known in the art. In addition, mutation can also be introduced into the protein sequences of the present application through chemical synthesis.

The present application also relates to vectors containing the suitable DNA sequences and suitable promoters or control sequences. These vectors can be used to transform appropriate host cells to express proteins.

The host cells can be prokaryotic cells such as bacterial cells; or lower eukaryotic cells such as yeast cells; or higher eukaryotic cells such as mammalian cells. Representative examples include *Escherichia coli, Streptomyces*, bacterial cells of *Salmonella typhimurium*, fungal cells such as yeast, insect cells of *Drosophila* S2 or Sf9, animal cells of CHO, COS7 and 293 cells or similar.

Transformation of the host cells with recombinant DNA can be performed by conventional techniques well known to those skilled in the art. When the host cells are prokaryotes such as *Escherichia coli*, competent cells which can absorb DNA can be harvested after an exponential growth phase and treated with a $CaCl_2$) method, and the steps used are well known in the art. Another way is to use $MgCl_2$. If necessary, transformation can also be performed by an electroporation method. When the host cells are eukaryotes, the following DNA transfection methods can be selected: a calcium phosphate co-precipitation method, conventional mechanical methods such as microinjection, electroporation, liposome packaging or similar.

Obtained transformants can be cultured by conventional methods to express polypeptides encoded by genes of the present application. According to the used host cells, a culture medium used in culture can be selected from various conventional culture mediums. Culture is carried out under conditions suitable for the growth of the host cells. After the host cells have grown to an appropriate cell density, a selected promoter is induced by a suitable method (such as temperature conversion or chemical induction), and the cells are further cultured for a period of time.

The recombinant polypeptides in the method above can be expressed in cells or on cell membranes, or secreted out of the cells. If necessary, the recombinant proteins can be separated and purified through various separation methods according to the physical, chemical and other characteristics. These methods are well known to those skilled in the art. Examples of these methods include, but are not limited to conventional renaturation treatment, treatment with a protein precipitation agent (a salting out method), centrifugation, osmotic fungus breaking, ultra-treatment, ultra-centrifugation, molecular sieve chromatography (gel filtration), adsorption chromatography, ion exchange chromatography, high performance liquid chromatography (HPLC) and other various liquid chromatography techniques and combinations of these methods.

The antibody of the present application can be used alone and can be combined or coupled with detectable markers (for diagnostic purposes), therapeutic agents, PK (protein kinase) modified moieties or any combination of these substances.

Detectable markers for diagnostic purposes include, but are not limited to fluorescent or luminescent markers, radioactive markers, MRI (magnetic resonance imaging) or CT (electronic computer X-ray tomography) contrast agents, or enzymes capable of producing detectable products.

Therapeutic agents which can be combined or coupled with the antibody of the present application include, but are not limited to: 1. radionuclides; 2. biotoxins; 3. cytokines such as IL-2; 4. gold nanoparticles/nanorods; 5. virus particles; 6. liposomes; 7. magnetic nanoparticles; 8. prodrug activating enzymes (such as DT-diaphorase (DTD) or biphenyl hydrolase-like protein (BPHL)); 9. chemotherapeutics (such as cisplatin) or any form of nanoparticles or similar.

Fusion Protein of the Present Application

As described herein, the "fusion protein of the present application" refers to a bifunctional fusion protein having both the anti-PD-L1 single-domain antibody described in the first aspect of the present application and an immunoregulatory molecule moiety.

In the present application, a fusion protein is provided, and the single-domain antibody fusion protein has a structure as shown in formula I from N-terminal to C-terminal:

Z1-Z2-L-Z3          (Formula I)

In the formula,
Z1 is the VHH chain of the anti-PD-L1 single-domain antibody according to the second aspect of the present application;
Z2 is an Fc fragment of immunoglobulin;
L is a linker sequence; and
Z3 is an immunoregulatory molecule part.
Preferably, the immunoglobulin can be IgG1, IgG2, IgG3 or IgG4.

In a preferred embodiment, the immunoglobulin is IgG1, and the amino acid sequence of Z2 is shown in SEQ ID NO: 99. In other embodiments, the amino acid sequence of Z2 is the same or substantially same as the amino acid sequence as shown in SEQ ID NO: 99.

In the present application, L is a flexible amino acid linker. Preferably, L has an amino acid sequence selected from the group including GGGGS, $(GGGGS)_2$, $(GGGGS)_3$, $(GGGGS)_4$, $(GGGGS)_5$, or a combination thereof.

In a preferred embodiment, the amino acid sequence of L is shown in SEQ ID NO: 100. In other embodiments, the amino acid sequence of L is the same or substantially same as the amino acid sequence as shown in SEQ ID NO: 100.

In an embodiment of the present application, the immunoregulatory molecule is a TGFβRII extracellular domain. Preferably, the amino acid sequence of Z3 is shown in SEQ ID NO: 101. In other embodiments, the amino acid sequence of Z3 is the same or substantially same as the amino acid sequence as shown in SEQ ID NO: 101.

In the present application, the substantially same indicates that at most 50 (preferably 1-20, more preferably 1-10, more preferably 1-5, most preferably 1-3) amino acids are different, and the difference includes substitution, deletion or addition of amino acids.

Preferably, the substantially same indicates that the sequence identity of an amino acid sequence and a corresponding amino acid sequence is at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99%.

In a preferred embodiment, the amino acid sequence of a single-domain antibody fusion protein is shown in SEQ ID NO: 102.

TGFβ is a key inducer of Epithelial-mesenchymal-transition (EMT). At the same time, TGFβ has a strong immunosuppressive effect in a tumor microenvironment, and thus has an important regulatory effect on tumor development, metastasis and drug resistance.

Therefore, in an embodiment of the present application, a TGFβ receptor II is selected as an immunoregulatory molecule in the fusion protein. The fusion protein of the present application has the advantages of high dual target binding affinity and specificity, and thereby further enhancing the anti-tumor immune function.

Pharmaceutical Composition

The present application also provides a composition. Preferably, the composition is a pharmaceutical composition, which contains the antibody or active fragments thereof or fusion protein thereof and a pharmaceutically acceptable carrier. Generally, these substances can be formulated in a non-toxic, inert and pharmaceutically acceptable aqueous carrier medium, wherein the pH is usually about 5-8, preferably about 6-8, although the pH can be changed according to properties of the formulated substances and disease conditions to be treated. The formulated pharmaceutical composition can be administered by conventional routes, including (but not limited to) intratumoral administration, intraperitoneal administration, intravenous administration, or topical administration.

The pharmaceutical composition of the present application can be directly used to bind PD-L1 protein molecules, and thus can be used to treat tumors. In addition, other therapeutic agents can also be used at the same time.

The pharmaceutical composition of the present application contains a safe and effective amount (such as 0.001-99 wt %, preferably 0.01-90 wt %, more preferably 0.1-80 wt %) of the single-domain antibody (or a conjugate thereof) of the present application and a pharmaceutically acceptable carrier or excipient. Such carrier includes (but is not limited to) saline, buffer, glucose, water, glycerol, ethanol and combinations thereof. A pharmaceutical preparation should be matched with the administration mode. The pharmaceutical composition of the present application can be prepared into an injection form, for example, the pharmaceutical composition is prepared by conventional methods with physiological saline or an aqueous solution containing glucose and other adjuvants. The pharmaceutical composition such as an injection and a solution should be manufactured under sterile conditions. The dosage of active ingredients is a therapeutically effective amount, such as about 10 g/kg body weight to about 50 mg/kg body weight per day. In addition, the polypeptides of the present application can also be used with other therapeutic agents.

When the pharmaceutical composition is used, a safe and effective amount of the immunoconjugate is administered to a mammal, wherein the safe and effective amount is usually at least about 10 g/kg body weight, and in most cases not higher than about 50 mg/kg body weight. Preferably, the dosage is about 10 g/kg body weight to about 10 mg/kg body weight. Of course, factors such as the administration route and the health conditions of patients should also be considered for the specific dosage, which are within the skill range of a skilled physician.

Labelled Single-Domain Antibody

In a preferred embodiment of the present application, the single-domain antibody contains a detectable marker. More preferably, the marker is selected from the following group of isotopes, colloidal gold markers, colored markers or fluorescent markers.

Colloidal gold labelling can be performed by methods known to those skilled in the art. In a preferred solution of the present application, the anti-PD-L1 single-domain antibody is labelled with colloidal gold to obtain a colloidal gold labelled single-domain antibody.

The anti-PD-L1 single-domain antibody of the present application has high specificity and titer.

Detection Method

The present application also relates to a method for detecting a PD-L1 protein. Steps of the method are generally as follows: obtaining a cell and/or tissue sample; dissolving the sample in a medium; and detecting the level of the PD-L1 protein in the dissolved sample.

In the detection method of the present application, the sample used is not particularly limited, and a representative example is a sample containing cells in a cell preservation solution.

Kit

The present application also provides a kit containing the antibody (or fragments thereof) of the present application or detection plates. In a preferred embodiment of the present application, the kit further includes a container, an instruction for use, a buffer agent or similar.

The present application also provides a detection kit for detecting the level of PD-L1. The kit includes an antibody for identifying the PD-L1 protein, a lysis medium for dissolving a sample and general reagents and buffers required for detection, such as various buffers, detection markers, detection substrates, or similar. The detection kit may be an in-vitro diagnostic device.

Use

As described above, the single-domain antibody of the present application has high values in biological use and clinical use, and use of the single-domain antibody relates to the fields of diagnosis and treatment of PD-L1 related diseases, basic medical research, biological research, or similar. Preferred use is for clinical diagnosis and targeted therapy for PD-L1.

The main advantages of the present application include:
1) The single-domain antibody of the present application is highly specific to human PD-L1 protein with a correct spatial structure.
2) The single-domain antibody of the present application has high affinity.
3) The single-domain antibody of the present application is easy to produce.
4) The single-domain antibody can inhibit a PD-1/PD-L1 pathway on the basis of TGF-β in a targeting and tumor microenvironment, restore T cells activity, enhance immune response and more effectively improve the effect of inhibiting tumor occurrence and development.
5) The single-domain antibody of the present application has no apparent toxicity.

The present application will be further described below in conjunction with working examples. It should be understood that these working examples are only used to illustrate the present application and not to limit the scope of the present application. Experimental methods without specific conditions in the following working examples are usually carried out according to conventional conditions, such as conditions in Sambrook et al., Molecular Cloning: Laboratory Manual (New York: Cold Spring Harbor Laboratory Press, 1989), or conditions recommended by manufacturers. Unless otherwise specified, percentages and parts are weight percentages and parts by weight.

Example 1: Construction of a Single-Domain Antibody Library

Animal Immunity 1 mg of a human PD-L1 antigen and a Freund's adjuvant were mixed in equal volumes for immunizing two llamas once a week with a total of 4 times to stimulate B cells to express antigen-specific single-domain antibodies. After four times of immunization, 50 ml of llama peripheral blood was extracted and separated with a lymphocyte separation solution to obtain lymphocytes. An RNA extraction reagent Trizol (purchased from Invitrogen) was used to extract total RNA. A cDNA synthesis kit (purchased from Invitrogen) was used for reverse transcription to obtain total llama cDNA.

Single-Domain Antibody Gene Amplification

In a first round of PCR, IgG2 and IgG3 sequences were amplified from cDNA:

TABLE 1

Primers for the first round of PCR

| Name | Sequence (5' to 3') | SEQ ID |
|---|---|---|
| Upstream primer | GTCCTGGCTGCTCTTCTACAAGG | 103 |
| Downstream primer | GGTACGTGCTGTTGAACTGTTCC | 104 |

Products of the first round of PCR were subjected to agarose gel electrophoresis, and fragments at 750 bp were recovered after gel cutting and used for a second round of VHH sequence amplification. Primers for the second round of PCR amplification were as follows:

TABLE 2

Primers for the second round of PCR

| Name | Sequence (5' to 3') | SEQ ID |
|---|---|---|
| Upstream primer | CTAGTGCGGCCGCcTGGAGACGGTGACCTGGGT | 105 |
| Downstream primer | CGCGGATCCCAGGTGCAGCTGCAGGAGTCTGGRGGAGG | 106 |

Products of the second round of PCR were used as templates for a third round of PCR, homologous arms were added to a VHH gene, and primers for the third round of PCR amplification were as follows:

TABLE 3

Primers for the third round of PCR

| Name | Sequence (5' to 3') | SEQ ID |
|---|---|---|
| Upstream primer | ATTTTTACTGCTGTTTTATTCGCAGCATCCTCCGCATTAGCTAAAAGAGAGGCTGAAGCACAGGTGCAGCTGCAGGAGTCTGGRGGAGG | 107 |
| Downstream primer | AGTTGTCAGTTCCTGTGCCCCCCCTCCTCCCGCGCCACCTCCGCCCGCACCTCCGCCACCACTGGAGACGGTGACCTGGGT | 108 |

The target fragments were recovered by using a PCR purification kit (purchased from QIAGEN).

Library Construction

A linearized yeast display vector and products of the third round of PCR were mixed and electrotransformed into Saccharomyces cerevisiae (ATCC® 20828) to construct an anti-PD-L1 single-domain antibody library from two animals, and the library size was measured to be 4.47×10$^7$ and 4.14×10$^7$.

Example 2: Screening of a PD-L1 Single-Domain Antibody

Biotinylation of Human PD-L1 Protein

A human PD-L1 protein was dissolved in an appropriate volume of double-distilled water, and a biotin was dissolved and mixed with the protein solution according to a product instruction of a biotin labelling kit (purchased from Thermo) and then incubated at 4° C. for 2 hours. A desalting column (purchased from Thermo) was used to remove excess biotin, and pretreatment by the desalting column and collection operation of a sample were both carried out according to steps in the product instruction.

Macs Enrichment of Yeasts which Specifically Bind to PD-L1

A VHH library constructed in Example 2 was inoculated into an SD-CAA amplification culture medium (1 L of SD-CAA amplification culture medium contained 6.7 g of YNB, 5 g of casamino acids, 13.62 g of Na$_2$HPO$_4$·12H$_2$O, 7.44 g of NaH$_2$PO$_4$ and 2% of glucose), the number of inoculated yeast cells was greater than ten times the library capacity (initial amplification concentration was 0.5 OD600/ml), and culture was carried out overnight at 30° C. and 225 rpm. Ten times the library capacity of the yeast cells were taken and centrifuged at 3000 rpm for 5 minutes (the following centrifugation operations were the same) to remove the culture medium, the yeast cells were resuspended with an SD-CAA induction culture medium, the initial concentration was adjusted to be 0.5 OD600/ml, and induction was carried out overnight. The concentration of the library after induction was measured, and ten times the library capacity of the yeast cells were taken and centrifuged to remove the culture medium. The yeast cells were resuspended with 50 ml of a washing buffer (PBS+0.5% BSA+2 mM EDTA) and centrifuged to remove the supernatant. The yeast cells were resuspended with 10 ml of the washing buffer.

A biotin-labelled PD-L1 protein (final concentration 100 mM) was added, incubated at room temperature for 30 minutes and centrifuged, and the yeast cells were collected and washed 3 times with 50 ml of the washing buffer. The yeast cells were resuspended with 5 ml of the washing buffer, 200 µl of SA magnetic beads (purchased from Miltenyi) were added, and the cells were incubated upside down for 10 minutes. A mixture of the yeast and magnetic beads was washed 3 times with the washing buffer and then added into an LS column (purchased from Miltenyi). The LS column was placed on a magnetic stand and washed with the washing buffer to remove non-specifically bound yeast cells. The column was removed from the magnetic stand, and the washing buffer was added to elute the yeast. The eluted yeast was centrifuged and transferred into a 200 ml SD-CAA amplification culture medium for amplification.

Florescence-Activated Cell Sorting to Obtain High-Affinity Yeast Cells

The yeast cells enriched by MACS were inoculated into an SD-CAA amplification culture medium, and the initial amplification concentration was 0.5 OD600/ml. Shake flask culture was carried out overnight at 30° C. and 225 rpm. The yeast cell were resuspended with an SD-CAA induction culture medium (1 L of SD-CAA induction culture medium contains 6.7 g of YNB, 5 g of casamino acids, 13.62 g of Na$_2$HPO$_4$·12H$_2$0, 7.44 g of NaH$_2$PO$_4$, 2% of galactose, 2% of raffinose and 0.1% of glucose), the initial concentration was 0.5 OD600/ml, and induction was carried out overnight. An anti-c-Myc mouse-derived antibody (purchased from Thermo) diluted by 1:200 and 100 nM of biotin-labelled PD-L1 antigen were added and incubated at room temperature for 10 minutes. The yeast was washed 3 times with PBS, a goat anti-mouse IgG (H+L) Alexa Fluor Plus 488 (purchased from Invitrogen) diluted by 1:500 and a streptavidin APC-conjugated fluorescent antibody (purchased from Invitrogen) were added and incubated in the dark at 4° C. for 15 minutes. 2 ml of PBS was added to resuspend the cells, and a BD FACSAriaIII instrument was used for sorting to obtain yeast which has high binding affinity to PD-L1 antigen.

Obtaining Genetic Sequences of PD-L1 Single-Domain Antibody Candidates

Yeast liquid with high binding ability to the PD-L1 antigen, which was obtained by MACS and FACS enrichment, was cultured overnight in an SD-CAA amplification culture medium at 30° C. and 225 rpm. Yeast plasmids were extracted according to operations of a yeast plasmid extraction kit (purchased from TIANGEN). The plasmids were transformed into Top10 competent cells (purchased from TIANGEN) by electrotransfer, coated on an ampicillin resistant flat plate and cultured overnight at 37° C. Single clones were taken for sequencing to obtain a VHH gene sequence.

Example 3: Construction, Expression and Purification of a Heavy Chain Antibody

Construction of an antibody gene into a pCDNA3.1 expression vector A VHH gene sequence was linked to a human IgG1 (LALA mutation) Fc fragment and digested into a linearized pCDNA3.1 vector by using a homologous recombinase (purchased from Vazyme) and an EcoR I/Not I enzyme, and the process was carried out in accordance with a product instruction. A homologous recombination product was transformed into Top10 competent cells, coated on an ampicillin resistant flat plate and cultured overnight at 37° C., and single clones were taken for sequencing.

Cell Transfection

An ExpiCHO™ expression system kit (purchased from Thermo) was used for transferring plasmids into Expi-CHO cells, and a transfection method was in accordance with a product instruction; after the cells were cultured for 5 days, the supernatant was collected, and protein A magnetic beads (purchased from GenScript) were used for purifying the target protein according to a sorting method. The magnetic beads were resuspended with an appropriate volume of binding buffer (PBS+0.1% Tween 20, pH 7.4) (1-4 times the volume of magnetic beads) and then added into a sample to be purified, and the mixture was incubated at room temperature for 1 hour and gently shaken during the period. The sample was placed on a magnetic stand (purchased from Beaver), the supernatant was removed, and the magnetic beads were washed 3 times with the binding buffer. 3-5 times the volume of the magnetic beads of an elution buffer (0.1M sodium citrate, pH 3.2) was added for shaking at room temperature for 5-10 minutes, the mixture was placed back on the magnetic stand, and the elution buffer was collected and transferred into a collection tube with an added neutralization buffer (1M Tris, pH 8.54) and mixed uniformly.

Example 4: Binding of a Purified Anti-PD-L1 Antibody to Human PD-L1

A pCHO1.0 vector (purchased from Invitrogen) of human PD-L1 cDNA (purchased from Sino Biological) was cloned into MCS through transfection to produce CHO cells (CHO-hPD-L1 cells) overexpressing human PD-L1. The cell density of the CHO-hPD-L1 cells subjected to enlarge cultivation was adjusted to $2\times10^6$ cells/ml, and 100 µl of the cells were added into each well of a 96-well flow plate and centrifuged for later use. A purified PD-L1 antibody was diluted with PBS, three times dilution was started for a total of 12 points when the concentration was 400 nM, and 100 µl of the diluted sample was added into each well of the 96-well flow plate with cells, incubated at 4° C. for 30 minutes and washed twice with PBS. 100 µl of goat F(ab')₂ anti-human IgG-Fc (PE) (purchased from Abcam) diluted 100 times with PBS was added into each well, incubated at 4° C. for 30 minutes and washed twice with PBS. 100 µl of PBS was added into each well for resuspending the cells, detection was carried out on a CytoFlex (Bechman) flow cytometer, and corresponding MFI was calculated.

In a measuring experiment according to the method above, experimental results are shown in FIG. 1, all the purified samples of the present application and the CHO-hPD-L1 cells have binding activity, and the binding activity of some purified samples was similar to that of a control antibody TECENTRIQ® (atezolizumab) (ATE; recorded in US20130034559, also known as 243.55.370).

Example 5: Affinity Measurement of a PD-L1 Antibody

ForteBlio affinity measurement was performed in accordance with an existing method (Estep, P et al., solution-based measurement of high-throughput antibody-antigen affinity and epitope classification, MAbs, 2013.5(2): p. 270-8). In short, a sensor was equilibrated offline in an analysis buffer for 30 minutes and then tested online for 60 seconds to establish a baseline, and a purified antibody obtained as described above was loaded online onto an AHQ sensor. Then the sensor was placed in a 100 nM PD-L1 antigen for reaction for 5 minutes and then transferred into PBS for dissociation for 5 minutes. A 1:1 combination model was used for dynamic analysis.

TABLE 4

Affinities of candidate molecules

| Number | SEQ ID | KD(M) | Kon(1/Ms) | Koff(1/s) |
|---|---|---|---|---|
| C-Ye-02 | 14 | 7.98E−08 | 4.69E+04 | 3.75E−03 |
| C-Ye-04 | 9 | 4.89E−09 | 1.03E+05 | 5.05E−04 |
| C-Ye-06 | 19 | 1.34E−07 | 4.35E+04 | 5.81E−03 |
| C-Ye-17 | 34 | 3.96E−07 | 2.58E+04 | 1.02E−02 |
| C-Ye-18 | 4 | 5.39E−09 | 8.33E+04 | 4.49E−04 |
| C-Ye-20 | 39 | 4.86E−08 | 9.06E+04 | 4.40E−03 |
| C-Ye-24 | 44 | 1.95E−08 | 7.71E+04 | 1.51E−03 |
| C-Ye-26 | 49 | 3.41E−08 | 9.41E+04 | 3.21E−03 |
| C-Ye-27 | 54 | 5.79E−08 | 5.45E+04 | 3.15E−03 |
| C-Ye-30 | 59 | 3.94E−08 | 5.32E+04 | 2.10E−03 |
| C-Ye-32 | 64 | 4.43E−08 | 5.83E+04 | 2.58E−03 |
| C-Ye-34 | 69 | 2.44E−08 | 7.81E+04 | 1.91E−03 |
| C-Ye-39 | 74 | 5.03E−07 | 2.12E+04 | 1.07E−02 |
| C-Ye-42 | 79 | 3.89E−08 | 5.70E+04 | 2.22E−03 |

Example 6: Gene Modification of a PD-L1 Antibody

In order to remove potential glycosylation sites in C-Ye-18, a CDRH2 portion of an amino acid sequence of C-Ye-18 was point-mutated into 6 forms in Table 5:

TABLE 5

Mutant sequences of C-Ye-18 CDR region

| Number | SEQ ID | CDRH2 region |
|---|---|---|
| C-Ye-18 | 2 | SINSSSSSTYYRDSVKG |
| C-Ye-18-1 | 81 | SINSGSSSTYYRDSVKG |
| C-Ye-18-2 | 84 | SISSSSSSTYYRDSVKG |
| C-Ye-18-3 | 87 | SIGSSSSTYYRDSVKG |
| C-Ye-18-4 | 90 | SIYSGSSSTYYRDSVKG |
| C-Ye-18-5 | 93 | SINSDSSSTYYRDSVKG |
| C-Ye-18-6 | 96 | SINSGSSSTYYRDSVKG |

In this study, IMGT (http://www.imgt.org) was used to evaluate the humanization level of mutant sequences of C-Ye-18 CDR regions, results are shown in Table 6, the humanization level of all C-Ye-18 mutants was higher than 8700, and the requirements of later drug development are met.

TABLE 6

Homology of mutant sequences of C-Ye-18 CDR regions and human

| Number | Germline | Homology |
|---|---|---|
| C-Ye-18 | IGHV3-74*01 | 87.80% |
| C-Ye-18-1 | IGHV3-74*01 | 88.80% |
| C-Ye-18-2 | IGHV3-74*01 | 87.80% |
| C-Ye-18-3 | IGHV3-74*01 | 87.80% |
| C-Ye-18-4 | IGHV3-74*01 | 87.80% |
| C-Ye-18-5 | IGHV3-74*01 | 87.80% |
| C-Ye-18-6 | IGHV3-74*01 | 87.80% |

A protein construction and expression purification method was the same as that in Example 3, and the purity of an obtained protein was detected by HIPLC. According to the HIPLC method, the mobile phase was 150 mM $Na_2HPO_4 \cdot 12H_2O$, and the pH was 7.0. Chromatographic conditions: detection wavelength 280 nm, column temperature 25° C., flow rate 0.35 ml/min, detection time 20 minutes, and a Zenix-C SEC-300 chromatographic column (SEPAX 4.6× 300 mm, 3 m).

TABLE 7

Purity detection results of C-Ye-10 mutant antibodies

| Number | Monomer ratio (%) |
|---|---|
| C-Ye-18 | 90.70 |
| C-Ye-18-1 | 97.40 |
| C-Ye-18-2 | 96.40 |
| C-Ye-18-3 | 98.50 |
| C-Ye-18-4 | 73.70 |
| C-Ye-18-5 | 83.00 |
| C-Ye-18-6 | 95.80 |

Example 7: Binding of C-Ye-18 Mutant Samples to Human PD-L1

Figure 2:
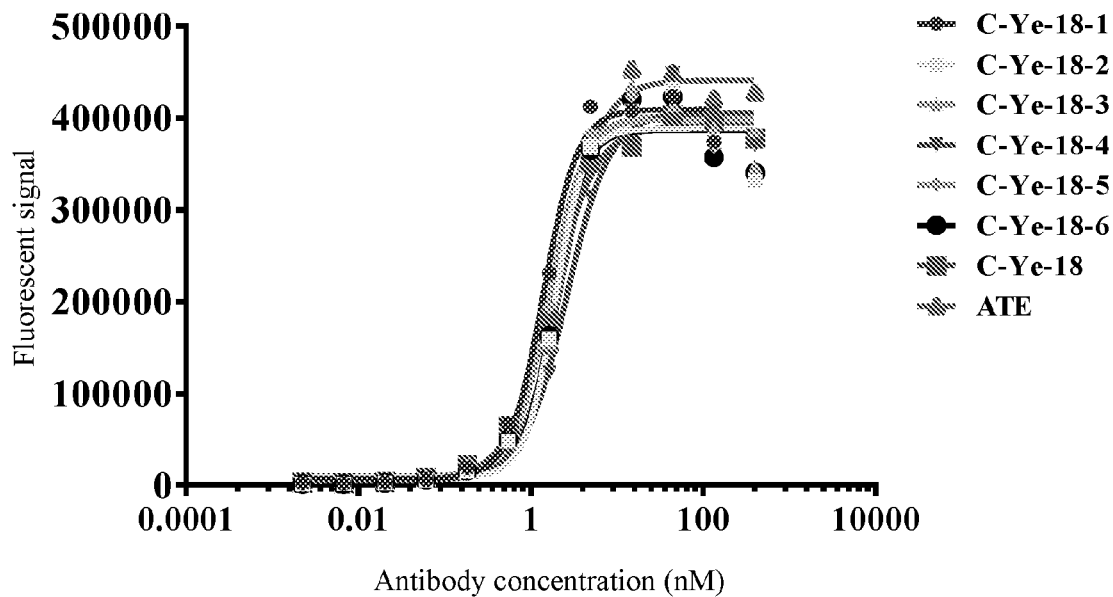
FIG. 2 shows that modified single-domain antibodies can still bind to the human PD-L1 protein on the cell surface, and the binding effect of the antibodies is similar to that of a positive control.

This experiment detected the binding activity of the purified C-Ye-18 mutant samples and CHO-hPD-L1 cells. The experimental method was the same as that in Example 4. Experimental results are in FIG. 2. The C-Ye-18 mutant samples and CHO-hPD-L1 cells have good binding activity, and the level was comparable to that of C-Ye-18 and a control antibody ATE.

Example 8: Affinity Measurement of C-Ye-18 Mutant Samples

This experiment detected the binding affinity of the purified C-Ye-18 mutant samples and human PD-L1. The experimental method was the same as that in Example 5. Experimental results are shown in Table 8. The C-Ye-18 mutant samples have very good binding activity with the human PD-L1 protein.

TABLE 8

Affinity of C-Ye-18 mutant samples

| Number | KD(M) | kon(1/Ms) | kdis(1/s) |
|---|---|---|---|
| C-Ye-18-1 | 4.13E−09 | 2.46E+05 | 1.02E−03 |
| C-Ye-18-2 | 5.41E−09 | 2.34E+05 | 1.27E−03 |
| C-Ye-18-3 | 7.03E−09 | 2.41E+05 | 1.70E−03 |
| C-Ye-18-4 | 6.40E−09 | 2.41E+05 | 1.54E−03 |
| C-Ye-18-5 | 4.08E−09 | 2.72E+05 | 1.11E−03 |
| C-Ye-18-6 | 6.00E−09 | 2.32E+05 | 1.39E−03 |

Example 9: Blocking of Binding of PD-L1 to PD-1 by C-Ye-18 Mutant Samples

A pCHO1.0 vector (purchased from Invitrogen) of human PD-L1 cDNA (purchased from Sino Biological) was cloned into MCS through transfection to produce CHO cells (CHO-hPD-1 cells) overexpressing human PD-L1. The cell density of the CHO-hPD-1 cells subjected to enlarge cultivation was adjusted to $2 \times 10^6$ cells/ml, and 100 μl of the cells were added into each well of a 96-well flow plate and centrifuged for later use. Purified mutant samples were diluted with PBS, three times dilution was started for a total of 12 points when the concentration was 400 nM, 60 μl of a diluted sample was added into each well of a 96-well sample dilution plate, 60 μl of biotinylated human PD-L1 protein (purchased from AcroBiosystems) was added into each well at the same time, the final concentration was 500 ng/ml, and the mutant samples were incubated at 4° C. for 30 minutes. 100 μl of a co-incubation sample was added into each well of the 96-well flow plate with cells, incubated at 4° C. for 30 minutes and washed twice with PBS. 100 μl of a Streptavidin, R-Phycoerythrin Conjugate (purchased from Thermo Fisher) diluted 100 times with PBS was added into each well, incubated at 4° C. for 30 minutes and washed twice with PBS. 100 μl of PBS was added into each well for resuspending the cells, detection was carried out on a CytoFlex (Beckman) flow cytometer, and corresponding MFI was calculated.

Figure 3:
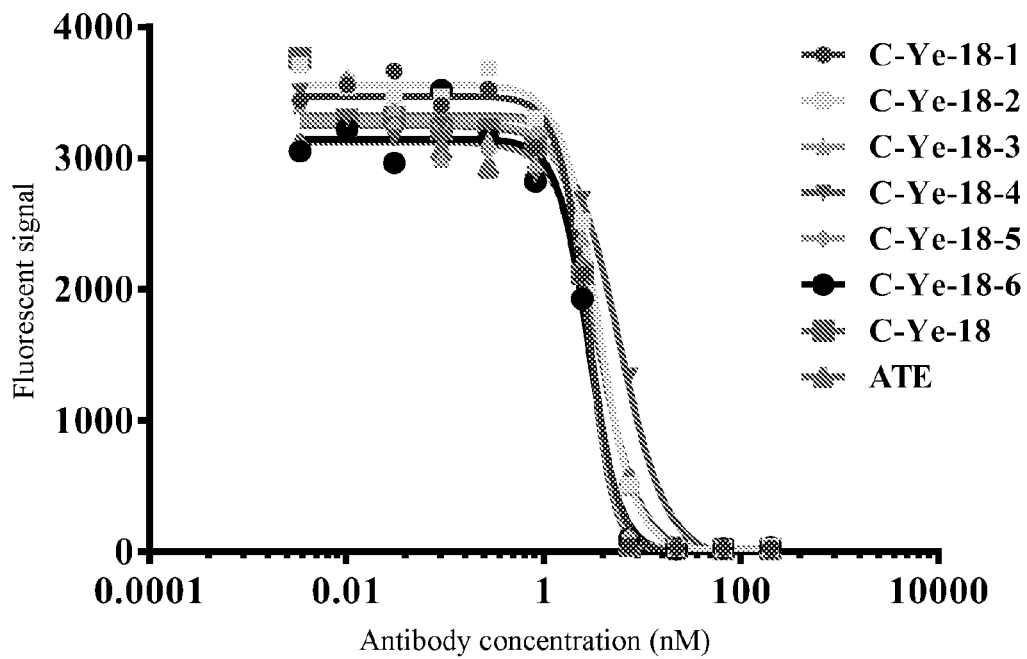
FIG. 3 shows that modified single-domain antibodies can still block the binding of the PD-L1 protein to the human PD-1 protein on the cell surface, and the blocking effect of the antibodies is similar to that of a positive control.

In a measuring experiment according to the method above, experimental results are shown in FIG. 3, all the mutant samples of the present application can block the binding of PD-L1 to PD-1, and the blocking level was comparable to that of C-Ye-18 and a control antibody ATE.

Example 10: Thermal Stability of C-Ye-18 Mutant Samples

DSC (Differential scanning calorimetry) was used to detect the thermal stability of different antibodies. The samples were concentrated and then diluted with PBS to 1 mg/ml, and a 5000× fluorescent color developing agent Cypro Orange (purchased from Bio-Rad) was diluted 50 times with ultrapure water to obtain a 100× fluorescent color developing agent Sypro Orange. 50 μl of each 1 mg/ml sample was taken, 10 μl of the 100× fluorescent color developing agent Sypro Orange and 40 μl of ultrapure water were added and mixed uniformly, 30 μl of each was add into a 96-well PCR plate, and each sample was added into three replicated wells and placed into a PCR instrument. A temperature-raising program was set as follows: the constant temperature of 25° C. was hold for 5 minutes, and the temperature was raised to 99° C. at a speed of 0.5° C./min. After the program ends, the temperature values of the lowest points of curves in a "Melt Curve" diagram were read, namely the Tm value of the sample. Specific results are shown in the following Table 9.

TABLE 9

Tm values of C-Ye-18 mutants

| Number | Tm1(° C.) | Tm2(° C.) | Tm3(° C.) |
|---|---|---|---|
| C-Ye-18 | 53.5 | 67.5 | 82 |
| C-Ye-18-1 | 60 | 67.5 | 82 |
| C-Ye-18-2 | 62.5 | 67.5 | 82 |
| C-Ye-18-3 | 58 | 67 | 82 |
| C-Ye-18-4 | 48 | 66 | 82 |
| C-Ye-18-5 | 66 | 66-67 | 82.5 |
| C-Ye-18-6 | 63 | 67.5 | 82 |

Example 11: a Mixed Lymphocyte Reaction Experiment

In the present Example, a mixed lymphocyte reaction experiment (MLR) was used to detect the activity of C-Ye-18 mutant samples to activate T cells. A specific experimental method was as follows.

PBMC cells (purchased from SAILY BIO, SLB-HPB) were resuscitated, centrifuged, resuspended with 10 ml of an X-VIVO-15 culture medium (purchased from LONZA) and subjected to adherent culture in a cell incubator at 37° C. for 2 hours, and nonadherent cells were removed. 10 ml of a DC culture medium was added, 10 ng/ml GM-CSF (purchased from R&D) and 20 ng/ml IL-4 were added into an X-VIVO-15 culture medium for culture for 3 days, 5 ml of the DC culture medium was added, the cells were continuously cultured for 6 days, a DC mature culture medium was added, 1000 U/ml TNF-α (purchased from R&D), 10 ng/ml IL-6 (purchased from R&D), 5 ng/ml IL-10 (purchased from R&D) and 1 µM PGE2 (purchased from Tocris) were added into the X-VIVO-15 culture medium, the cells were cultured for 2 days, mature DC cells were collected, and the cell density was adjusted to be $2 \times 10^5$ cells/ml with the X-VIVO-15 culture medium.

PBMC cells (purchased from SAILY BIO, SLB-HPB) from another donor were thawed, centrifuged and resuspended with 10 ml of the X-VIVO-15 culture medium. CD4$^+$ T cells were enriched with a CD4$^+$ T cell sorting kit (purchased from Stemcell) and resuspended with X-VIVO-15, the cell density was adjusted to be $2 \times 10^6$ cells/ml, the CD4$^+$ T cells were mixed with the collected mature DC cells at a ratio of 1:1, and 100 µl of a mixture was added into each well of a 96-well U-shaped bottom plate.

The C-Ye-18 mutant samples were diluted with the X-VIVO-15 culture medium, three times dilution was started for a total of 9 points when the concentration was 200 nM, 100 µl of the mixed cells were added into each well and cultured for 5 days, the supernatant was collected, and an ELISA (purchased from eBioscience) method was used to detect the expression amount of IFN-γ and IL2.

Figure 4:
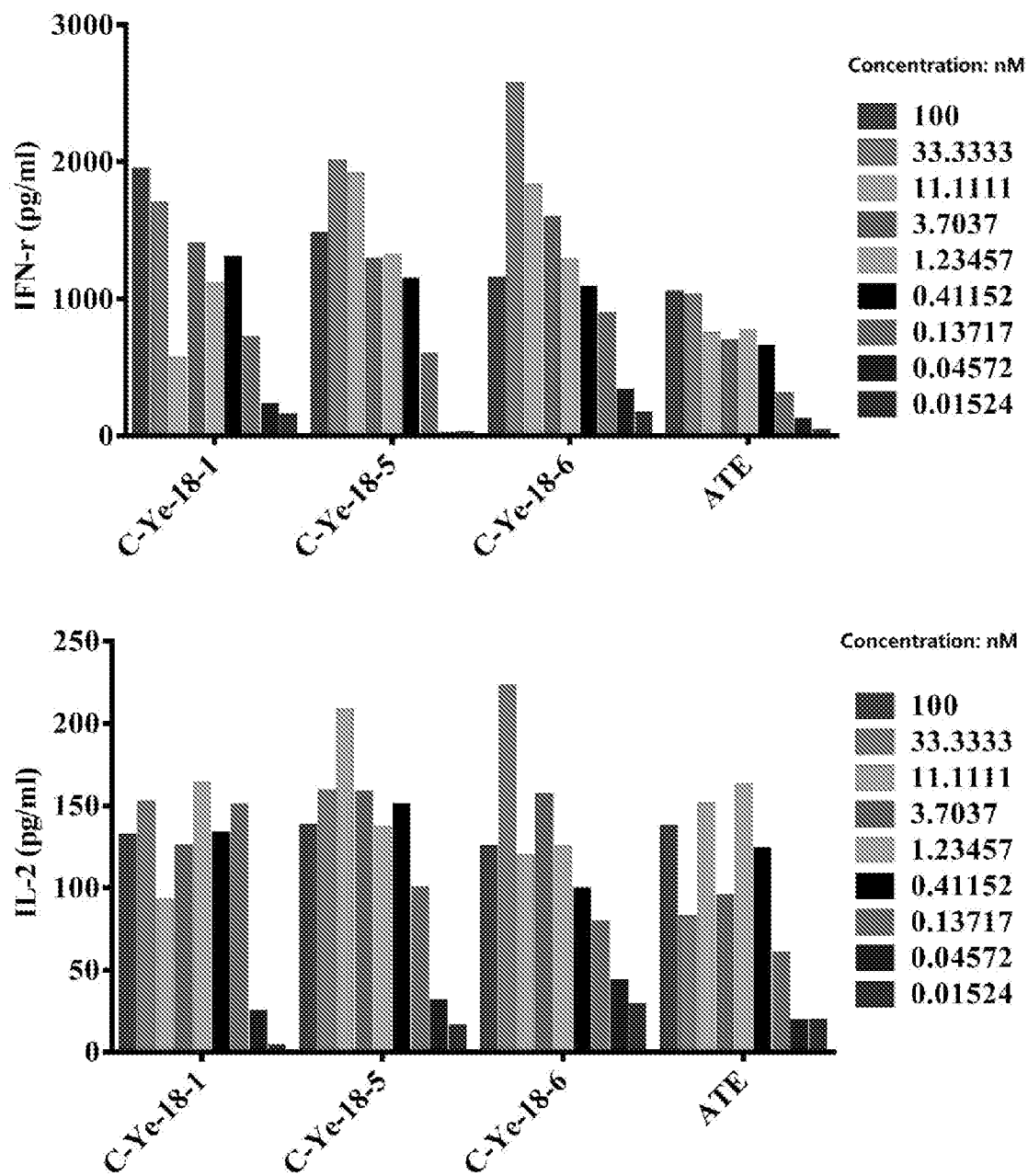
FIG. 4 shows that single-domain antibodies of the present application can effectively activate T cells, and the activation effect is similar to or better than that of an antibody of a positive control.

Results are shown in FIG. 4, the C-Ye-18 mutant samples, C-Ye-18-1, C-Ye-18-5 and C-Ye-18-6 all show relatively good biological activity in the MLR experiment, and the activation level was similar to or superior to that of a control antibody ATE.

Example 12 Cloning and Expression of a Fusion Protein PD-L1/TGFβRII

In the present Example, a TGFβRII extracellular domain (SEQ ID NO: 101) was used as an immunoregulatory molecule moiety of a fusion protein, and a PD-L1 antibody (human IgG1 Fc, LALA mutation) (C-Ye-18-5, SEQ ID: 94) was used as a targeting moiety of the fusion protein to form a PD-L1 antibody/TGFβRII extracellular region fusion protein (PM8001, SEQ ID: 102).

Figure 5:
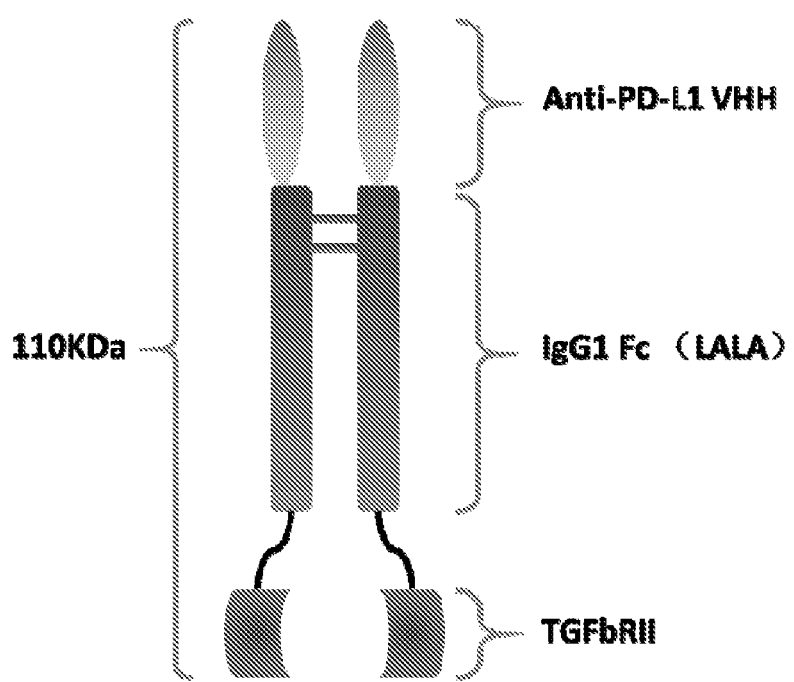
FIG. 5 shows a schematic structural diagram of a fusion protein.

According to a molecular cloning technology, a C-terminal amino acid of a PD-L1 single-chain antibody of the present application was linked to the TGFβRII extracellular region through (G4S)$_4$G and routinely expressed through an Expi-CHO expression system. An expression and purification method was the same as that in Example 3, and a fusion protein PM8001 with the structure as shown in FIG. 5 was obtained.

Example 13 Binding of a PM8001 Molecule to Human PD-L1

Figure 6:
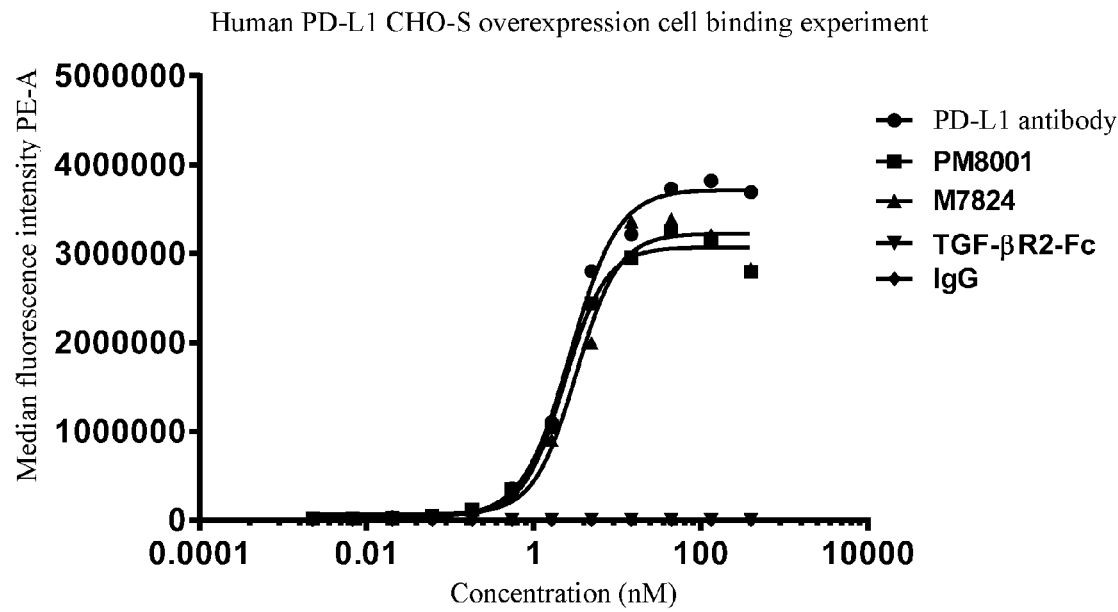
FIG. 6 shows that the fusion protein of the present application can bind to the human PD-L1 protein on the cell surface.

A method for detecting the binding activity of a purified PD-L1 antibody (C-Ye-18-5, SEQ ID: 94), a PM8001 molecule, a TGF-βR2-Fc fusion protein, a positive control M7824 (WO2015/118175 A2) and a negative control IgG protein to PD-L1 on a cell surface was the same as that in Example 4. In a measuring experiment according to the method above, experimental results are shown in FIG. 6, the PM8001 molecule of the present application and the CHO-hPD-L1 cells have binding activity, and the binding activity was similar to that of the positive control molecule M7824.

Figure 7:
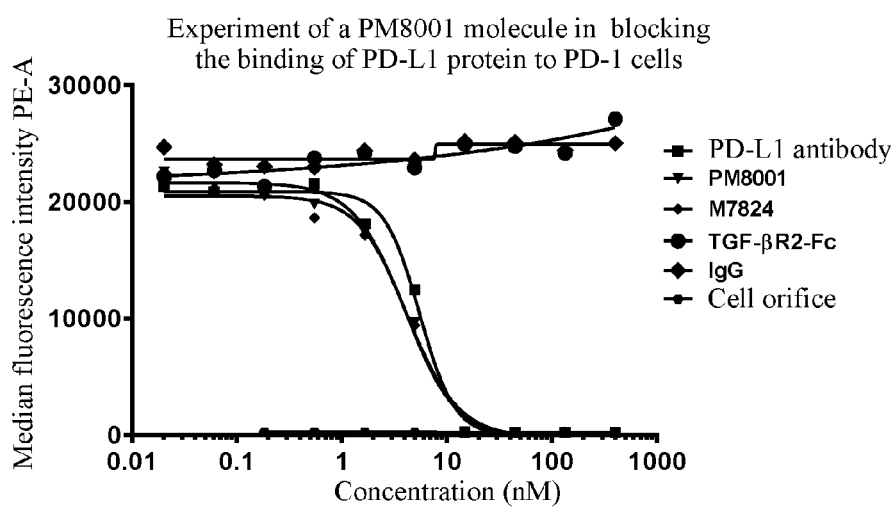
FIG. 7 shows that the fusion protein of the present application can block the binding of the PD-L1 protein to the human PD-1 protein on the cell surface, and the blocking effect of an antibody is similar to that of a positive control.

Example 14 Blocking of Binding of PD-L1 Protein to PD-1 Cells by a PM8001 Molecule A method for detecting blocking of the binding activity of PD-L1 protein to PD-1 cells by a purified PD-L1 antibody (C-Ye-18-5), a PM8001 molecule, a TGF-βR2-Fc fusion protein, a positive control M7824 and a negative control IgG protein was the same as that in Example 9. In a measuring experiment according to the method above, experimental results are shown in FIG. 7, the PM8001 molecule of the present application can block the binding of PD-L1 protein to PD-1 cells, and the blocking level was comparable to that of the positive control molecule M7824.

Example 15 an ELISA Level Binding Experiment of a PM8001 Molecule and Human TGF-β Family Protein Human TGF-β1 (acrobiosystems, TG1-H421), TGF-β2 (PeproTech, 100-35B) and TGF-β3 (PeproTech, 100-36E) protein were diluted with an ELISA coating solution and then added into an ELISA plate for coating overnight at 4° C. The coating solution was removed, 250 µl of PBST was added into each well for washing 3 times, and the ELISA plate was blocked with 5% BSA for 1 hour at room temperature for later use. A purified PD-L1 antibody (C-Ye-18-5), a PM8001 molecule, a TGF-βR2-Fc fusion protein and a positive control M7824 were subjected to gradient dilution and then added into the blocked ELISA plate for incubation at room temperature for 2 hours. PBST was added for washing 3 times, goat anti-human Fc-HRP (abeam, ab97225) was added into each well for incubation at room temperature for 1 hour, after PBST was added for washing 3 times, an ELISA color developing solution was added and placed at room temperature for 3 minutes, an ELISA termination solution was added, and a value of absorbance at 450 nm was read.

Figure 8:
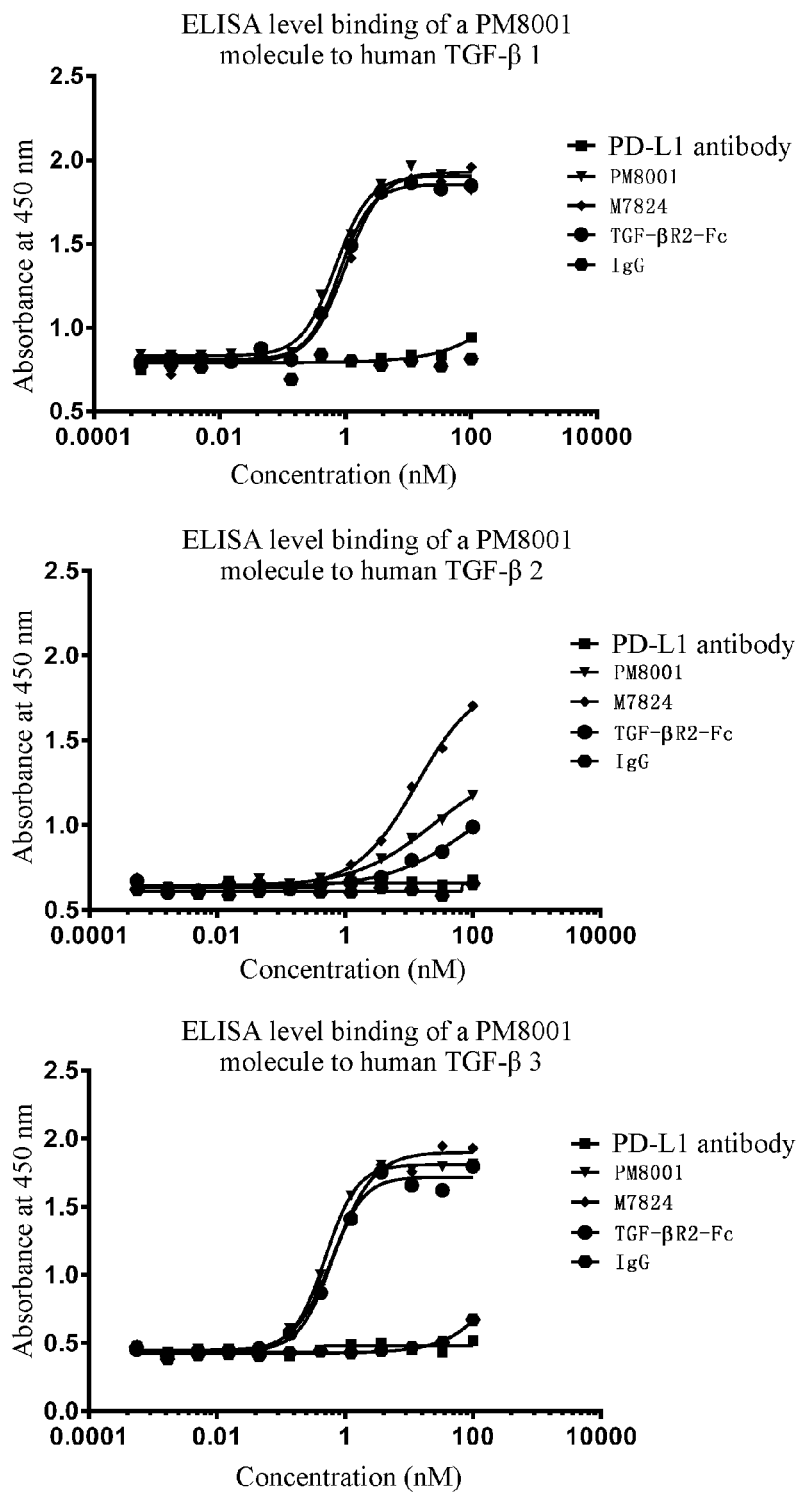
FIG. 8 shows that the fusion protein of the present application can bind to TGFβ1, TGFβ2 and TGFβ3.

In a measuring experiment according to the method above, experimental results are shown in FIG. 8, the PM8001 molecule of the present application has relatively good binding to human TGF-β1 and TGF-β3 proteins at the ELISA level and relatively weak binding activity to human TGF-β2 protein, and the binding level was comparable to that of the positive control molecule M7824.

Example 16 an Experiment of a PM8001 Molecule in Blocking a TGF-β/SMAD Signal Pathway An appropriate amount of 293-TGF-β/SMAD effector cells were taken, inoculated on a 96-well cell culture white bottom plate and placed in an incubator with 5% $CO_2$ for culture overnight at 37° C. A purified PD-L1 antibody (C-Ye-18-5), a PM8001 molecule, a TGF-βR2-Fc fusion protein and a positive control M7824 were subjected to gradient dilution, mixed with TGF-β1 (Acro Biosystems, TG1-H421) and incubated at room temperature for 30 minutes. The mixture above was added into the white bottom plate with cells for continuous culture overnight. A Bio-Glo™ reagent (Promega) was added into each hole, and a multifunctional microplate reader was used to read a fluorescence signal value.

Figure 9:
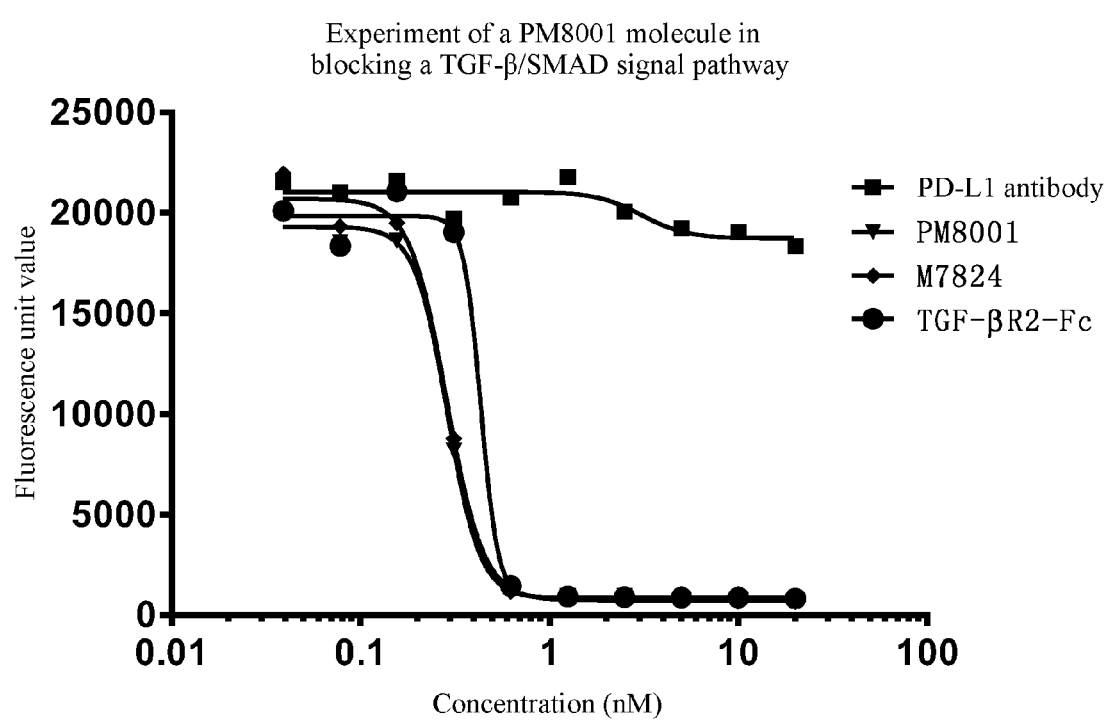
FIG. 9 shows that the fusion protein of the present application can effectively block a TGFβ/SMAD signal pathway.

In a measuring experiment according to the method above, experimental results are shown in FIG. 9, the PM8001 molecule of the present application can block a TGF-3/SMAD signal pathway in vitro, and the blocking level was comparable to that of the positive control molecule M7824.

Example 17 a Mixed Lymphocyte Reaction Experiment

Figure 10:
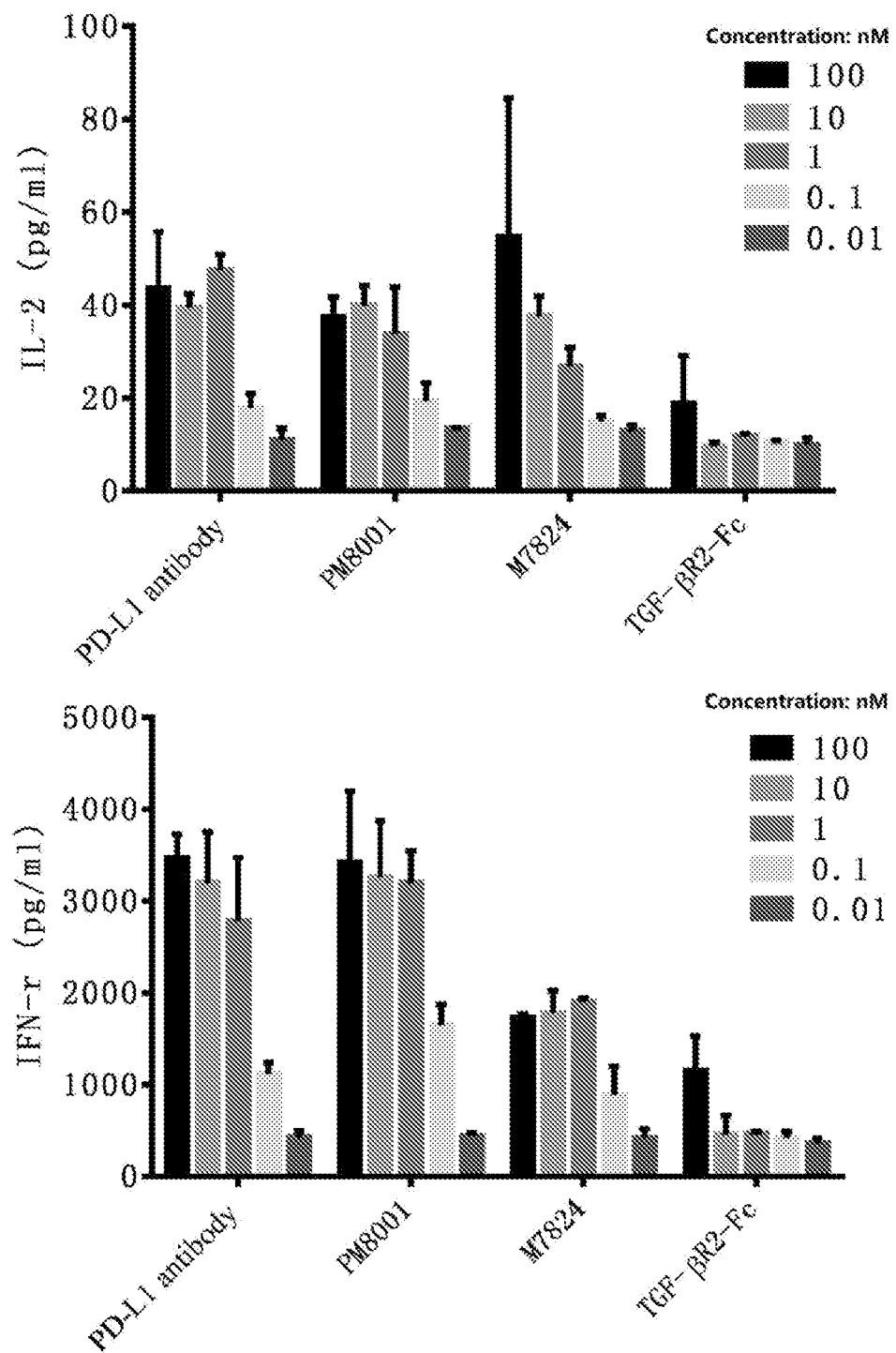
FIG. 10 shows that the fusion protein of the present application can effectively activate T cells, and the activation effect is similar to or better than that of an antibody of a positive control.

A method of using mixed lymphocytes to detect a purified PD-L1 antibody (C-Ye-18-5), a PM8001 molecule, a TGF-βR2-Fc fusion protein, a positive control M7824 and a negative control IgG protein in activation of human T lymphocytes was the same as that in Example 9. Results are shown in FIG. 10, the PM8001 molecule of the present application shows relatively good biological activity in an MLR experiment, and the activation level was comparable to or superior to that of the positive control molecule M7824.

Example 18 Pharmacokinetic Evaluation of PM8001 in Mice

Six SD mice including half male and half female were used in an experiment, light and dark adjustment was carried out every 12 hours, the temperature was 24+/−2° C., the humidity was 40-70%, and the mice drank water and had a diet freely. The mice were purchased from Zhejiang Weitong Lihua Experimental Technology Co., Ltd. On the day of the experiment, a PM8001 molecule was injected into the tail veins of the SD mice once at a dosage of 10 mg/Kg.

Blood collection time points: blood was collected from the jugular veins of the mice 3 minutes, 4 hours, 10 hours, 24 hours, 48 hours, 72 hours, 120 hours, 168 hours, 240 hours, 336 hours, 504 hours and 672 hours after administration. A whole blood sample was placed at 2-8° C. for 30 minutes and centrifuged at 12000 rpm for 5 minutes, serum was collected and centrifuged at 12000 rpm for 5 minutes at 2-8° C. and stored at −80° C., and the molecular weight of free PM8001 in the serum was detected by ELISA. Results are shown in Table 10. The free state molecule of PM8001 of the present application has a half-life of about 146 hours in the SD mice.

TABLE 10

| T½ of PM8001 in SD mice | | |
|---|---|---|
| Test drug | Mode of administration | T½ |
| PM8001 | IV | 146 hours |

Example 19 Study on the Tumor Suppression Activity of PM8001

In this experiment, MC38 cells (h-PD-L1 KIMC38) expressing human PD-L1 were used for determining the anti-tumor effect of PM8001 in PD-L1 transgenic mice. Firstly, an h-PD-L1 KI MC38 tumor-bearing mouse model was established by subcutaneous inoculation. Grouping was carried out when the average tumor volume was 80-120 $mm^3$, the mice were given with different antibodies and different dosages of treatment during single intraperitoneal injection, the tumor volumes and body weight changes of the mice of each group were monitored twice every week for a total of three weeks, the dosage and mode of administration are shown in Table 11, and the tumor volume changes of the mice are shown in FIG. 11.

TABLE 11

| An experimental scheme of the tumor suppression activity of PM8001 | | | |
|---|---|---|---|
| Group | Administration Dosage | Administration volume | Administration concentration |
| Negative control | N/A | 10 ml/kg | N/A |
| M7824 | 24 mg/kg | 10 ml/kg | 2.4 mg/ml |
| PM8001 | 14.7 mg/kg | 10 ml/kg | 1.47 mg/ml |
| C-Ye-18-5 | 10 mg/kg | 10 ml/kg | 1 mg/ml |
| TGF-β R II-Fc | 10 mg/kg | 10 ml/kg | 1 mg/ml |
| C-Ye-18-5 + TGF-β R II-Fc | 10 mg/kg + 10 mg/kg | 10 ml/kg + 10 ml/kg | 1 mg/ml + 1 mg/ml |

Figure 11:
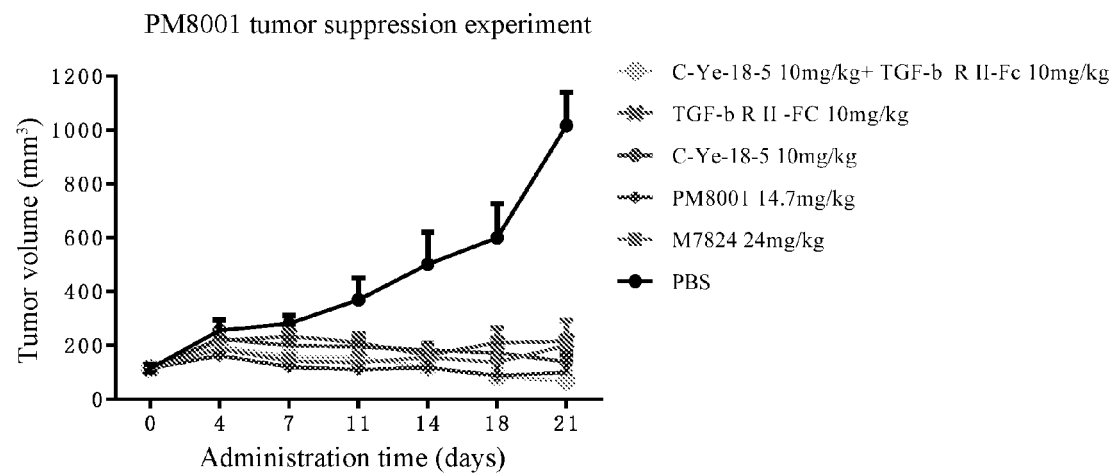
FIG. 11 shows that the fusion protein of the present application can effectively inhibit tumor growth in mice.

Experimental results are shown in FIG. 11. After inoculation with h-PD-L1 KI MC38, the tumor volume of the negative control group was continuously increased, the tumor growth of the TGF-β R II-Fc and C-Ye-18-5 single-use groups was inhibited, while the PM8001 group has better control of tumor growth than the TGF-β R II-Fc and C-Ye-18-5 groups, indicating that PM8001 has a significant tumor suppression efficacy, which was comparable to or even slightly superior to that of the positive control group.

Figure 12:
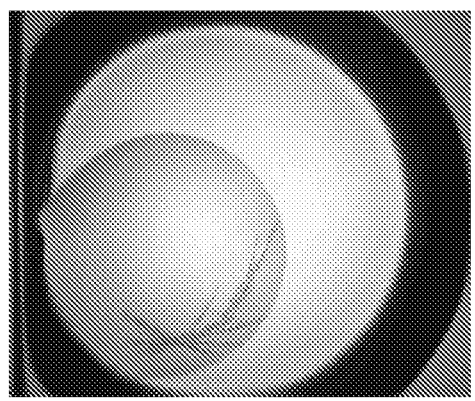
FIG. 12 shows a photograph of the PD-L1-VHH crystal sample of the present application.

Example 20 Identification of the Crystal Structure of a Complex of PD-L1 and a Single-Domain Antibody VHH Fragment In this experiment, an X-ray diffraction method was adopted for identifying the crystal structure of a complex of PD-L1 and a single-domain antibody VHH fragment. A human-derived PD-L1-His tag (SEQ ID: 109) was expressed by an *Escherichia coli* prokaryotic system. A PD-L1 single-domain antibody fusion protein (SEQ ID: 110) was expressed by a CHO system. The PD-L1 single-domain antibody fusion protein was digested and purified with an IdeS enzyme followed by a GingisKHAN enzyme, and finally a PD-L1 single-domain antibody VHH (SEQ ID: 111) was obtained. PD-L1 and VHH were mixed at a molar ratio of 1:1 to prepare a complex sample for crystallization. The purified complex was digested with carboxypeptidase B to remove the His tag of PD-L1. The complex (7.5 mg/mL)

was mixed with a crystallization reagent at a ratio of 1:1 and subjected to crystal culture at 18° C. Three days later, crystals were observed under INT kit culture conditions, and the crystal morphology is shown in FIG. 12.

A single crystal was selected for an X-ray diffraction experiment at Shanghai Light Source, and diffraction data with a resolution of 1.6 Å was obtained. XDS software was used for data processing. A molecular replacement method was adopted for crystal phase identification with PD-L1 (PDB ID: 5jds) and VHH (PDB ID: 5m2j) structures as models respectively. Refmac5 was used for refining the crystal structure. COOT was used for model detection, manual reconstruction and structural verification. The complex crystal belongs to a P21 space group, and the crystal cell parameters are: a=34.62 Å, b=97.99 Å, c=67.52 Å, a=90.00°, 0=90.02°, 7=90.00°.

Figure 13:
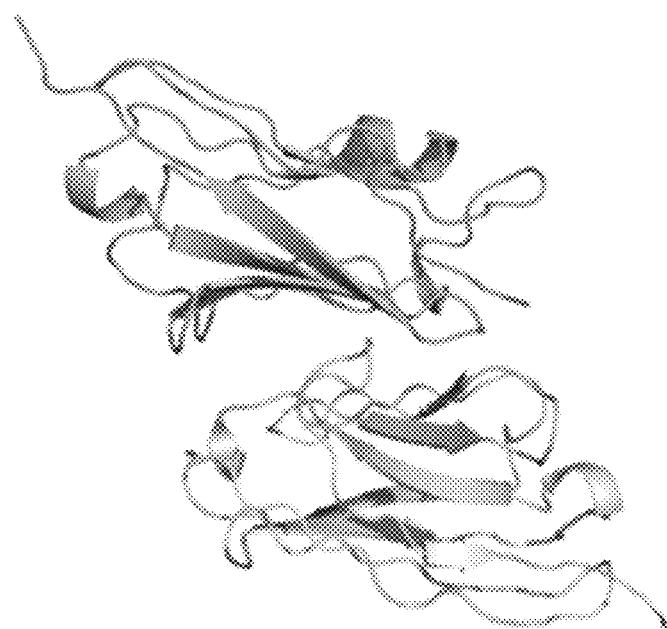
FIG. 13 shows the crystal structure of the PD-L1-VHH complex of the present application (the upper structure is PD-L1 and lower structure is the VHH).
Figure 14:
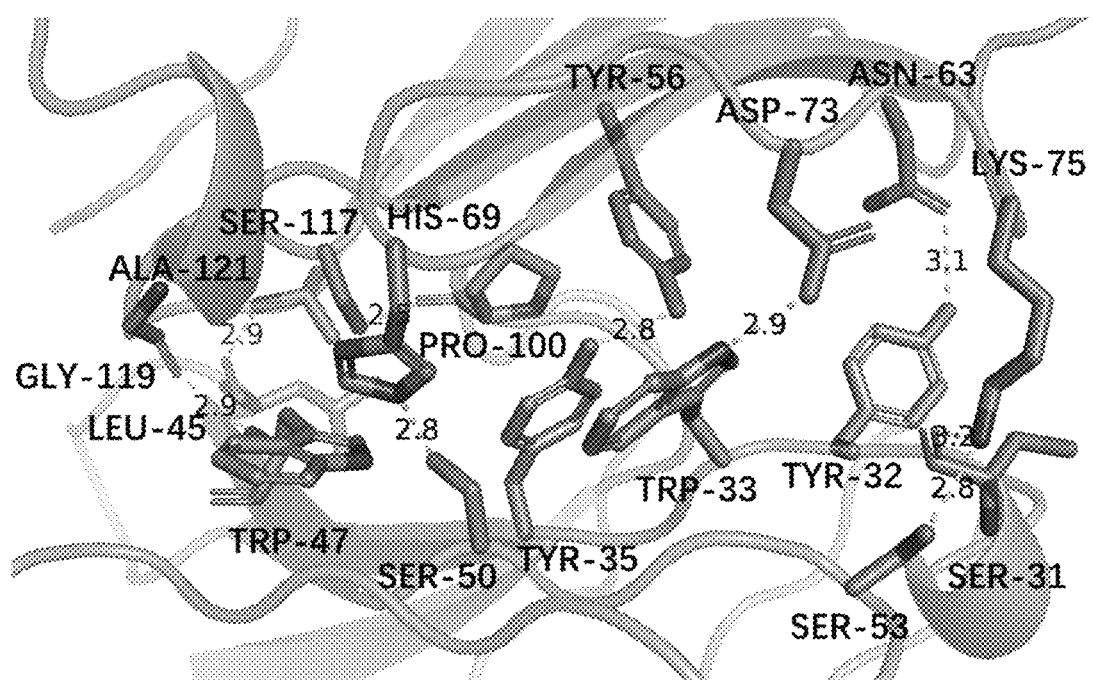
FIG. 14 shows a hydrogen bond interaction interface of PD-L1-VHH of the present application (the upper structure is PD-L1 and the lower structure is VHH).
Figure 15:
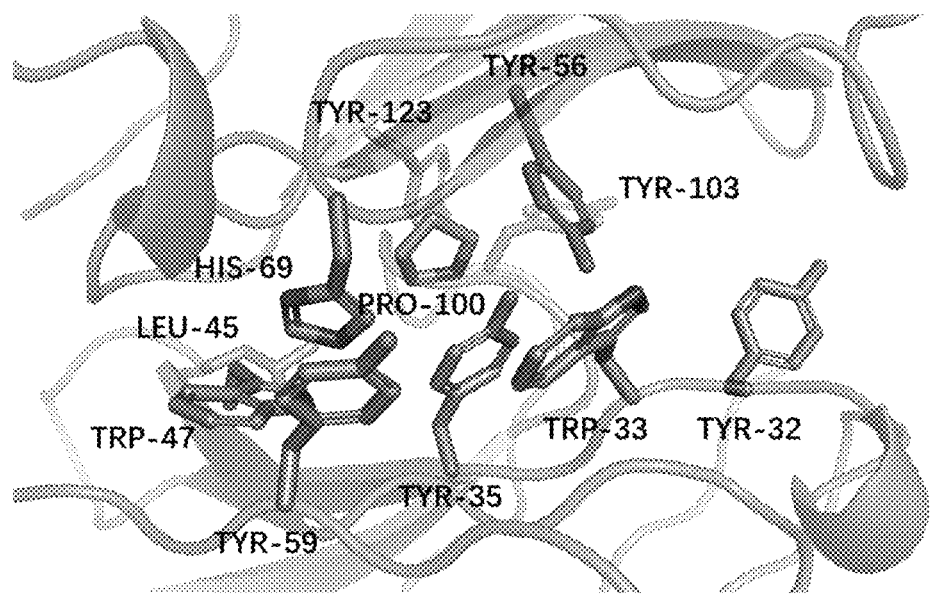
FIG. 15 shows a hydrophobic interaction interface of PD-L1-VHH of the present application (the upper structure is PD-L1 and the lower structure is VHH).

The crystal structure of the PD-L1-VHH complex obtained after structural analysis is shown in FIG. 13. Epitope analysis shows that a main hydrogen-bond interaction between PD-L1 and VHH is concentrated on Tyr56, Asn63, His69, Asp73, Lys75, Ser117, Gly119, Ala121 and other amino acids on PD-L1 (FIG. 14). In addition, Tyr56, His69 and Tyr123 on PD-L1 and Tyr32, Trp33, Tyr35, Leu45, Trp47, Pro100 and Tyr103 on VHH constitute a hydrophobic interaction interface (FIG. 15).

Example 21 the Growth Inhibition Effect of a PM8001 Injection on an h-PD-L1 Knock-In MC38 Model Inoculated Subcutaneously in h-PD-L1 Knock-In C57BL/6 Mice In this study, the in-vivo anti-tumor effect of PM8001 (SEQ ID: 102) administered through intraperitoneal injection on an h-PD-L1 knock-in MC38 mouse colon cancer tumor-bearing model inoculated subcutaneously in h-PD-L1 knock-in C57BL/6 mice, and the safety in h-PD-L1 knock-in mice implanted with h-PD-L1 knock-in MC38 tumors were investigated.

In this study, the h-PD-L1 knock-in MC38 subcutaneous tumor-bearing model was established by subcutaneously inoculating h-PD-L1 knock-in MC38 mouse colon cancer cells into h-PD-L1 knock-in C57BL/6 mice (purchased from GemPharmatech Co, Ltd). Ten days after inoculation, the mice were divided into 5 groups (6 mice per group) according to the tumor volume and subjected to intraperitoneal injection of PBS, 14.7 mg/kg PM8001, 10 mg/kg PM8001-NSD (anti-human PD-L1 VHH), 10 mg/kg PM8001-TGF-βRII and 24.6 mg/kg M7824 (the corresponding molar dosages of the above administration groups were the same) respectively, and administration was carried out twice at an interval of three days. The anti-tumor effect and the safety in the tumor-bearing mice of PM8001, PM8001-NSD, PM8001-TGF-βRII and M7824 were investigated.

Figure 16:
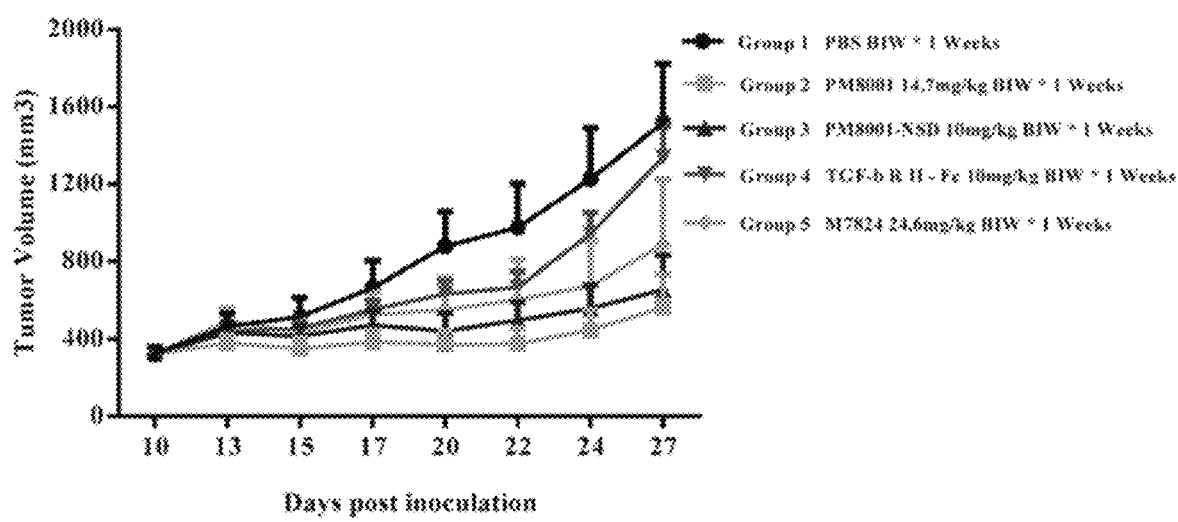
FIG. 16 shows the effect of different drug groups on the tumor volume of h-PD-L1 knock-in mice implanted with h-PD-L1 knock-in MC38 tumors.
Figure 17:
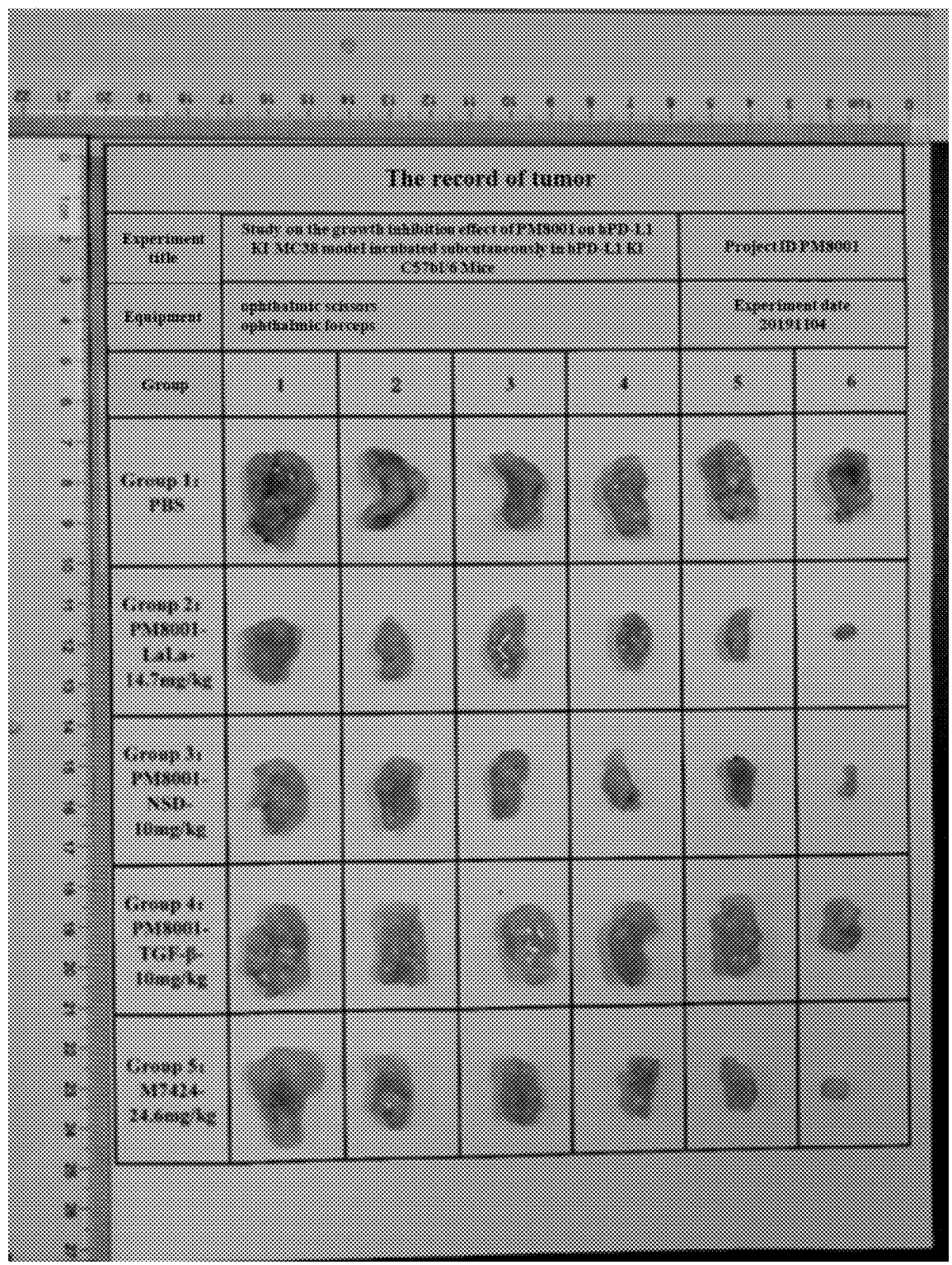
FIG. 17 shows pictures of tumors in different drug groups 27 days after inoculation.
Figure 18:
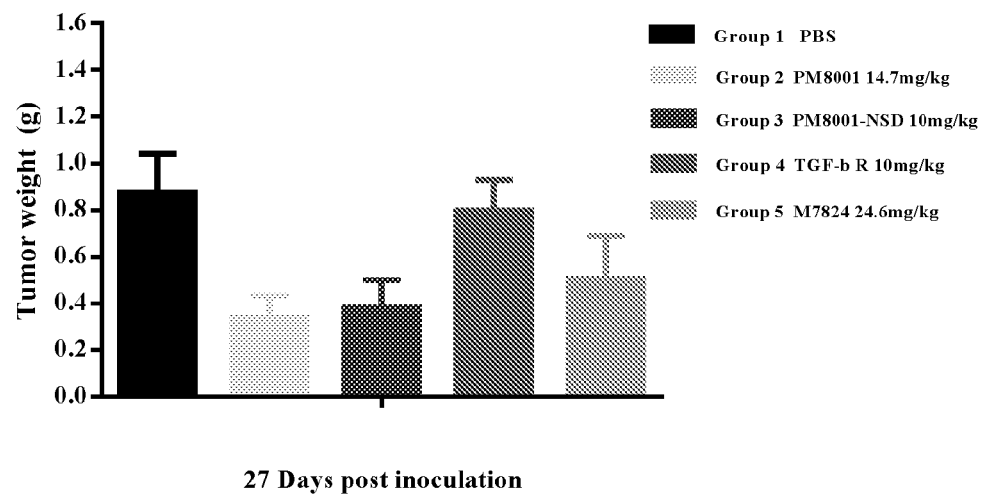
FIG. 18 shows the effect of each group of drugs on tumor weight of h-PD-L1 knock-in mice implanted with h-PD-L1 knock-in MC38 tumors.

FIG. 16 shows the effect of different drug groups on the tumor volume of h-PD-L1 knock-in mice implanted with h-PD-L1 knock-in MC38 tumors. FIG. 17 shows tumor pictures of different drug groups 27 days after inoculation. The tumors of the mice in a negative control PBS group grow rapidly, the tumor volume reaches 1500 mm³ or above 27 days after inoculation (namely, the 17th day after administration), and it indicates that the tumor model in this experiment was successfully established. Compared with the negative control PBS group, the same molar dosage of PM8001, PM8001-NSD, PM8001-TGF-βRII and M7824 can inhibit tumor growth to different degrees, and TGI of the above groups on the 17th day after administration were 80%, 72%, 15% and 53% respectively; the PM8001 injection group has a higher tumor growth inhibition effect than that of PM8001-NSD, PM8001-TGF-β R II and a similar molecular group M7824. At the end of the experiment, the tumors were taken and weighed. The tumor weight in the PM8001 injection group was lower than that of PM8001-NSD, PM8001-TGF-3 R II and the similar molecular group M7824. FIG. 18 shows the effect of each group of drugs on tumor weight of h-PD-L1 knock-in mice implanted with h-PD-L1 knock-in MC38 tumors.

Figure 19:
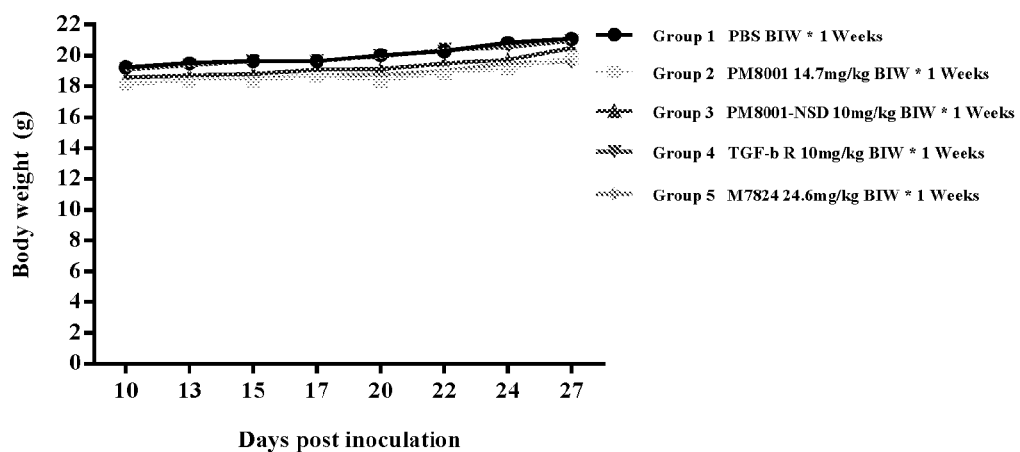
FIG. 19 shows the effect of different drug groups on body weight of h-PD-L1 knock-in mice implanted with h-PD-L1 knock-in MC38 tumors.

FIG. 19 shows the effect of different drug groups on body weight of h-PD-L1 knock-in mice implanted with h-PD-L1 knock-in MC38 tumors. There was no abnormality in the state of the mice in each group; compared with the control group, the body weight of the mice in each administration group was not significantly reduced; at the end of the experiment, the gross anatomy of the mice in each group shows no apparent lesions in main organs, and it indicates that the used administration dosages of drugs in each group in this experiment show no apparent toxicity to the mice.

Example 22 the Growth Inhibition Effect of Different Dosages of PM8001 on an h-PD-L1 Knock-In MC38 Model Inoculated Subcutaneously in h-PD-L1 Knock-In C57BL/6 Mice In this study, the in vivo anti-tumor effect of three different dosages of PM8001 injections on an h-PD-L1 knock-in MC38 mouse colon cancer tumor-bearing model inoculated subcutaneously in h-PD-L1 knock-in C57BL/6 mice (purchased from GemPharmatech Co, Ltd), and the safety in h-PD-L1 knock-in mice implanted with h-PD-L1 knock-in MC38 tumors were investigated.

In this study, the h-PD-L1 knock-in MC38 subcutaneous tumor-bearing model was established by subcutaneously inoculating h-PD-L1 knock-in MC38 mouse colon cancer cells into h-PD-L1 knock-in C57BL/6 mice, and this model can be used to evaluate the anti-tumor effect related to action mechanisms of test products and safety characteristics in a disease state. Seven days after inoculation, the mice were divided into 5 groups (6 mice in each group) according to the tumor volume and administered with single intraperitoneal injection of PBS, different dosages (0.3, 2.1, 14.7 mg/kg) of the PM8001 injection or 24.6 mg/kg M7824 respectively. The anti-tumor effect of different dosages of PM8001 and the safety in tumor-bearing mice were investigated and compared with the similar molecule M7824.

Figure 20:
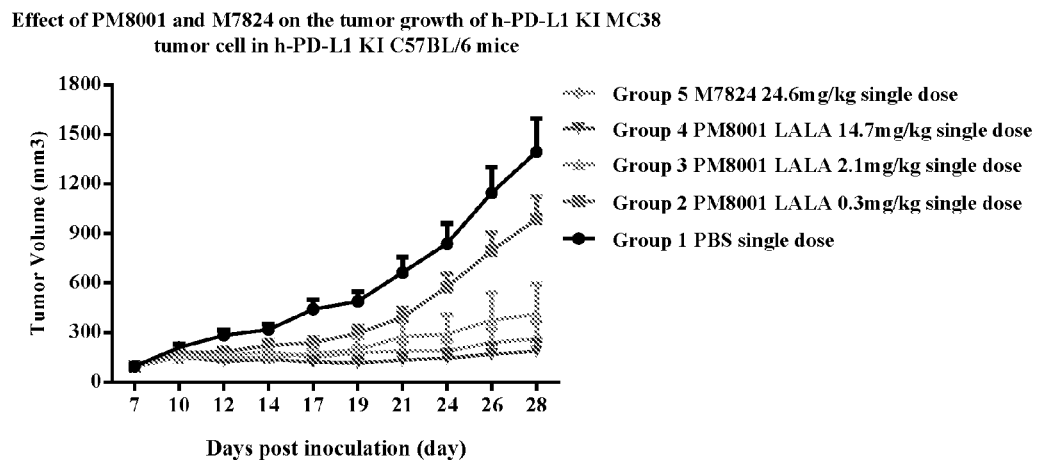
FIG. 20 shows the effect of different drug groups on tumor volume of h-PD-L1 knock-in mice implanted with h-PD-L1 knock-in MC38 tumors.
Figure 21:
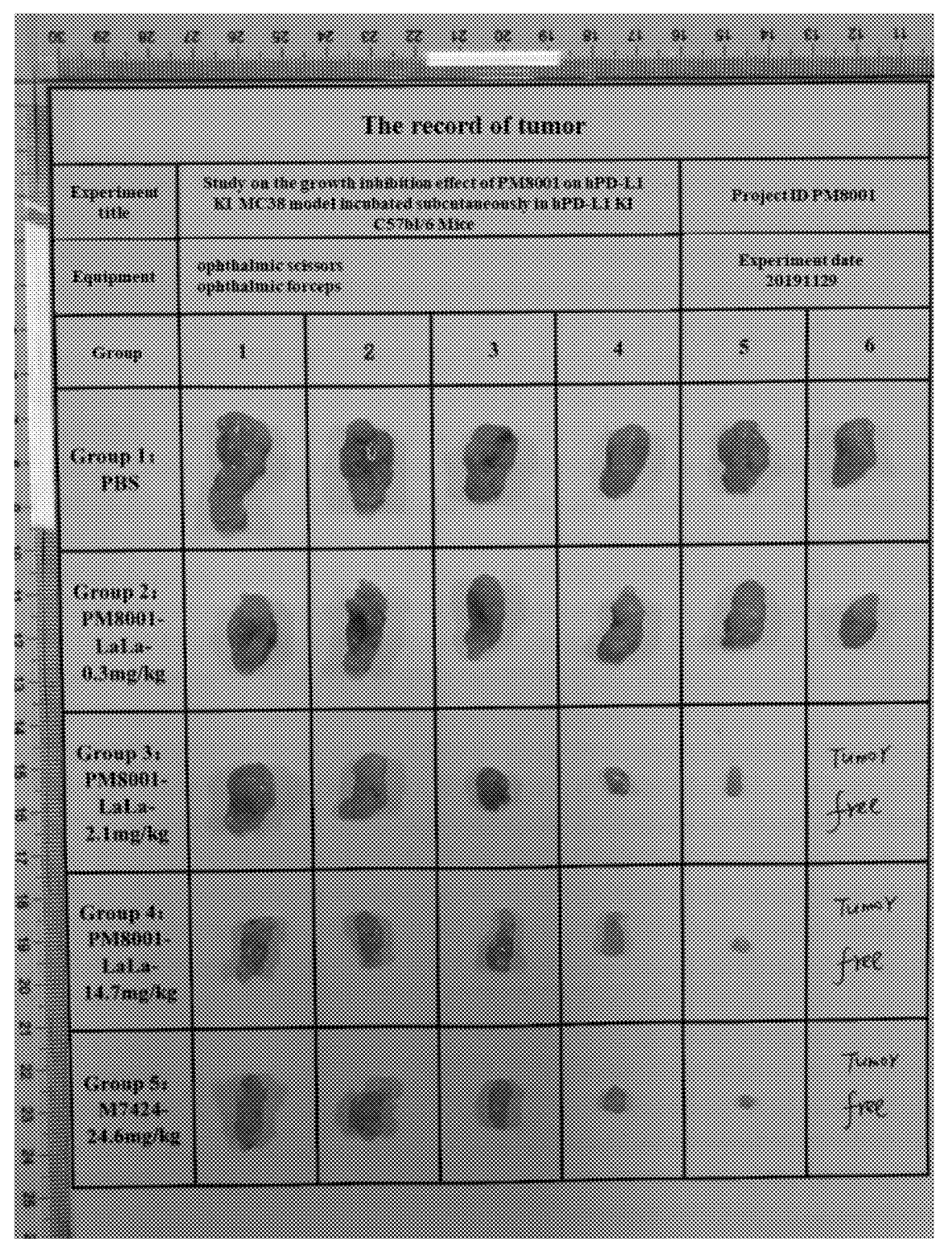
Figure 22:
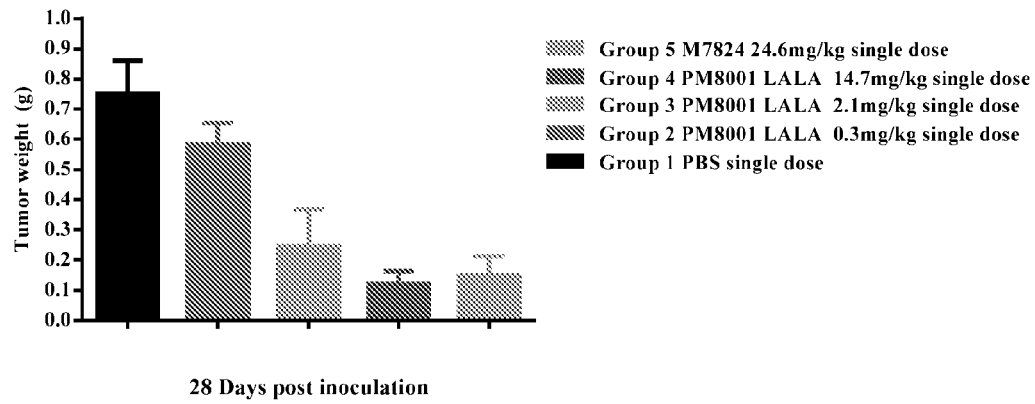
FIG. 22 shows the effect of each group of drugs on tumor weight of h-PD-L1 knock-in mice implanted with h-PD-L1 knock-in MC38 tumors.

FIG. 20 shows the effect of different drug groups on tumor volume of h-PD-L1 knock-in mice implanted with h-PD-L1 knock-in MC38 tumors. FIG. 21 shows tumor pictures of different drug groups 28 days after inoculation. The tumors of the mice in a negative control PBS group grow rapidly, the tumor volume reaches 1300 mm³ or above 28 days after inoculation, and it indicates that the tumor model in this experiment was successfully established. Compared with the negative control PBS group, PM8001 can inhibit tumor growth in a dosage-dependent manner. TGIs at low, medium and high dosages of PM8001 were 31%, 76% and 93% respectively; at the same molar dosage, the tumor growth inhibition effect of the PM8001 group (14.6 mg/kg) was higher than that of the similar molecule M7824 group (24.6 mg/kg). At the end of the experiment, tumors were taken and weighed. PM8001 can reduce tumor weight in a dosage-dependent manner. At the same molar dosage, the tumor inhibition rate of the PM8001 group (14.6 mg/kg) was higher than that of the similar molecule M7824 group (24.6 mg/kg). FIG. 22 shows the effect of each group of drugs on tumor weight of h-PD-L1 knock-in mice implanted with h-PD-L1 knock-in MC38 tumors.

Figure 23:
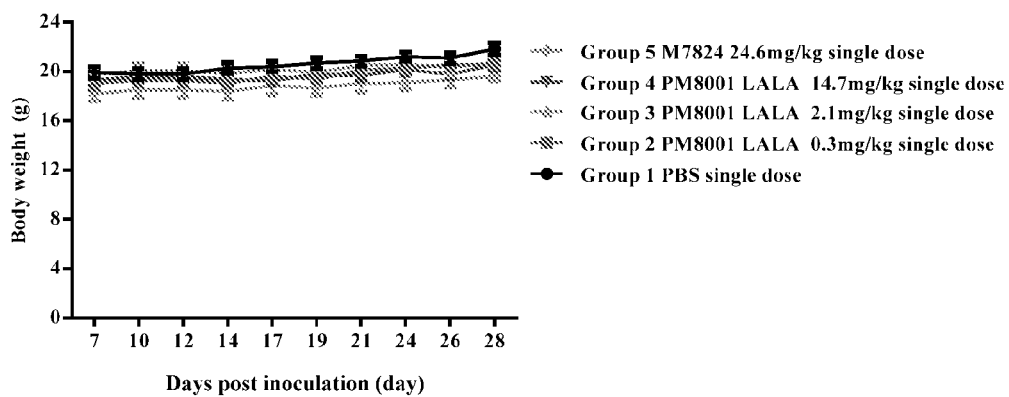
FIG. 23 shows the effect of different drug groups on body weight of h-PD-L1 knock-in mice implanted with h-PD-L1 knock-in MC38 tumors.

FIG. 23 shows the effect of different drug groups on body weight of h-PD-L1 knock-in mice implanted with h-PD-L1 knock-in MC38 tumors. There was no abnormality in the state of the mice in each group; compared with the control group, the body weight of the mice in each administration group was not significantly reduced; at the end of the experiment, the gross anatomy of the mice in each group shows no apparent lesions in main organs, and it indicates that the used administration dosages of drugs in each group in this experiment show no apparent toxicity to the mice.

All documents mentioned in the present application are cited as references in the present application, as if each document was individually cited as a reference. In addition, it should be understood that after reading the above teaching content of the present application, those skilled in the art can make various changes or modifications to the present application, and these equivalent forms also fall within the scope defined by the appended claims of the present application.

What is claimed is:

1. An anti-PD-L1 single-domain antibody comprising a complementarity determining region (CDR), wherein the CDR of the VHH chain consists of the following:
   CDR1 with an amino acid sequence as shown in SEQ ID NO: 1;
   CDR2 with an amino acid sequence as shown in SEQ ID NO: 93, 81, 84, 87, 90, 96, 2 or 7; and
   CDR3 with an amino acid sequence as shown in SEQ ID NO: 3.

2. The VHH chain of an anti-PD-L1 single-domain antibody according to claim 1, wherein the amino acid sequence of CDR2 is shown in SEQ ID NO: 93.

3. A polynucleotide, wherein the polynucleotide encodes the anti-PD-L1 single-domain antibody of claim 1.

4. A single-domain antibody fusion protein, wherein the single-domain antibody fusion protein has a structure as shown in formula I from N-terminal to C-terminal:

Z1-Z2-L-Z3     (Formula I)

wherein,
Z1 is the VHH chain of the anti-PD-L1 single-domain antibody according to claim 1;
Z2 is an Fc fragment of immunoglobulin;
L is a linker sequence; and
Z3 is an immunoregulatory molecule or fragment thereof.

5. The single-domain antibody fusion protein according to claim 4, wherein an amino acid sequence of the single-domain antibody fusion protein is shown in SEQ ID NO: 102.

6. An immunoconjugate, comprising:
   (a) the VHH chain of the anti-PD-L1 single-domain antibody according to claim 1, or the single-domain antibody fusion protein according to claim 4; and
   (b) a coupling moiety selected from the group comprising detectable markers, drugs, toxins, cytokines, radionucleotides or enzymes.

7. A pharmaceutical composition, comprising:
   (i) The anti-PD-L1 single-domain antibody according to claim 1, the single-domain antibody fusion protein according to claim 4, or the immunoconjugate according to claim 6; and
   (ii) a pharmaceutically acceptable carrier.

8. A reagent, detection plate or a kit, comprising the single-domain antibody according to claim 1, the single-domain antibody fusion protein according to claim 4, or the immunoconjugate according to claim 6.

9. A method for treating tumors expressing the PD-L1 protein, wherein the method comprises administering the single-domain antibody according to claim 1, the single-domain antibody fusion protein according to claim 4, or the immunoconjugate according to claim 6.

10. A method for detecting a PD-L1 protein in a sample, which includes the steps:
   (1) contacting the sample with the anti-PD-L1 single-domain antibody according to claim 1, or the single-domain antibody fusion protein according to claim 4; and
   (2) detecting whether an antigen-antibody complex is formed or not, wherein the formation of the complex indicates the presence of the PD-L1 protein in the sample.

* * * * *

SEQUENCE LISTING

```
<160> NUMBER OF SEQ ID NOS: 111

<210> SEQ ID NO 1
<211> LENGTH: 5
<212> TYPE: PRT
<213> ORGANISM: Artificial Sequence
<220> FEATURE:
<223> OTHER INFORMATION: C-Ye-18 CDR1 amino acid sequence

<400> SEQUENCE: 1

Ser Tyr Trp Met Tyr
1               5

<210> SEQ ID NO 2
<211> LENGTH: 17
<212> TYPE: PRT
<213> ORGANISM: Artificial Sequence
<220> FEATURE:
<223> OTHER INFORMATION: C-Ye-18 CDR2 amino acid sequence

<400> SEQUENCE: 2

Ser Ile Asn Ser Ser Ser Ser Thr Tyr Tyr Arg Asp Ser Val Lys
1               5                   10                  15

Gly

<210> SEQ ID NO 3
<211> LENGTH: 6
<212> TYPE: PRT
<213> ORGANISM: Artificial Sequence
<220> FEATURE:
<223> OTHER INFORMATION: C-Ye-18 CDR3 amino acid sequence

<400> SEQUENCE: 3

Asp Pro Gly Gly Tyr Ala
1               5

<210> SEQ ID NO 4
<211> LENGTH: 115
<212> TYPE: PRT
<213> ORGANISM: Artificial Sequence
<220> FEATURE:
<223> OTHER INFORMATION: C-Ye-18 VHH amino acid sequence

<400> SEQUENCE: 4

Glu Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Leu Arg Gln Ala Pro Gly Lys Gly Leu Glu Trp Val
        35                  40                  45

Ser Ser Ile Asn Ser Ser Ser Ser Thr Tyr Tyr Arg Asp Ser Val
    50                  55                  60

Lys Gly Arg Phe Thr Ile Ser Arg Asp Asn Ala Lys Asn Thr Leu Tyr
```

```
                65                  70                  75                  80
Leu Gln Met Asn Ser Leu Lys Ser Glu Asp Thr Ala Val Tyr Tyr Cys
                    85                  90                  95
Ala Lys Asp Pro Gly Gly Tyr Ala Lys Gly Gln Gly Thr Gln Val Thr
                100                 105                 110
Val Ser Ser
        115
```

<210> SEQ ID NO 5
<211> LENGTH: 345
<212> TYPE: DNA
<213> ORGANISM: Artificial Sequence
<220> FEATURE:
<223> OTHER INFORMATION: C-Ye-18 VHH nucleotide sequence

<400> SEQUENCE: 5

```
gaggtgcagc tgcaggagtc tggaggaggc ttggtgcagc ctggggggtc tctgcgactc     60
tcctgtgcag cctctggatt caccttcagt agctactgga tgtattgct  ccgtcaggct    120
ccagggaagg ggctcgagtg ggtctcatct attaatagta gtagtagtag cacatactat   180
cgagactccg tgaagggccg attcaccatc tccagagaca cgccaagaa cacgctgtat    240
ctgcaaatga acagtctgaa atctgaggac acggccgtgt attactgtgc aaaagatcct   300
ggtgggtacg ccaaaggcca ggggacccag gtcaccgtct ccagt                   345
```

<210> SEQ ID NO 6
<211> LENGTH: 5
<212> TYPE: PRT
<213> ORGANISM: Artificial Sequence
<220> FEATURE:
<223> OTHER INFORMATION: C-Ye-04 CDR1 amino acid sequence

<400> SEQUENCE: 6

```
Ser Tyr Trp Met Tyr
1               5
```

<210> SEQ ID NO 7
<211> LENGTH: 17
<212> TYPE: PRT
<213> ORGANISM: Artificial Sequence
<220> FEATURE:
<223> OTHER INFORMATION: C-Ye-04 CDR2 amino acid sequence

<400> SEQUENCE: 7

```
Ser Ile Asn Thr Ser Ser Ser Ser Thr Tyr Tyr Arg Asp Ser Val Lys
1               5                   10                  15
Gly
```

<210> SEQ ID NO 8
<211> LENGTH: 6
<212> TYPE: PRT
<213> ORGANISM: Artificial Sequence
<220> FEATURE:
<223> OTHER INFORMATION: C-Ye-04 CDR3 amino acid sequence

<400> SEQUENCE: 8

```
Asp Pro Gly Gly Tyr Ala
1               5
```

<210> SEQ ID NO 9
<211> LENGTH: 115
<212> TYPE: PRT
<213> ORGANISM: Artificial Sequence
<220> FEATURE:
<223> OTHER INFORMATION: C-Ye-04 VHH amino acid sequence

<400> SEQUENCE: 9

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Leu Arg Gln Ala Pro Gly Lys Gly Leu Glu Trp Val
        35                  40                  45

Ser Ser Ile Asn Thr Ser Ser Ser Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Asp Pro Gly Gly Tyr Ala Lys Gly Gln Gly Thr Gln Val Thr
            100                 105                 110

Val Ser Ser
        115

<210> SEQ ID NO 10
<211> LENGTH: 345
<212> TYPE: DNA
<213> ORGANISM: Artificial Sequence
<220> FEATURE:
<223> OTHER INFORMATION: C-Ye-04 VHH nucleotide sequence

<400> SEQUENCE: 10
caggtgcagc tgcaggagtc tggaggaggc ttggtgcagc ctgggggtc tctgcgactc      60 tcctgtgcag cctctggatt caccttcagt agctactgga tgtattggct ccgtcaggct     120
ccagggaagg ggctcgagtg gtctcatct attaatacta gtagtagtag cacatactat     180
cgagactccg tgaagggccg attcaccatc tccagagaca cgccaagaa cacgctgtat     240 ctgcaaatga acagtctgaa atctgaggac acggccgtgt attactgtgc aaaagatcct     300
ggtgggtacg ccaaaggcca ggggacccag gtcaccgtct ccagt                    345

<210> SEQ ID NO 11
<211> LENGTH: 13
<212> TYPE: PRT
<213> ORGANISM: Artificial Sequence
<220> FEATURE:
<223> OTHER INFORMATION: C-Ye-02 CDR1 amino acid sequence

<400> SEQUENCE: 11

Gly Arg Thr Phe Asn Asn Ser Ala Met Gly Ala Met Gly
1               5                   10

<210> SEQ ID NO 12
<211> LENGTH: 17
<212> TYPE: PRT
<213> ORGANISM: Artificial Sequence
<220> FEATURE:
<223> OTHER INFORMATION: C-Ye-02 CDR2 amino acid sequence

<400> SEQUENCE: 12

Thr Ile Thr Trp Ser Ser Gly Ser Ser Phe Tyr Ala Asn Ser Val Lys
1               5                   10                  15

Gly

<210> SEQ ID NO 13
<211> LENGTH: 17
<212> TYPE: PRT
<213> ORGANISM: Artificial Sequence
<220> FEATURE:
<223> OTHER INFORMATION: C-Ye-02 CDR3 amino acid sequence

<400> SEQUENCE: 13

Ala Ser Arg Lys Leu Gly Gly Val Val Thr Val Val Thr Ser Tyr Asp
1               5                   10                  15

Phe

<210> SEQ ID NO 14
<211> LENGTH: 127
<212> TYPE: PRT
<213> ORGANISM: Artificial Sequence
<220> FEATURE:
<223> OTHER INFORMATION: C-Ye-02 VHH amino acid sequence

<400> SEQUENCE: 14

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Asn Asn Ser
            20                  25                  30

Ala Met Gly Ala Met Gly Trp Phe Arg Gln Ala Pro Gly Lys Glu Arg
        35                  40                  45

Glu Phe Val Ala Thr Ile Thr Trp Ser Ser Gly Ser Ser Phe Tyr Ala
    50                  55                  60

Asn Ser Val Lys Gly Arg Phe Thr Ile Ser Arg Asp Asn Ala Lys Asn
65                  70                  75                  80

Thr Val Tyr Leu Gln Met Asn Ser Leu Lys Pro Glu Asp Thr Ala Val
                85                  90                  95

Tyr Tyr Cys Ala Ser Arg Lys Leu Gly Gly Val Val Thr Val Val Thr
            100                 105                 110

Ser Tyr Asp Phe Trp Gly Gln Gly Thr Gln Val Thr Val Ser Ser
        115                 120                 125

<210> SEQ ID NO 15
<211> LENGTH: 381
<212> TYPE: DNA
<213> ORGANISM: Artificial Sequence
<220> FEATURE:
<223> OTHER INFORMATION: C-Ye-02 VHH nucleotide sequence

<400> SEQUENCE: 15
caggtgcagc tgcaggagtc tgggggagga ttggtgcagg ctggggggctc tctgagactc       60 tcctgtgcag cctctggacg cacccttcaat aactcggcca tggcgccat gggatggttc      120 cgccaggcgc cagggaaaga gcgtgagttt gtcgcgacaa ttacctggag tagtggtagc      180
tcattttatg caaactccgt gaagggccga ttcaccatct ccagagacaa cgccaagaac      240
acggtgtatc tgcaaatgaa cagcctgaaa cctgaggaca cggccgttta ttactgtgca      300
tcacgcaaat tgggagggggt tgtaacggta gttacttcgt atgacttctg gggccagggg      360
acccaggtca ccgtctccag t                                                 381

<210> SEQ ID NO 16
<211> LENGTH: 13
<212> TYPE: PRT
<213> ORGANISM: Artificial Sequence
<220> FEATURE:

<223> OTHER INFORMATION: C-Ye-06 CDR1 amino acid sequence

<400> SEQUENCE: 16

Gly Arg Thr Phe Asp Asn Tyr Ala Met Gly Ala Met Gly
1               5                   10

<210> SEQ ID NO 17
<211> LENGTH: 17
<212> TYPE: PRT
<213> ORGANISM: Artificial Sequence
<220> FEATURE:
<223> OTHER INFORMATION: C-Ye-06 CDR2 amino acid sequence

<400> SEQUENCE: 17

Thr Ile Thr Trp Ser Ser Gly Ser Ser Phe Tyr Ala Asn Ser Val Lys
1               5                   10                  15

Gly

<210> SEQ ID NO 18
<211> LENGTH: 17
<212> TYPE: PRT
<213> ORGANISM: Artificial Sequence
<220> FEATURE:
<223> OTHER INFORMATION: C-Ye-06 CDR3 amino acid sequence

<400> SEQUENCE: 18

Ala Ser Arg Lys Leu Gly Gly Val Val Thr Val Val Thr Ser Tyr Asp
1               5                   10                  15

Phe

<210> SEQ ID NO 19
<211> LENGTH: 127
<212> TYPE: PRT
<213> ORGANISM: Artificial Sequence
<220> FEATURE:
<223> OTHER INFORMATION: C-Ye-06 VHH amino acid sequence

<400> SEQUENCE: 19

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Thr Phe Asp Asn Tyr
            20                  25                  30

Ala Met Gly Ala Met Gly Trp Phe Arg Gln Ala Pro Gly Lys Glu Arg
        35                  40                  45

Glu Phe Val Ala Thr Ile Thr Trp Ser Ser Gly Ser Ser Phe Tyr Ala
    50                  55                  60

Asn Ser Val Lys Gly Arg Phe Thr Ile Ser Arg Asp Asn Ala Lys Asn
65                  70                  75                  80

Thr Val Tyr Leu Gln Met Asn Ser Leu Lys Pro Asp Asp Thr Ala Val
                85                  90                  95

Tyr Tyr Cys Ala Ser Arg Lys Leu Gly Gly Val Val Thr Val Val Thr
            100                 105                 110

Ser Tyr Asp Phe Trp Gly Gln Gly Thr Gln Val Thr Val Ser Ser
        115                 120                 125

<210> SEQ ID NO 20
<211> LENGTH: 381
<212> TYPE: DNA
<213> ORGANISM: Artificial Sequence
<220> FEATURE:
<223> OTHER INFORMATION: C-Ye-06 VHH nucleotide sequence

<400> SEQUENCE: 20

```
caggtgcagc tgcaggagtc tggaggaggc ttggtgcagc ctgggggtc tctgagactc        60 tcctgtgcag cctctggacg caccttcgat aactatgcca tgggcgccat gggatggttc       120
cgccaggcgc cagggaaaga gcgtgagttt gtcgcgacaa ttacctggag tagtggtagc       180 tcatttatg caaactccgt gaagggccga ttcaccatct ccagagacaa cgccaagaac        240
acggtgtatc tgcaaatgaa cagcctgaaa cctgacgaca cggccgttta ttactgtgca       300
tcacgcaaat gggaggggt tgtaacggta gttacttcgt atgacttctg gggccagggg       360
acccaggtca ccgtctccag t                                                 381
```

<210> SEQ ID NO 21
<211> LENGTH: 10
<212> TYPE: PRT
<213> ORGANISM: Artificial Sequence
<220> FEATURE:
<223> OTHER INFORMATION: C-Ye-09 CDR1 amino acid sequence

<400> SEQUENCE: 21

```
Gly Arg Thr Phe Ser Thr Tyr Ala Val Gly
1               5                   10
```

<210> SEQ ID NO 22
<211> LENGTH: 18
<212> TYPE: PRT
<213> ORGANISM: Artificial Sequence
<220> FEATURE:
<223> OTHER INFORMATION: C-Ye-09 CDR2 amino acid sequence

<400> SEQUENCE: 22

```
Gly Arg Leu Thr Trp Ser Gly Ser Arg Thr Tyr Tyr Ala Asp Ser Val
1               5                   10                  15

Lys Gly
```

<210> SEQ ID NO 23
<211> LENGTH: 20
<212> TYPE: PRT
<213> ORGANISM: Artificial Sequence
<220> FEATURE:
<223> OTHER INFORMATION: C-Ye-09 CDR3 amino acid sequence

<400> SEQUENCE: 23

```
Ala Ala Asp Tyr Arg Ser Asn Ser Thr Trp Ser Leu Gln Ser Pro Ala
1               5                   10                  15

Arg Tyr Glu Asn
            20
```

<210> SEQ ID NO 24
<211> LENGTH: 127
<212> TYPE: PRT
<213> ORGANISM: Artificial Sequence
<220> FEATURE:
<223> OTHER INFORMATION: C-Ye-09 VHH amino acid sequence

<400> SEQUENCE: 24

```
Gln Val Gln Leu Gln Glu Ser Gly Gly Gly Leu Val Gln Ala Gly Asp
1               5                   10                  15

Ser Leu Gly Leu Ser Cys Thr Ala Ser Gly Arg Thr Phe Ser Thr Tyr
                20                  25                  30

Ala Val Gly Trp Phe Arg Gln Ala Pro Gly Lys Gly Arg Glu Phe Val
            35                  40                  45
```

Gly Arg Leu Thr Trp Ser Gly Ser Arg Thr Tyr Tyr Ala Asp Ser Val
        50                  55                  60

Lys Gly Arg Phe Thr Ile Ser Arg Asp Asn Ala Lys Asn Thr Val Tyr
 65                  70                  75                  80

Leu Gln Met Asn Ser Leu Arg Pro Glu Asp Thr Ala Val Tyr Tyr Cys
                 85                  90                  95

Ala Ala Asp Tyr Arg Ser Asn Ser Thr Trp Ser Leu Gln Ser Pro Ala
            100                 105                 110

Arg Tyr Glu Asn Trp Gly Gln Gly Thr Gln Val Thr Val Ser Ser
        115                 120                 125

<210> SEQ ID NO 25
<211> LENGTH: 381
<212> TYPE: DNA
<213> ORGANISM: Artificial Sequence
<220> FEATURE:
<223> OTHER INFORMATION: C-Ye-09 VHH nucleotide sequence

<400> SEQUENCE: 25
caggtgcagc tgcaggagtc tgggggagga ttggtgcagg ctggggactc tctgggactc    60
tcctgtacag cctctggacg caccttcagt acctatgccg tgggtggtt ccgccaggct    120 ccagggaagg ggcgtgaatt tgtaggacgt cttacatgga gcgggagtag aacatactat    180
gcagactccg tgaagggccg attcaccatc tccagagaca cgccaagaa cacggtgtat    240 ctgcaaatga acagcctgag acctgaggac acggccgttt attactgtgc agccgactac    300
cgaagtaaca gtacctggtc cctgcaaagc ccggcacgtt atgaaaattg gggccagggg    360
acccaggtca ccgtctccag t                                              381

<210> SEQ ID NO 26
<211> LENGTH: 10
<212> TYPE: PRT
<213> ORGANISM: Artificial Sequence
<220> FEATURE:
<223> OTHER INFORMATION: C-Ye-10 CDR1 amino acid sequence

<400> SEQUENCE: 26

Gly Arg Thr Val Ser Asn Tyr Ala Met Gly
 1               5                  10

<210> SEQ ID NO 27
<211> LENGTH: 17
<212> TYPE: PRT
<213> ORGANISM: Artificial Sequence
<220> FEATURE:
<223> OTHER INFORMATION: C-Ye-10 CDR2 amino acid sequence

<400> SEQUENCE: 27

Arg Ile Thr Gly Ser Gly Ser Ser Thr Phe Tyr Ala Asp Ser Val Lys
 1               5                  10                  15

Gly

<210> SEQ ID NO 28
<211> LENGTH: 19
<212> TYPE: PRT
<213> ORGANISM: Artificial Sequence
<220> FEATURE:
<223> OTHER INFORMATION: C-Ye-10 CDR3 amino acid sequence

<400> SEQUENCE: 28

Ala Ala Asp Arg Trp Arg Ser Met Val Thr Arg Ser Asp Pro Arg Glu
 1               5                  10                  15

Tyr Glu Asn

<210> SEQ ID NO 29
<211> LENGTH: 126
<212> TYPE: PRT
<213> ORGANISM: Artificial Sequence
<220> FEATURE:
<223> OTHER INFORMATION: C-Ye-10 VHH amino acid sequence

<400> SEQUENCE: 29

Gln Val Gln Leu Gln Glu Ser Gly Gly Gly Leu Val Gln Ala Gly Gly
1               5                   10                  15

Ser Leu Arg Leu Ser Cys Val Ala Ser Gly Arg Thr Val Ser Asn Tyr
            20                  25                  30

Ala Met Gly Trp Phe Arg Gln Ala Pro Gly Lys Glu Arg Glu Phe Val
        35                  40                  45

Ala Arg Ile Thr Gly Ser Gly Ser Ser Thr Phe Tyr Ala Asp Ser Val
    50                  55                  60

Lys Gly Arg Phe Thr Ile Ser Arg Asn Asn Leu Ser Asn Thr Val Tyr
65                  70                  75                  80

Leu Gln Met Asn Ser Leu Lys Arg Glu Asp Thr Ala Val Tyr Tyr Cys
                85                  90                  95

Ala Ala Asp Arg Trp Arg Ser Met Val Thr Arg Ser Asp Pro Arg Glu
            100                 105                 110

Tyr Glu Asn Trp Gly Gln Gly Thr Gln Val Thr Val Ser Ser
        115                 120                 125

<210> SEQ ID NO 30
<211> LENGTH: 378
<212> TYPE: DNA
<213> ORGANISM: Artificial Sequence
<220> FEATURE:
<223> OTHER INFORMATION: C-Ye-10 VHH nucleotide sequence

<400> SEQUENCE: 30
caggtgcagc tgcaggagtc tggaggagga ttggtgcagg ctgggggctc tctgagactc      60
tcctgtgtag cctctggacg caccgtcagt aactatgcca tgggctggtt ccgccaggct     120
ccagggaagg agcgtgagtt tgtagcacgg attaccggga gtggtagtag cacattctat     180
gcagactccg tgaagggccg attcaccatc tccagaaaca acttgtcgaa cacggtgtat     240
ctgcagatga acagcctgaa acgtgaggac acggccgttt attactgtgc agcagatcgc     300
tggcgttcaa tggtgactag atctgacccg agggagtatg agaactgggg ccaggggacc     360
caggtcaccg tctccagt                                                  378

<210> SEQ ID NO 31
<211> LENGTH: 10
<212> TYPE: PRT
<213> ORGANISM: Artificial Sequence
<220> FEATURE:
<223> OTHER INFORMATION: C-Ye-17 CDR1 amino acid sequence

<400> SEQUENCE: 31

Gly Arg Thr Val Ser Asn Tyr Ala Met Gly
1               5                   10

<210> SEQ ID NO 32
<211> LENGTH: 17
<212> TYPE: PRT
<213> ORGANISM: Artificial Sequence
<220> FEATURE:
<223> OTHER INFORMATION: C-Ye-17 CDR2 amino acid sequence

<400> SEQUENCE: 32

Arg Ile Thr Gly Ser Gly Ser Ser Thr Phe Tyr Ala Asp Ser Val Lys
1               5                   10                  15

Gly

<210> SEQ ID NO 33
<211> LENGTH: 19
<212> TYPE: PRT
<213> ORGANISM: Artificial Sequence
<220> FEATURE:
<223> OTHER INFORMATION: C-Ye-17 CDR3 amino acid sequence

<400> SEQUENCE: 33

Ala Ala Asp Arg Trp Arg Ser Met Val Thr Arg Ser Asp Pro Arg Glu
1               5                   10                  15

Tyr Glu Asn

<210> SEQ ID NO 34
<211> LENGTH: 126
<212> TYPE: PRT
<213> ORGANISM: Artificial Sequence
<220> FEATURE:
<223> OTHER INFORMATION: C-Ye-17 VHH amino acid sequence

<400> SEQUENCE: 34

Gln Val Gln Leu Gln Glu Ser Gly Gly Gly Leu Val Gln Ala Gly Gly
1               5                   10                  15

Ser Leu Arg Leu Ser Cys Val Ala Ser Gly Arg Thr Val Ser Asn Tyr
            20                  25                  30

Ala Met Gly Trp Phe Arg Gln Ala Pro Gly Lys Glu Arg Glu Phe Val
        35                  40                  45

Ala Arg Ile Thr Gly Ser Gly Ser Ser Thr Phe Tyr Ala Asp Ser Val
    50                  55                  60

Lys Gly Leu Phe Thr Ile Ser Arg Asn Asn Leu Ser Asn Thr Val Tyr
65                  70                  75                  80

Leu Gln Met Asn Ser Leu Lys Arg Glu Asp Thr Ala Val Tyr Tyr Cys
                85                  90                  95

Ala Ala Asp Arg Trp Arg Ser Met Val Thr Arg Ser Asp Pro Arg Glu
            100                 105                 110

Tyr Glu Asn Trp Gly Gln Gly Thr Gln Val Thr Val Ser Ser
        115                 120                 125

<210> SEQ ID NO 35
<211> LENGTH: 378
<212> TYPE: DNA
<213> ORGANISM: Artificial Sequence
<220> FEATURE:
<223> OTHER INFORMATION: C-Ye-17 VHH nucleotide sequence

<400> SEQUENCE: 35
caggtgcagc tgcaggagtc tggaggagga ttggtgcagg ctgggggctc tctgagactc      60
tcctgtgtag cctctggacg caccgtcagt aactatgcca tgggctggtt ccgccaggct     120
ccagggaagg agcgtgagtt tgtagcacgg attaccggga gtggtagtag cacattctat     180
gcagactccg tgaagggcct attcaccatc tccagaaaca acttgtcgaa cacggtgtat     240
ctgcagatga acagcctgaa acgtgaggac acggccgttt attactgtgc agcagatcgc     300

```
tggcgttcaa tggtgactag atctgacccg agggagtatg agaactgggg ccaggggacc      360
caggtcaccg tctccagt                                                    378
```

\<210\> SEQ ID NO 36
\<211\> LENGTH: 10
\<212\> TYPE: PRT
\<213\> ORGANISM: Artificial Sequence
\<220\> FEATURE:
\<223\> OTHER INFORMATION: C-Ye-20 CDR1 amino acid sequence

\<400\> SEQUENCE: 36

```
Gly Arg Thr Val Ser Asn Tyr Ala Met Gly
1               5                   10
```

\<210\> SEQ ID NO 37
\<211\> LENGTH: 17
\<212\> TYPE: PRT
\<213\> ORGANISM: Artificial Sequence
\<220\> FEATURE:
\<223\> OTHER INFORMATION: C-Ye-20 CDR2 amino acid sequence

\<400\> SEQUENCE: 37

```
Arg Ile Thr Gly Ser Gly Ser Ser Thr Phe Tyr Ala Asp Ser Val Lys
1               5                   10                  15

Gly
```

\<210\> SEQ ID NO 38
\<211\> LENGTH: 19
\<212\> TYPE: PRT
\<213\> ORGANISM: Artificial Sequence
\<220\> FEATURE:
\<223\> OTHER INFORMATION: C-Ye-20 CDR3 amino acid sequence

\<400\> SEQUENCE: 38

```
Ala Ala Asp Arg Trp Arg Ser Met Val Thr Arg Ser Tyr Pro Arg Glu
1               5                   10                  15

Tyr Glu Asn
```

\<210\> SEQ ID NO 39
\<211\> LENGTH: 126
\<212\> TYPE: PRT
\<213\> ORGANISM: Artificial Sequence
\<220\> FEATURE:
\<223\> OTHER INFORMATION: C-Ye-20 VHH amino acid sequence

\<400\> SEQUENCE: 39

```
Gln Val Gln Leu Gln Glu Ser Gly Gly Gly Leu Val Gln Ala Gly Gly
1               5                   10                  15

Ser Leu Arg Leu Ser Cys Val Ala Ser Gly Arg Thr Val Ser Asn Tyr
            20                  25                  30

Ala Met Gly Trp Phe Arg Gln Ala Pro Gly Lys Glu Arg Glu Phe Val
        35                  40                  45

Ala Arg Ile Thr Gly Ser Gly Ser Ser Thr Phe Tyr Ala Asp Ser Val
    50                  55                  60

Lys Gly Arg Phe Thr Ile Ser Arg Asp Asn Ala Lys Asn Ala Val Tyr
65                  70                  75                  80

Leu Gln Met Asn Ser Leu Lys Pro Glu Asp Thr Ala Val Tyr Tyr Cys
                85                  90                  95

Ala Ala Asp Arg Trp Arg Ser Met Val Thr Arg Ser Tyr Pro Arg Glu
            100                 105                 110

Tyr Glu Asn Trp Gly Gln Gly Thr Gln Val Thr Val Ser Ser
```

<210> SEQ ID NO 40
<211> LENGTH: 378
<212> TYPE: DNA
<213> ORGANISM: Artificial Sequence
<220> FEATURE:
<223> OTHER INFORMATION: C-Ye-20 VHH nucleotide sequence

<400> SEQUENCE: 40

```
caggtgcagc tgcaggagtc tggaggagga ttggtgcagg ctggggggctc tctgagactc      60
tcctgtgtag cctctggacg caccgtcagt aactatgcca tgggctggtt ccgccaggct     120
ccagggaagg agcgtgagtt tgtagcacgg attaccggga gtggtagtag cacattctat     180
gcagactccg tgaagggccg attcaccatc tccagagaca cgccaagaa cgcgtgtatt     240
ctgcaaatga acagcctgaa acctgaggac acggccgttt attactgtgc agcagatcgc     300
tggcgttcaa tggtgactag atcttacccg agggagtatg agaactgggg ccaggggacc     360
caggtcaccg tctccagt                                                    378
```

<210> SEQ ID NO 41
<211> LENGTH: 10
<212> TYPE: PRT
<213> ORGANISM: Artificial Sequence
<220> FEATURE:
<223> OTHER INFORMATION: C-Ye-24 CDR1 amino acid sequence

<400> SEQUENCE: 41

Gly Arg Thr Val Ser Asn Tyr Ala Met Gly
1               5                   10

<210> SEQ ID NO 42
<211> LENGTH: 17
<212> TYPE: PRT
<213> ORGANISM: Artificial Sequence
<220> FEATURE:
<223> OTHER INFORMATION: C-Ye-24 CDR2 amino acid sequence

<400> SEQUENCE: 42

Arg Ile Thr Gly Ser Gly Arg Thr Thr Tyr Tyr Ala Asp Ser Val Lys
1               5                   10                  15

Gly

<210> SEQ ID NO 43
<211> LENGTH: 19
<212> TYPE: PRT
<213> ORGANISM: Artificial Sequence
<220> FEATURE:
<223> OTHER INFORMATION: C-Ye-24 CDR3 amino acid sequence

<400> SEQUENCE: 43

Ala Ala Asp Arg Trp Arg Ser Met Val Thr Arg Ser Asp Pro Arg Glu
1               5                   10                  15

Tyr Glu Asn

<210> SEQ ID NO 44
<211> LENGTH: 126
<212> TYPE: PRT
<213> ORGANISM: Artificial Sequence
<220> FEATURE:
<223> OTHER INFORMATION: C-Ye-24 VHH amino acid sequence

<400> SEQUENCE: 44

```
Gln Val Gln Leu Gln Glu Ser Gly Gly Val Val Gln Ala Gly Asp
1               5                   10                  15

Ser Leu Arg Leu Ser Cys Val Ala Ser Gly Arg Thr Val Ser Asn Tyr
            20                  25                  30

Ala Met Gly Trp Phe Arg Gln Ala Pro Gly Lys Glu Arg Glu Phe Val
            35                  40                  45

Ala Arg Ile Thr Gly Ser Gly Arg Thr Thr Tyr Tyr Ala Asp Ser Val
            50                  55                  60

Lys Gly Arg Phe Thr Ile Ser Arg Asn Asn Leu Ser Asn Thr Val Tyr
65                  70                  75                  80

Leu Gln Met Asn Ser Leu Lys Arg Glu Asp Thr Ala Val Tyr Tyr Cys
                85                  90                  95

Ala Ala Asp Arg Trp Arg Ser Met Val Thr Arg Ser Asp Pro Arg Glu
            100                 105                 110

Tyr Glu Asn Trp Gly Gln Gly Thr Gln Val Thr Val Ser Ser
            115                 120                 125
```

<210> SEQ ID NO 45
<211> LENGTH: 378
<212> TYPE: DNA
<213> ORGANISM: Artificial Sequence
<220> FEATURE:
<223> OTHER INFORMATION: C-Ye-24 VHH nucleotide sequence

<400> SEQUENCE: 45

```
caggtgcagc tgcaggagtc tggaggaggt gtggtgcagg ctggggactc tctgagactc      60
tcctgtgtag cctctggacg caccgtcagt aactatgcca tgggctggtt ccgccaggct     120
ccagggaagg agcgtgagtt tgtagcacgg attaccggga gtggtcgtac cacatactat     180
gcagactccg tgaagggccg attcaccatc tccagaaaca acttgtcgaa cacggtgtat     240
ctgcagatga acagcctgaa acgtgaggac acggccgttt attactgtgc agcagatcgc     300
tggcgttcaa tggtgactag atctgacccg agggagtatg agaactgggg ccaggggacc     360
caggtcaccg tctccagt                                                   378
```

<210> SEQ ID NO 46
<211> LENGTH: 10
<212> TYPE: PRT
<213> ORGANISM: Artificial Sequence
<220> FEATURE:
<223> OTHER INFORMATION: C-Ye-26 CDR1 amino acid sequence

<400> SEQUENCE: 46

```
Gly Arg Thr Val Ser Asn Tyr Ala Met Gly
1               5                   10
```

<210> SEQ ID NO 47
<211> LENGTH: 17
<212> TYPE: PRT
<213> ORGANISM: Artificial Sequence
<220> FEATURE:
<223> OTHER INFORMATION: C-Ye-26 CDR2 amino acid sequence

<400> SEQUENCE: 47

```
Arg Ile Thr Gly Ser Gly Ser Thr Phe Tyr Ala Asp Ser Val Lys
1               5                   10                  15

Gly
```

<210> SEQ ID NO 48
<211> LENGTH: 19

<210> SEQ ID NO 49
<211> LENGTH: 126
<212> TYPE: PRT
<213> ORGANISM: Artificial Sequence
<220> FEATURE:
<223> OTHER INFORMATION: C-Ye-26 CDR3 amino acid sequence

<400> SEQUENCE: 48

Ala Ala Asp Arg Trp Arg Ser Met Val Thr Arg Ser Asp Pro Arg Asp
1               5                   10                  15

Tyr Glu Asn

<210> SEQ ID NO 49
<211> LENGTH: 126
<212> TYPE: PRT
<213> ORGANISM: Artificial Sequence
<220> FEATURE:
<223> OTHER INFORMATION: C-Ye-26 VHH amino acid sequence

<400> SEQUENCE: 49

Gln Val Gln Leu Gln Glu Ser Gly Gly Gly Leu Val Gln Ala Gly Gly
1               5                   10                  15

Ser Leu Arg Leu Ser Cys Val Ala Ser Gly Arg Thr Val Ser Asn Tyr
            20                  25                  30

Ala Met Gly Trp Phe Arg Gln Ala Pro Gly Lys Glu Arg Glu Phe Val
        35                  40                  45

Ala Arg Ile Thr Gly Ser Gly Ser Ser Thr Phe Tyr Ala Asp Ser Val
    50                  55                  60

Lys Gly Arg Phe Thr Ile Ser Arg Asn Asn Leu Ser Asn Thr Val Tyr
65                  70                  75                  80

Leu Gln Met Asn Ser Leu Lys Arg Glu Asp Thr Ala Val Tyr Tyr Cys
                85                  90                  95

Ala Ala Asp Arg Trp Arg Ser Met Val Thr Arg Ser Asp Pro Arg Asp
            100                 105                 110

Tyr Glu Asn Trp Gly Gln Gly Thr Gln Val Thr Val Ser Ser
        115                 120                 125

<210> SEQ ID NO 50
<211> LENGTH: 378
<212> TYPE: DNA
<213> ORGANISM: Artificial Sequence
<220> FEATURE:
<223> OTHER INFORMATION: C-Ye-26 VHH nucleotide sequence

<400> SEQUENCE: 50
caggtgcagc tgcaggagtc tgggggagga ttggtgcagg ctggggggctc tctgagactc      60
tcctgtgtag cctctggacg caccgtcagt aactatgcca tgggctggtt ccgccaggct     120
ccagggaagg agcgtgagtt tgtagcacgg attaccggga gtggtagtag cacattctat     180
gcagactccg tgaagggccg attcaccatc tccagaaaca acttgtcgaa cacggtgtat     240
ctgcagatga acagcctgaa acgtgaggac acggccgttt attactgtgc agcagatcgc     300
tggcgttcaa tggtgactag atctgacccg aggattatg agaactgggg ccaggggacc     360
caggtcaccg tctccagt                                                   378

<210> SEQ ID NO 51
<211> LENGTH: 10
<212> TYPE: PRT
<213> ORGANISM: Artificial Sequence
<220> FEATURE:
<223> OTHER INFORMATION: C-Ye-27 CDR1 amino acid sequence

<400> SEQUENCE: 51

Gly Arg Thr Phe Ser Arg Tyr Ala Val Gly
1               5                   10

<210> SEQ ID NO 52
<211> LENGTH: 17
<212> TYPE: PRT
<213> ORGANISM: Artificial Sequence
<220> FEATURE:
<223> OTHER INFORMATION: C-Ye-27 CDR2 amino acid sequence

<400> SEQUENCE: 52

Ala Ile Thr Trp Ser Gly Gly Tyr Thr Tyr Tyr Ala Asp Ser Val Lys
1               5                   10                  15

Gly

<210> SEQ ID NO 53
<211> LENGTH: 15
<212> TYPE: PRT
<213> ORGANISM: Artificial Sequence
<220> FEATURE:
<223> OTHER INFORMATION: C-Ye-27 CDR3 amino acid sequence

<400> SEQUENCE: 53

Ala Val Asp Thr Arg Asn Val Ile Gly Pro Arg Ala Gly Asp Tyr
1               5                   10                  15

<210> SEQ ID NO 54
<211> LENGTH: 122
<212> TYPE: PRT
<213> ORGANISM: Artificial Sequence
<220> FEATURE:
<223> OTHER INFORMATION: C-Ye-27 VHH amino acid sequence

<400> SEQUENCE: 54

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Arg Tyr
            20                  25                  30

Ala Val Gly Trp Phe Arg Gln Ala Pro Gly Leu Gly Arg Asp Phe Val
        35                  40                  45

Ala Ala Ile Thr Trp Ser Gly Gly Tyr Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Val Asp Thr Arg Asn Val Ile Gly Pro Arg Ala Gly Asp Tyr Trp
            100                 105                 110

Gly Gln Gly Thr Gln Val Thr Val Ser Ser
        115                 120

<210> SEQ ID NO 55
<211> LENGTH: 366
<212> TYPE: DNA
<213> ORGANISM: Artificial Sequence
<220> FEATURE:
<223> OTHER INFORMATION: C-Ye-27 VHH nucleotide sequence

<400> SEQUENCE: 55
caggtgcagc tgcaggagtc tggaggagga ttggtgcagg ctgggggctc tctgagactc      60
tcctgtgcag cctctggacg caccttcagt aggtatgccg tgggctggtt ccgccaggct     120

```
ccagggctgg ggcgtgactt tgtagcagct attacctgga gtggtggtta cacatactat    180
gcggactccg tgaagggccg attcaccatc tccagagaca cgccaagaa cacggtgtat    240 ttgcaaatga acagcctgaa acctgaggac acggccgttt attactgtgc agtcgatacg    300
aggaatgtaa tcggcccaag agcgggagac tactggggcc aggggaccca ggtcaccgtc    360
tccagt                                                               366
```

```
<210> SEQ ID NO 56
<211> LENGTH: 10
<212> TYPE: PRT
<213> ORGANISM: Artificial Sequence
<220> FEATURE:
<223> OTHER INFORMATION: C-Ye-30 CDR1 amino acid sequence

<400> SEQUENCE: 56

Gly Ser Thr Phe Ser Arg Tyr Ala Val Gly
1               5                   10
```

```
<210> SEQ ID NO 57
<211> LENGTH: 17
<212> TYPE: PRT
<213> ORGANISM: Artificial Sequence
<220> FEATURE:
<223> OTHER INFORMATION: C-Ye-30 CDR2 amino acid sequence

<400> SEQUENCE: 57

Ala Ile Thr Trp Ser Gly Gly Tyr Thr Tyr Tyr Ala Asp Ser Val Lys
1               5                   10                  15

Gly
```

```
<210> SEQ ID NO 58
<211> LENGTH: 15
<212> TYPE: PRT
<213> ORGANISM: Artificial Sequence
<220> FEATURE:
<223> OTHER INFORMATION: C-Ye-30 CDR3 amino acid sequence

<400> SEQUENCE: 58

Ala Val Asp Thr Arg Asn Val Ile Gly Pro Arg Ala Gly Asp Tyr
1               5                   10                  15
```

```
<210> SEQ ID NO 59
<211> LENGTH: 122
<212> TYPE: PRT
<213> ORGANISM: Artificial Sequence
<220> FEATURE:
<223> OTHER INFORMATION: C-Ye-30 VHH amino acid sequence

<400> SEQUENCE: 59

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Phe Ser Arg Tyr
            20                  25                  30

Ala Val Gly Trp Phe Arg Gln Ala Pro Gly Leu Gly Arg Asp Phe Val
        35                  40                  45

Ala Ala Ile Thr Trp Ser Gly Gly Tyr Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95
```

Ala Val Asp Thr Arg Asn Val Ile Gly Pro Arg Ala Gly Asp Tyr Trp
            100                 105                 110

Gly Gln Gly Thr Gln Val Thr Val Ser Ser
        115                 120

<210> SEQ ID NO 60
<211> LENGTH: 366
<212> TYPE: DNA
<213> ORGANISM: Artificial Sequence
<220> FEATURE:
<223> OTHER INFORMATION: C-Ye-30 VHH nucleotide sequence

<400> SEQUENCE: 60
caggtgcagc tgcaggagtc tggaggagga ttggtgcagg ctggggctc tctgagactc      60 tcctgtgcag cctctggaag caccttcagt aggtatgccg tgggctggtt ccgccaggct    120
ccagggctgg ggcgtgactt tgtagcagct attacctgga gtggtggtta cacatactat    180
gcggactccg tgaagggccg attcaccatc tccagagaca cgccaagaa cacggtgtat     240 ttgcaaatga acagcctgaa acctgaggac acggccgttt attactgtgc agtcgatacg    300
aggaatgtaa tcggcccaag agcgggagac tactggggcc aggggaccca ggtcaccgtc    360
tccagt                                                               366

<210> SEQ ID NO 61
<211> LENGTH: 10
<212> TYPE: PRT
<213> ORGANISM: Artificial Sequence
<220> FEATURE:
<223> OTHER INFORMATION: C-Ye-32 CDR1 amino acid sequence

<400> SEQUENCE: 61

Gly Arg Thr Phe Ser Arg Tyr Ala Val Gly
1               5                   10

<210> SEQ ID NO 62
<211> LENGTH: 17
<212> TYPE: PRT
<213> ORGANISM: Artificial Sequence
<220> FEATURE:
<223> OTHER INFORMATION: C-Ye-32 CDR2 amino acid sequence

<400> SEQUENCE: 62

Ala Ile Thr Trp Ser Gly Gly Tyr Thr Tyr Tyr Ala Asp Ser Val Lys
1               5                   10                  15

Gly

<210> SEQ ID NO 63
<211> LENGTH: 15
<212> TYPE: PRT
<213> ORGANISM: Artificial Sequence
<220> FEATURE:
<223> OTHER INFORMATION: C-Ye-32 CDR3 amino acid sequence

<400> SEQUENCE: 63

Ala Val Asp Thr Arg Asn Val Ile Gly Pro Arg Ala Gly Asp Tyr
1               5                   10                  15

<210> SEQ ID NO 64
<211> LENGTH: 122
<212> TYPE: PRT
<213> ORGANISM: Artificial Sequence
<220> FEATURE:
<223> OTHER INFORMATION: C-Ye-32 VHH amino acid sequence

<400> SEQUENCE: 64

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Arg Tyr
            20                  25                  30

Ala Val Gly Trp Phe Arg Gln Ala Pro Gly Leu Gly Arg Asp Phe Val
        35                  40                  45

Ala Ala Ile Thr Trp Ser Gly Gly Tyr Thr Tyr Tyr Ala Asp Ser Val
    50                  55                  60

Lys Gly Arg Phe Thr Ile Ser Arg Asp Asn Ala Lys Asn Thr Ile Tyr
65                  70                  75                  80

Leu Gln Met Asn Ser Leu Asn Val Glu Asp Thr Gly Val Tyr Tyr Cys
                85                  90                  95

Ala Val Asp Thr Arg Asn Val Ile Gly Pro Arg Ala Gly Asp Tyr Trp
            100                 105                 110

Gly Gln Gly Thr Gln Val Thr Val Ser Ser
        115                 120

<210> SEQ ID NO 65
<211> LENGTH: 366
<212> TYPE: DNA
<213> ORGANISM: Artificial Sequence
<220> FEATURE:
<223> OTHER INFORMATION: C-Ye-32 VHH nucleotide sequence

<400> SEQUENCE: 65
caggtgcagc tgcaggagtc tggaggagga ttggtgcagg ctggggggctc tctgagactc      60
tcctgtgcag cctctggacg caccttcagt aggtatgccg tgggctggtt ccgccaggct     120
ccagggctgg ggcgtgactt tgtagcagct attacctgga gtggtggtta cacatactat     180
gcggactccg tgaagggccg attcaccatc tccagagaca acgccaagaa cacgatctat     240
ctccaaatga acagcctgaa cgttgaggac acgggcgttt attactgcgc agtcgatacg     300
aggaatgtaa tcggcccaag agcgggagac tactggggcc aggggaccca ggtcaccgtc     360
tccagt                                                                366

<210> SEQ ID NO 66
<211> LENGTH: 13
<212> TYPE: PRT
<213> ORGANISM: Artificial Sequence
<220> FEATURE:
<223> OTHER INFORMATION: C-Ye-34 CDR1 amino acid sequence

<400> SEQUENCE: 66

Ala Ala Ser Gly Arg Thr Phe Ser Arg Phe Ala Met Gly
1               5                   10

<210> SEQ ID NO 67
<211> LENGTH: 17
<212> TYPE: PRT
<213> ORGANISM: Artificial Sequence
<220> FEATURE:
<223> OTHER INFORMATION: C-Ye-34 CDR2 amino acid sequence

<400> SEQUENCE: 67

Ala Ile Ser Trp Ser Gly Gly Met Ile Tyr Tyr Thr Asp Ser Val Lys
1               5                   10                  15

Gly

<210> SEQ ID NO 68
<211> LENGTH: 15
<212> TYPE: PRT
<213> ORGANISM: Artificial Sequence
<220> FEATURE:
<223> OTHER INFORMATION: C-Ye-34 CDR3 amino acid sequence

<400> SEQUENCE: 68

Ala Val Asp Thr Arg Asn Val Ile Gly Pro Arg Ala Gly Asp Tyr
1               5                   10                  15

<210> SEQ ID NO 69
<211> LENGTH: 122
<212> TYPE: PRT
<213> ORGANISM: Artificial Sequence
<220> FEATURE:
<223> OTHER INFORMATION: C-Ye-34 VHH amino acid sequence

<400> SEQUENCE: 69

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Arg Phe
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Met Ile Tyr Tyr Thr Asp Ser Val
    50                  55                  60

Lys Gly Arg Phe Thr Ile Ser Arg Asp Asn Ala Lys Asn Met Leu Tyr
65                  70                  75                  80

Leu Gln Met Asn Ser Leu Lys Pro Glu Asp Thr Ala Val Tyr Tyr Cys
                85                  90                  95

Ala Val Asp Thr Arg Asn Val Ile Gly Pro Arg Ala Gly Asp Tyr Trp
            100                 105                 110

Gly Gln Gly Thr Gln Val Thr Val Ser Ser
        115                 120

<210> SEQ ID NO 70
<211> LENGTH: 366
<212> TYPE: DNA
<213> ORGANISM: Artificial Sequence
<220> FEATURE:
<223> OTHER INFORMATION: C-Ye-34 VHH nucleotide sequence

<400> SEQUENCE: 70
caggtgcagc tgcaggagtc tgggggagga ttggtgcagg ctggggggctc tctgagactc    60 tcctgtgcag cctctggacg cactttcagt aggtttgcca tgggctggtt ccgccaggct   120
ccagggaagg agcgtgagtt tgtagccgct attagctgga gtggtggtat gatatactat   180
acagactccg tgaagggccg attcaccatc tccagagaca acgccaagaa catgctgtat   240
ctgcaaatga acagcctgaa acctgaggac acggccgttt attactgtgc agtcgatacg   300
aggaatgtaa tcggcccaag agcgggagac tactgggggcc aggggaccca ggtcaccgtc   360
tccagt                                                              366

<210> SEQ ID NO 71
<211> LENGTH: 10
<212> TYPE: PRT
<213> ORGANISM: Artificial Sequence
<220> FEATURE:
<223> OTHER INFORMATION: C-Ye-39 CDR1 amino acid sequence

<400> SEQUENCE: 71

Gly Arg Ala Phe Ser Val Tyr Pro Met Ala
1               5                  10

<210> SEQ ID NO 72
<211> LENGTH: 16
<212> TYPE: PRT
<213> ORGANISM: Artificial Sequence
<220> FEATURE:
<223> OTHER INFORMATION: C-Ye-39 CDR2 amino acid sequence

<400> SEQUENCE: 72

Arg Leu Thr Tyr Thr Ser Asn Thr Phe Tyr Ala Asp Ser Val Lys Gly
1               5                  10                  15

<210> SEQ ID NO 73
<211> LENGTH: 19
<212> TYPE: PRT
<213> ORGANISM: Artificial Sequence
<220> FEATURE:
<223> OTHER INFORMATION: C-Ye-39 CDR3 amino acid sequence

<400> SEQUENCE: 73

Ala Val Glu Asn Arg Ser Ser Ser Trp Ser Leu Gln Ser Pro Ala Arg
1               5                  10                  15

Tyr Asp Asp

<210> SEQ ID NO 74
<211> LENGTH: 125
<212> TYPE: PRT
<213> ORGANISM: Artificial Sequence
<220> FEATURE:
<223> OTHER INFORMATION: C-Ye-39 VHH amino acid sequence

<400> SEQUENCE: 74

Gln Val Gln Leu Gln Glu Ser Gly Gly Gly Leu Val Gln Ala Gly Gly
1               5                  10                  15

Ser Leu Arg Leu Ser Cys Thr Ala Ser Gly Arg Ala Phe Ser Val Tyr
                20                  25                  30

Pro Met Ala Trp Phe Arg Gln Ala Pro Gly Lys Glu Arg Glu Phe Ile
            35                  40                  45

Ala Arg Leu Thr Tyr Thr Ser Asn Thr Phe Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Glu Asn Arg Ser Ser Ser Trp Ser Leu Gln Ser Pro Ala Arg Tyr
                100                 105                 110

Asp Asp Trp Gly Gln Gly Thr Gln Val Thr Val Ser Ser
            115                 120                 125

<210> SEQ ID NO 75
<211> LENGTH: 375
<212> TYPE: DNA
<213> ORGANISM: Artificial Sequence
<220> FEATURE:
<223> OTHER INFORMATION: C-Ye-39 VHH nucleotide sequence

<400> SEQUENCE: 75
caggtgcagc tgcaggagtc tgggggagga ttggtgcagg ctgggggctc tctgagactc     60

```
tcatgtacag cctctggacg cgccttcagt gtctacccca tggcctggtt ccgccaggct    120
ccagggaagg agcgtgagtt tatagcacgt cttacgtata ctagtaacac attctatgca    180
gactccgtga agggccgatt caccatctcc agagacaacg ccaagaacac ggtgtatctg    240
cagatgaaca gcctgaaacc tgaggacacg gccgtttatt actgtgcggt cgagaaccgc    300
agtagtagtt ggtccctgca aagcccggca cgttatgatg actggggcca ggggacccag    360
gtcaccgtct ccagt                                                    375
```

```
<210> SEQ ID NO 76
<211> LENGTH: 10
<212> TYPE: PRT
<213> ORGANISM: Artificial Sequence
<220> FEATURE:
<223> OTHER INFORMATION: C-Ye-42 CDR1 amino acid sequence

<400> SEQUENCE: 76

Gly Arg Thr Gly Ser Arg Tyr Ala Val Gly
1               5                   10

<210> SEQ ID NO 77
<211> LENGTH: 17
<212> TYPE: PRT
<213> ORGANISM: Artificial Sequence
<220> FEATURE:
<223> OTHER INFORMATION: C-Ye-42 CDR2 amino acid sequence

<400> SEQUENCE: 77

Ala Ile Thr Trp Ser Gly Gly Tyr Thr Tyr Tyr Ala Asp Ser Val Lys
1               5                   10                  15

Gly

<210> SEQ ID NO 78
<211> LENGTH: 15
<212> TYPE: PRT
<213> ORGANISM: Artificial Sequence
<220> FEATURE:
<223> OTHER INFORMATION: C-Ye-42 CDR3 amino acid sequence

<400> SEQUENCE: 78

Ala Val Asp Thr Arg Asn Val Ile Gly Pro Arg Ala Gly Asp Tyr
1               5                   10                  15

<210> SEQ ID NO 79
<211> LENGTH: 122
<212> TYPE: PRT
<213> ORGANISM: Artificial Sequence
<220> FEATURE:
<223> OTHER INFORMATION: C-Ye-42 VHH amino acid sequence

<400> SEQUENCE: 79

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Gly Ser Arg Tyr
            20                  25                  30

Ala Val Gly Trp Phe Arg Gln Ala Pro Gly Leu Gly Arg Asp Phe Val
        35                  40                  45

Ala Ala Ile Thr Trp Ser Gly Gly Tyr Thr Tyr Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
```

-continued

```
                    85                  90                  95
Ala Val Asp Thr Arg Asn Val Ile Gly Pro Arg Ala Gly Asp Tyr Trp
                100                 105                 110

Gly Gln Gly Thr Gln Val Thr Val Ser Ser
        115                 120

<210> SEQ ID NO 80
<211> LENGTH: 366
<212> TYPE: DNA
<213> ORGANISM: Artificial Sequence
<220> FEATURE:
<223> OTHER INFORMATION: C-Ye-42 VHH nucleotide sequence

<400> SEQUENCE: 80
caggtgcagc tgcaggagtc tggaggagga ttggtgcagg ctgggggctc tctgagactc      60
tcctgtgcag cctctggacg caccggcagt aggtatgccg tgggctggtt ccgccaggct     120
ccagggctgg ggcgtgactt tgtagcagct attacctgga gtggtggtta cacatactat     180
gcggactccg tgaagggccg attcaccatc tccagagaca cgccaagaa cacgatgtat      240 ctgcaaatga acagcctaaa acctgaagac acggccgttt attactgtgc agtcgatacg     300
aggaatgtaa tcggcccaag agcgggagac tactggggcc aggggaccca ggtcaccgtc     360
tccagt                                                                366

<210> SEQ ID NO 81
<211> LENGTH: 17
<212> TYPE: PRT
<213> ORGANISM: Artificial Sequence
<220> FEATURE:
<223> OTHER INFORMATION: C-Ye-18-1 CDR2 amino acid sequence

<400> SEQUENCE: 81

Ser Ile Asn Ser Gly Ser Ser Ser Thr Tyr Tyr Arg Asp Ser Val Lys
1               5                   10                  15
Gly

<210> SEQ ID NO 82
<211> LENGTH: 115
<212> TYPE: PRT
<213> ORGANISM: Artificial Sequence
<220> FEATURE:
<223> OTHER INFORMATION: C-Ye-18-1 VHH amino acid sequence

<400> SEQUENCE: 82

Glu Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Leu Arg Gln Ala Pro Gly Lys Gly Leu Glu Trp Val
        35                  40                  45

Ser Ser Ile Asn Ser Gly Ser Ser Ser Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Asp Pro Gly Gly Tyr Ala Lys Gly Gln Gly Thr Gln Val Thr
                100                 105                 110

Val Ser Ser
```

-continued

```
        115

<210> SEQ ID NO 83
<211> LENGTH: 345
<212> TYPE: DNA
<213> ORGANISM: Artificial Sequence
<220> FEATURE:
<223> OTHER INFORMATION: C-Ye-18-1 VHH nucleotide sequence

<400> SEQUENCE: 83
gaggtgcagc tgcaggagtc tggaggaggc ttggtgcagc tggggggtc tctgcgactc      60 tcctgtgcag cctctggatt caccttcagt agctactgga tgtattggct ccgtcaggct    120
ccagggaagg ggctcgagtg gtctcatct attaatagtg gtagtagtag cacatactat    180
cgagactccg tgaagggccg attcaccatc tccagagaca acgccaagaa cacgctgtat    240
ctgcaaatga acagtctgaa atctgaggac acggccgtgt attactgtgc aaaagatcct    300
ggtgggtacg ccaaaggcca ggggacccag gtcaccgtct ccagt                    345

<210> SEQ ID NO 84
<211> LENGTH: 17
<212> TYPE: PRT
<213> ORGANISM: Artificial Sequence
<220> FEATURE:
<223> OTHER INFORMATION: C-Ye-18-2 CDR2 amino acid sequence

<400> SEQUENCE: 84

Ser Ile Ser Ser Ser Ser Ser Ser Thr Tyr Tyr Arg Asp Ser Val Lys
1               5                   10                  15

Gly

<210> SEQ ID NO 85
<211> LENGTH: 115
<212> TYPE: PRT
<213> ORGANISM: Artificial Sequence
<220> FEATURE:
<223> OTHER INFORMATION: C-Ye-18-2 VHH amino acid sequence

<400> SEQUENCE: 85

Glu Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Leu Arg Gln Ala Pro Gly Lys Gly Leu Glu Trp Val
        35                  40                  45

Ser Ser Ile Ser Ser Ser Ser Ser Ser Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Asp Pro Gly Gly Tyr Ala Lys Gly Gln Gly Thr Gln Val Thr
            100                 105                 110

Val Ser Ser
        115

<210> SEQ ID NO 86
<211> LENGTH: 345
<212> TYPE: DNA
<213> ORGANISM: Artificial Sequence
<220> FEATURE:
```

<223> OTHER INFORMATION: C-Ye-18-2 VHH nucleotide sequence

<400> SEQUENCE: 86

```
gaggtgcagc tgcaggagtc tggaggaggc ttggtgcagc ctggggggtc tctgcgactc      60
tcctgtgcag cctctggatt caccttcagt agctactgga tgtattggct ccgtcaggct     120
ccagggaagg ggctcgagtg ggtctcatct attagtagta gtagtagtag cacatactat     180
cgagactccg tgaagggccg attcaccatc tccagagaca acgccaagaa cacgctgtat     240
ctgcaaatga acagtctgaa atctgaggac acggccgtgt attactgtgc aaaagatcct     300
ggtgggtacg ccaaaggcca ggggacccag gtcaccgtct ccagt                     345
```

<210> SEQ ID NO 87
<211> LENGTH: 17
<212> TYPE: PRT
<213> ORGANISM: Artificial Sequence
<220> FEATURE:
<223> OTHER INFORMATION: C-Ye-18-3 CDR2 amino acid sequence

<400> SEQUENCE: 87

```
Ser Ile Gly Ser Ser Ser Ser Thr Tyr Tyr Arg Asp Ser Val Lys
1               5                   10                  15
Gly
```

<210> SEQ ID NO 88
<211> LENGTH: 115
<212> TYPE: PRT
<213> ORGANISM: Artificial Sequence
<220> FEATURE:
<223> OTHER INFORMATION: C-Ye-18-3 VHH amino acid sequence

<400> SEQUENCE: 88

```
Glu Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Leu Arg Gln Ala Pro Gly Lys Gly Leu Glu Trp Val
        35                  40                  45

Ser Ser Ile Gly Ser Ser Ser Ser Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Asp Pro Gly Gly Tyr Ala Lys Gly Gln Gly Thr Gln Val Thr
            100                 105                 110

Val Ser Ser
        115
```

<210> SEQ ID NO 89
<211> LENGTH: 345
<212> TYPE: DNA
<213> ORGANISM: Artificial Sequence
<220> FEATURE:
<223> OTHER INFORMATION: C-Ye-18-3 VHH nucleotide sequence

<400> SEQUENCE: 89

```
gaggtgcagc tgcaggagtc tggaggaggc ttggtgcagc ctggggggtc tctgcgactc      60
tcctgtgcag cctctggatt caccttcagt agctactgga tgtattggct ccgtcaggct     120
```

```
ccagggaagg ggctcgagtg gtctcatct  attggtagta gtagtagtag cacatactat    180
cgagactccg tgaagggccg attcaccatc tccagagaca acgccaagaa cacgctgtat    240
ctgcaaatga acagtctgaa atctgaggac acggccgtgt attactgtgc aaaagatcct    300
ggtgggtacg ccaaaggcca ggggacccag gtcaccgtct ccagt                    345
```

```
<210> SEQ ID NO 90
<211> LENGTH: 17
<212> TYPE: PRT
<213> ORGANISM: Artificial Sequence
<220> FEATURE:
<223> OTHER INFORMATION: C-Ye-18-4 CDR2 amino acid sequence

<400> SEQUENCE: 90

Ser Ile Tyr Ser Gly Ser Ser Ser Thr Tyr Tyr Arg Asp Ser Val Lys
1               5                   10                  15

Gly
```

```
<210> SEQ ID NO 91
<211> LENGTH: 115
<212> TYPE: PRT
<213> ORGANISM: Artificial Sequence
<220> FEATURE:
<223> OTHER INFORMATION: C-Ye-18-4 VHH amino acid sequence

<400> SEQUENCE: 91

Glu Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Leu Arg Gln Ala Pro Gly Lys Gly Leu Glu Trp Val
        35                  40                  45

Ser Ser Ile Tyr Ser Gly Ser Ser Ser Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Asp Pro Gly Gly Tyr Ala Lys Gly Gln Gly Thr Gln Val Thr
            100                 105                 110

Val Ser Ser
        115
```

```
<210> SEQ ID NO 92
<211> LENGTH: 345
<212> TYPE: DNA
<213> ORGANISM: Artificial Sequence
<220> FEATURE:
<223> OTHER INFORMATION: C-Ye-18-4 VHH nucleotide sequence

<400> SEQUENCE: 92
gaggtgcagc tgcaggagtc tggaggaggc ttggtgcagc ctgggggtc  tctgcgactc    60 tcctgtgcag cctctggatt caccttcagt agctactgga tgtattggct ccgtcaggct   120
ccagggaagg ggctcgagtg gtctcatct  atttacagtg gtagtagtag cacatactat   180
cgagactccg tgaagggccg attcaccatc tccagagaca acgccaagaa cacgctgtat   240
ctgcaaatga acagtctgaa atctgaggac acggccgtgt attactgtgc aaaagatcct   300
ggtgggtacg ccaaaggcca ggggacccag gtcaccgtct ccagt                   345
```

<210> SEQ ID NO 93
<211> LENGTH: 17
<212> TYPE: PRT
<213> ORGANISM: Artificial Sequence
<220> FEATURE:
<223> OTHER INFORMATION: C-Ye-18-5 CDR2 amino acid sequence

<400> SEQUENCE: 93

Ser Ile Asn Ser Asp Ser Ser Thr Tyr Tyr Arg Asp Ser Val Lys
1               5                   10                  15

Gly

<210> SEQ ID NO 94
<211> LENGTH: 115
<212> TYPE: PRT
<213> ORGANISM: Artificial Sequence
<220> FEATURE:
<223> OTHER INFORMATION: C-Ye-18-5 VHH amino acid sequence

<400> SEQUENCE: 94

Glu Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Leu Arg Gln Ala Pro Gly Lys Gly Leu Glu Trp Val
        35                  40                  45

Ser Ser Ile Asn Ser Asp Ser Ser Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Asp Pro Gly Gly Tyr Ala Lys Gly Gln Gly Thr Gln Val Thr
            100                 105                 110

Val Ser Ser
        115

<210> SEQ ID NO 95
<211> LENGTH: 345
<212> TYPE: DNA
<213> ORGANISM: Artificial Sequence
<220> FEATURE:
<223> OTHER INFORMATION: C-Ye-18-5 VHH nucleotide sequence

<400> SEQUENCE: 95
gaggtgcagc tgcaggagtc tggaggaggc ttggtgcagc ctggggggtc tctgcgactc      60
tcctgtgcag cctctggatt caccttcagt agctactgga tgtattggct ccgtcaggct     120
ccagggaagg ggctcgagtg ggtctcatct attaatagtg acagtagtag cacatactat     180
cgagactccg tgaagggccg attcaccatc tccagagaca cgccaagaa cacgctgtat      240 ctgcaaatga acagtctgaa atctgaggac acggccgtgt attactgtgc aaaagatcct     300
ggtgggtacg ccaaaggcca ggggacccag gtcaccgtct ccagt                     345

<210> SEQ ID NO 96
<211> LENGTH: 17
<212> TYPE: PRT
<213> ORGANISM: Artificial Sequence
<220> FEATURE:
<223> OTHER INFORMATION: C-Ye-18-6 CDR2 amino acid sequence

<400> SEQUENCE: 96

Ser Ile Ser Gly Ser Ser Ser Thr Tyr Tyr Arg Asp Ser Val Lys
1               5                   10                  15

Gly

<210> SEQ ID NO 97
<211> LENGTH: 115
<212> TYPE: PRT
<213> ORGANISM: Artificial Sequence
<220> FEATURE:
<223> OTHER INFORMATION: C-Ye-18-6 VHH amino acid sequence

<400> SEQUENCE: 97

Glu Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Leu Arg Gln Ala Pro Gly Lys Gly Leu Glu Trp Val
        35                  40                  45

Ser Ser Ile Ser Gly Ser Ser Ser Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Asp Pro Gly Gly Tyr Ala Lys Gly Gln Gly Thr Gln Val Thr
            100                 105                 110

Val Ser Ser
        115

<210> SEQ ID NO 98
<211> LENGTH: 345
<212> TYPE: DNA
<213> ORGANISM: Artificial Sequence
<220> FEATURE:
<223> OTHER INFORMATION: C-Ye-18-6 VHH nucleotide sequence

<400> SEQUENCE: 98
gaggtgcagc tgcaggagtc tggaggaggc ttggtgcagc ctgggggtc tctgcgactc      60 tcctgtgcag cctctggatt caccttcagt agctactgga tgtattggct ccgtcaggct    120
ccagggaagg ggctcgagtg ggtctcatct attagtggta gtagtagtag cacatactat    180
cgagactccg tgaagggccg attcaccatc tccagagaca cgccaagaa cacgctgtat     240 ctgcaaatga acagtctgaa atctgaggac acggccgtgt attactgtgc aaaagatcct    300
ggtgggtacg ccaaaggcca ggggacccag gtcaccgtct ccagt                    345

<210> SEQ ID NO 99
<211> LENGTH: 226
<212> TYPE: PRT
<213> ORGANISM: Artificial Sequence
<220> FEATURE:
<223> OTHER INFORMATION: IgG1 Fc fragment amino acid sequence

<400> SEQUENCE: 99

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

```
Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly
225
```

<210> SEQ ID NO 100
<211> LENGTH: 21
<212> TYPE: PRT
<213> ORGANISM: Artificial Sequence
<220> FEATURE:
<223> OTHER INFORMATION: fusion protein linker amino acid sequence

<400> SEQUENCE: 100

```
Gly Gly Gly Gly Ser Gly Gly Gly Ser Gly Gly Gly Ser Gly
1               5                   10                  15

Gly Gly Ser Gly
            20
```

<210> SEQ ID NO 101
<211> LENGTH: 136
<212> TYPE: PRT
<213> ORGANISM: Artificial Sequence
<220> FEATURE:
<223> OTHER INFORMATION: TGFbetaRII extracellular domain amino acid
      sequence

<400> SEQUENCE: 101

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
                20                  25                  30

Val Arg Phe Ser Thr Cys Asp Asn Gln Lys Ser Cys Met Ser Asn Cys
            35                  40                  45

Ser Ile Thr Ser Ile Cys Glu Lys Pro Gln Glu Val Cys Val Ala Val
 50                  55                  60

Trp Arg Lys Asn Asp Glu Asn Ile Thr Leu Glu Thr Val Cys His Asp
```

```
                    65                  70                  75                  80
Pro Lys Leu Pro Tyr His Asp Phe Ile Leu Glu Asp Ala Ala Ser Pro
                            85                  90                  95

Lys Cys Ile Met Lys Glu Lys Lys Pro Gly Glu Thr Phe Phe Met
                100                 105                 110

Cys Ser Cys Ser Ser Asp Glu Cys Asn Asp Asn Ile Ile Phe Ser Glu
                115                 120                 125

Glu Tyr Asn Thr Ser Asn Pro Asp
        130                 135

<210> SEQ ID NO 102
<211> LENGTH: 498
<212> TYPE: PRT
<213> ORGANISM: Artificial Sequence
<220> FEATURE:
<223> OTHER INFORMATION: PM8001 amino acid sequence

<400> SEQUENCE: 102

Glu Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Leu Arg Gln Ala Pro Gly Lys Gly Leu Glu Trp Val
        35                  40                  45

Ser Ser Ile Asn Ser Asp Ser Ser Thr Tyr Tyr Arg Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
            85                  90                  95

Ala Lys Asp Pro Gly Gly Tyr Ala Lys Gly Gln Gly Thr Gln Val Thr
                100                 105                 110

Val Ser Ser Asp Lys Thr His Thr Cys Pro Pro Cys Pro Ala Pro Glu
            115                 120                 125

Ala Ala Gly Gly Pro Ser Val Phe Leu Phe Pro Lys Pro Lys Asp
        130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Asp Glu Leu Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Tyr Ser Lys
```

```
                    290                 295                 300
Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Gly Gly Gly Ser Gly Gly Gly Gly Ser Gly
            340                 345                 350

Gly Gly Gly Ser Gly Gly Gly Gly Ser Gly Ile Pro Pro His Val Gln
            355                 360                 365

Lys Ser Val Asn Asn Asp Met Ile Val Thr Asp Asn Asn Gly Ala Val
            370                 375                 380

Lys Phe Pro Gln Leu Cys Lys Phe Cys Asp Val Arg Phe Ser Thr Cys
385                 390                 395                 400

Asp Asn Gln Lys Ser Cys Met Ser Asn Cys Ser Ile Thr Ser Ile Cys
                405                 410                 415

Glu Lys Pro Gln Glu Val Cys Val Ala Val Trp Arg Lys Asn Asp Glu
            420                 425                 430

Asn Ile Thr Leu Glu Thr Val Cys His Asp Pro Lys Leu Pro Tyr His
            435                 440                 445

Asp Phe Ile Leu Glu Asp Ala Ala Ser Pro Lys Cys Ile Met Lys Glu
            450                 455                 460

Lys Lys Lys Pro Gly Glu Thr Phe Phe Met Cys Ser Cys Ser Ser Asp
465                 470                 475                 480

Glu Cys Asn Asp Asn Ile Ile Phe Ser Glu Glu Tyr Asn Thr Ser Asn
                485                 490                 495

Pro Asp

<210> SEQ ID NO 103
<211> LENGTH: 23
<212> TYPE: DNA
<213> ORGANISM: Artificial Sequence
<220> FEATURE:
<223> OTHER INFORMATION: upstream primer for first round

<400> SEQUENCE: 103
gtcctggctg ctcttctaca agg                                          23

<210> SEQ ID NO 104
<211> LENGTH: 23
<212> TYPE: DNA
<213> ORGANISM: Artificial Sequence
<220> FEATURE:
<223> OTHER INFORMATION: downstream primer for first round

<400> SEQUENCE: 104
ggtacgtgct gttgaactgt tcc                                          23

<210> SEQ ID NO 105
<211> LENGTH: 33
<212> TYPE: DNA
<213> ORGANISM: Artificial Sequence
<220> FEATURE:
<223> OTHER INFORMATION: upstream primer for second round

<400> SEQUENCE: 105
ctagtgcggc cgcctggaga cggtgacctg ggt                               33

<210> SEQ ID NO 106
<211> LENGTH: 38
```

```
<212> TYPE: DNA
<213> ORGANISM: Artificial Sequence
<220> FEATURE:
<223> OTHER INFORMATION: downstream primer for second round

<400> SEQUENCE: 106
cgcggatccc aggtgcagct gcaggagtct ggrggagg                              38

<210> SEQ ID NO 107
<211> LENGTH: 89
<212> TYPE: DNA
<213> ORGANISM: Artificial Sequence
<220> FEATURE:
<223> OTHER INFORMATION: upstream primer for third round

<400> SEQUENCE: 107
atttttactg ctgttttatt cgcagcatcc tccgcattag ctaaaagaga ggctgaagca      60
caggtgcagc tgcaggagtc tggrggagg                                        89

<210> SEQ ID NO 108
<211> LENGTH: 81
<212> TYPE: DNA
<213> ORGANISM: Artificial Sequence
<220> FEATURE:
<223> OTHER INFORMATION: downstream primer for third round

<400> SEQUENCE: 108
agttgtcagt tcctgtgccc ccctcctcc cgcgccacct ccgcccgcac ctccgccacc       60
actggagacg gtgacctggg t                                                81

<210> SEQ ID NO 109
<211> LENGTH: 123
<212> TYPE: PRT
<213> ORGANISM: Artificial Sequence
<220> FEATURE:
<223> OTHER INFORMATION: PD-L1-His tag amino acid sequence

<400> SEQUENCE: 109

Met Phe Thr Val Thr Val Pro Lys Asp Leu Tyr Val Val Glu Tyr Gly
1               5                   10                  15

Ser Asn Met Thr Ile Glu Cys Lys Phe Pro Val Glu Lys Gln Leu Asp
            20                  25                  30

Leu Ala Ala Leu Ile Val Tyr Trp Glu Met Glu Asp Lys Asn Ile Ile
        35                  40                  45

Gln Phe Val His Gly Glu Glu Asp Leu Lys Val Gln His Ser Ser Tyr
    50                  55                  60

Arg Gln Arg Ala Arg Leu Leu Lys Asp Gln Leu Ser Leu Gly Asn Ala
65                  70                  75                  80

Ala Leu Gln Ile Thr Asp Val Lys Leu Gln Asp Ala Gly Val Tyr Arg
                85                  90                  95

Cys Met Ile Ser Tyr Gly Gly Ala Asp Tyr Lys Arg Ile Thr Val Lys
            100                 105                 110

Val Asn Ala Pro Tyr His His His His His His
            115                 120

<210> SEQ ID NO 110
<211> LENGTH: 341
<212> TYPE: PRT
<213> ORGANISM: Artificial Sequence
<220> FEATURE:
<223> OTHER INFORMATION: PD-L1 single-domain antibody fusion protein
      amino acid sequence
```

<400> SEQUENCE: 110

```
Glu Val Gln Leu Gln Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Trp Met Tyr Trp Leu Arg Gln Ala Pro Gly Lys Gly Leu Glu Trp Val
         35                  40                  45

Ser Ser Ile Asn Ser Asp Ser Ser Thr Tyr Tyr Arg Asp Ser Val
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Ser Glu Asp Thr Ala Val Tyr Tyr Cys
             85                  90                  95

Ala Lys Asp Pro Gly Gly Tyr Ala Lys Gly Gln Gly Thr Gln Val Thr
         100                 105                 110

Val Ser Ser Asp Lys Thr His Thr Cys Pro Pro Cys Pro Ala Pro Glu
         115                 120                 125

Ala Ala Gly Gly Pro Ser Val Phe Leu Phe Pro Pro Lys Pro Lys Asp
     130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
             165                 170                 175

Val Glu Val His Asn Ala Lys Thr Lys Pro Arg Glu Glu Gln Tyr Asn
         180                 185                 190

Ser Thr Tyr Arg Val Val Ser Val Leu Thr Val Leu His Gln Asp Trp
     195                 200                 205

Leu Asn Gly Lys Glu Tyr Lys Cys Lys Val Ser Asn Lys Ala Leu Pro
210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Asp Glu Leu Thr Lys Asn
             245                 250                 255

Gln Val Ser Leu Thr Cys Leu Val Lys Gly Phe Tyr Pro Ser Asp Ile
         260                 265                 270

Ala Val Glu Trp Glu Ser Asn Gly Gln Pro Glu Asn Asn Tyr Lys Thr
     275                 280                 285

Thr Pro Pro Val Leu Asp Ser Asp Gly Ser Phe Phe Leu Tyr Ser Lys
290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
             325                 330                 335

Ser Leu Ser Pro Gly
             340
```

<210> SEQ ID NO 111  
<211> LENGTH: 117  
<212> TYPE: PRT  
<213> ORGANISM: Artificial Sequence  
<220> FEATURE:  
<223> OTHER INFORMATION: PD-L1 single-domain antibody amino acid sequence

<400> SEQUENCE: 111

```
Glu Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Leu Arg Gln Ala Pro Gly Lys Gly Leu Glu Trp Val
        35                  40              45

Ser Ser Ile Asn Ser Asp Ser Ser Thr Tyr Tyr Arg Asp Ser Val
        50              55                  60

Lys Gly Arg Phe Thr Ile Ser Arg Asp Asn Ala Lys Asn Thr Leu Tyr
65                  70              75                  80

Leu Gln Met Asn Ser Leu Lys Ser Glu Asp Thr Ala Val Tyr Tyr Cys
                85                  90                  95

Ala Lys Asp Pro Gly Gly Tyr Ala Lys Gly Gln Gly Thr Gln Val Thr
            100                 105                 110

Val Ser Ser Asp Lys
            115
```